United States Patent [19]

Castro

[11] 4,247,498
[45] Jan. 27, 1981

[54] METHODS FOR MAKING MICROPOROUS PRODUCTS

[75] Inventor: Anthony J. Castro, Oak Park, Ill.

[73] Assignee: Akzona Incorporated, Asheville, N.C.

[21] Appl. No.: 963,628

[22] Filed: Nov. 24, 1978

Related U.S. Application Data

[60] Division of Ser. No. 814,351, Jul. 11, 1977, which is a continuation-in-part of Ser. No. 718,549, Aug. 30, 1976, abandoned.

[51] Int. Cl.$^3$ .......................................... B29D 27/04
[52] U.S. Cl. ...................................... 264/41; 264/28; 264/49
[58] Field of Search ................................ 264/28, 41, 49

[56] References Cited

U.S. PATENT DOCUMENTS

| | | | |
|---|---|---|---|
| 2,461,480 | 2/1949 | Reckmeyer | 264/28 X |
| 3,055,297 | 9/1962 | Leeds . | |
| 3,055,966 | 9/1962 | Sandberg . | |
| 3,308,073 | 3/1967 | Kepple . | |
| 3,378,507 | 4/1968 | Sargent et al. . | |
| 3,403,046 | 9/1968 | Schwacke et al. | 264/28 X |
| 3,408,315 | 10/1968 | Paine . | |
| 3,427,277 | 2/1969 | Davis . | |
| 3,428,584 | 2/1969 | Riley | 264/48 X |
| 3,513,110 | 5/1970 | Noether . | |
| 3,589,929 | 6/1971 | Smolders et al. . | |
| 3,607,793 | 9/1971 | Maalman . | |
| 3,642,668 | 2/1972 | Bailey et al. . | |
| 3,682,848 | 8/1972 | Virnelson . | |
| 3,746,668 | 7/1973 | Hiratsuka et al. | 264/41 |
| 3,752,784 | 8/1973 | Jenkins . | |
| 3,753,932 | 8/1973 | Jenkins . | |
| 3,785,919 | 1/1974 | Hickman . | |
| 3,812,224 | 5/1974 | Smith et al. | 264/28 |
| 3,839,516 | 10/1974 | Williams et al. . | |
| 3,876,738 | 4/1975 | Marinaccio et al. . | |
| 3,939,237 | 2/1976 | Naito et al. | 264/54 |
| 4,049,589 | 9/1977 | Sakane . | |
| 4,118,449 | 10/1978 | Rinde | 264/41 |

FOREIGN PATENT DOCUMENTS

| | | | |
|---|---|---|---|
| 44-22631 | 9/1969 | Japan | 264/28 |
| 51-54668 | 5/1976 | Japan | 264/28 |

OTHER PUBLICATIONS

Marangoni, Carl, C. Ann. Phys. LPZ (1871), pp. 143, 337–354.
Marangoni, Carlo, Nuovo Cimento[3] pp. 3, 97, 193–208.
Charles, G.E. and S. G. Mason, "The Coalescence of Liquid Drops with Flat Liquid/Liquid Interfaces," in Journal of Colloid Science, pp. 5, 236–267 (1960).
Billmeyer, Fred W., "Textbook of Polymer Science," Second Edition, New York, Wiley-Interscience, ©1971, pp. 120, 121, 167–174.
"McGraw-Hill Dictionary of Scientific and Technical Terms," Second Edition, Daniel N. Lapedes, Editor in Chief, New York, McGraw-Hill, ©1978, pp. 177, 384, 394, 417, 1091, 1512.

Primary Examiner—Philip Anderson
Attorney, Agent, or Firm—Francis W. Young; Robert F. Green

[57] ABSTRACT

Novel microporous polymers in forms ranging from films to blocks and intricate shapes from synthetic thermoplastic polymers, such as, olefinic, condensation, and oxidation polymers, are disclosed. In one embodiment the microporous polymers are characterized by a relatively homogeneous, three-dimensional cellular structure having cells connected by pores of smaller dimension. Also disclosed is a process for making microporous polymers from such thermoplastic polymers by heating a mixture of the polymer and a compatible liquid to form a homogeneous solution, cooling said solution under non-equilibrium thermodynamic conditions to initiate liquid-liquid phase separation, and continuing said cooling until the mixture achieves substantial handling strength. Also disclosed are microporous polymer products which contain relatively large amounts of functionally useful liquids and behave as solids.

37 Claims, 71 Drawing Figures

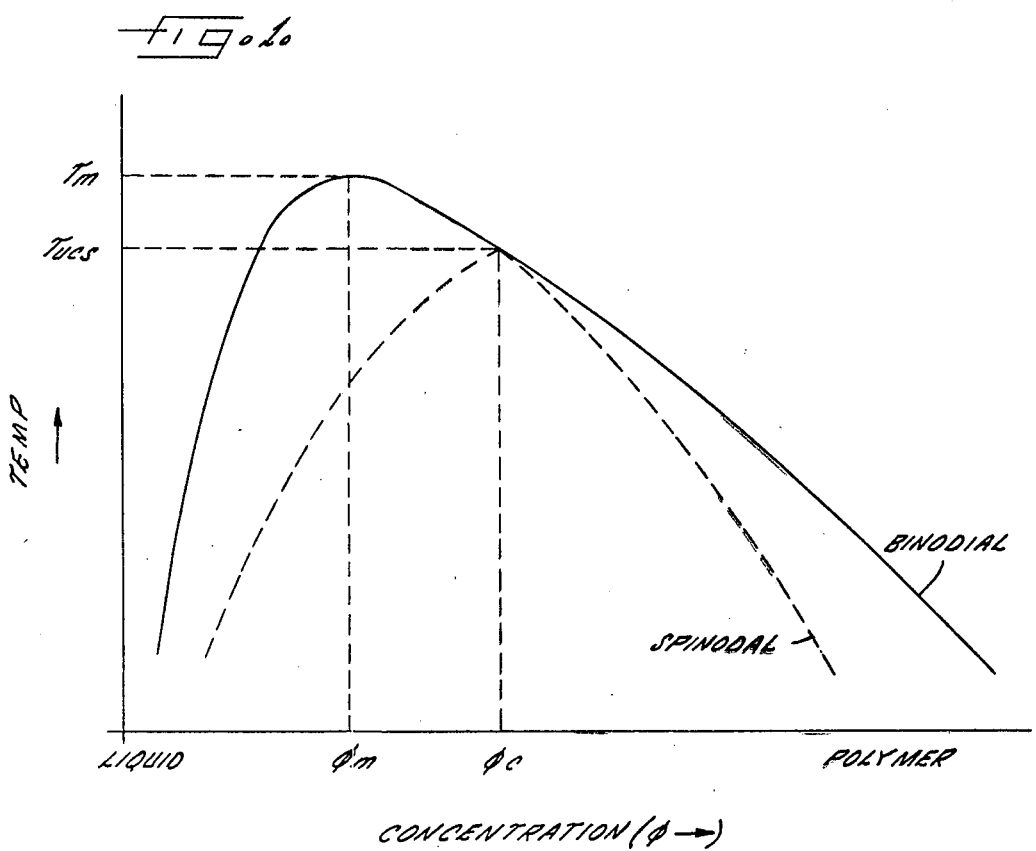

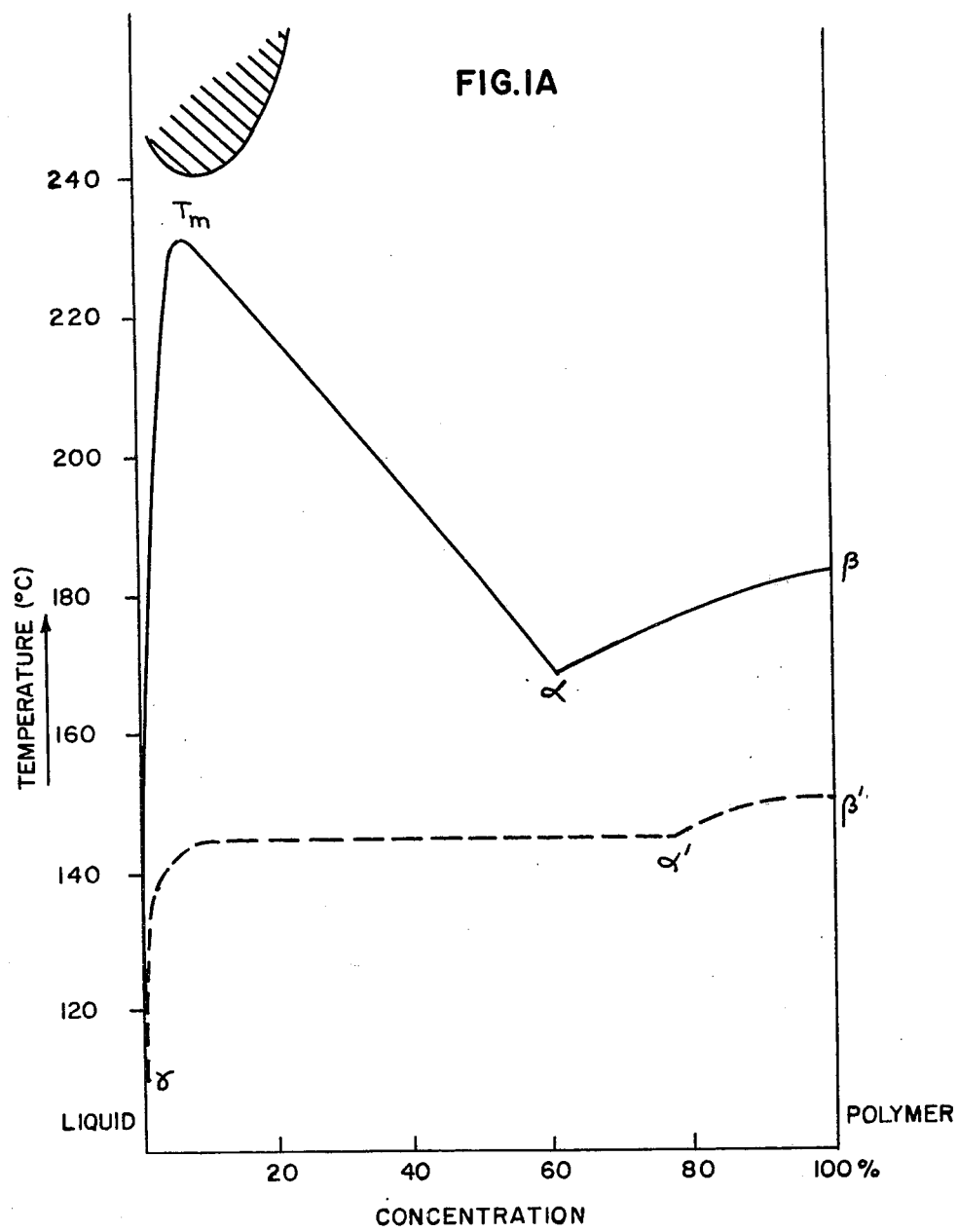

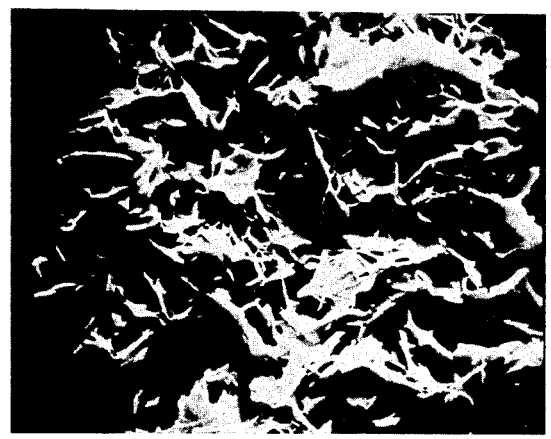
FIG. 22
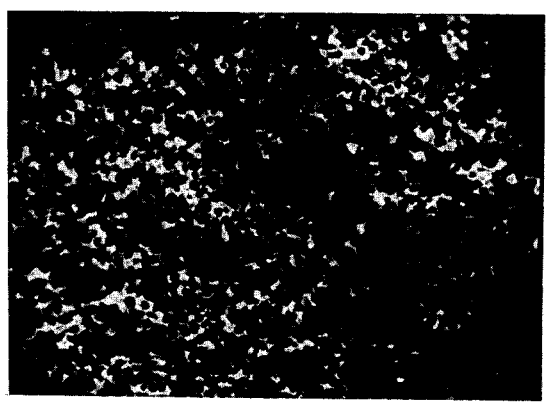 
FIG. 23        FIG. 24

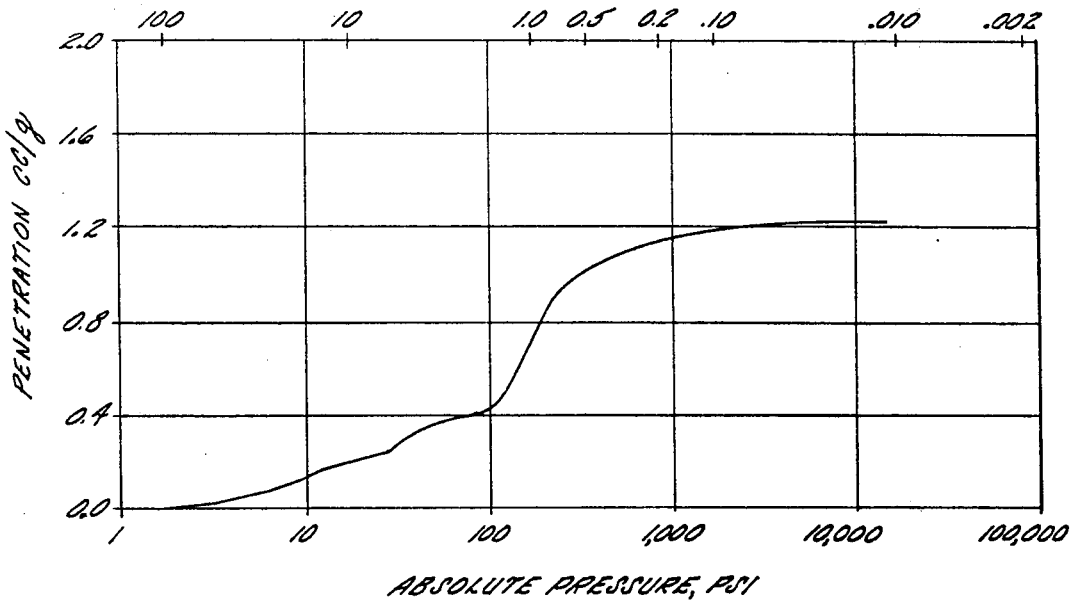
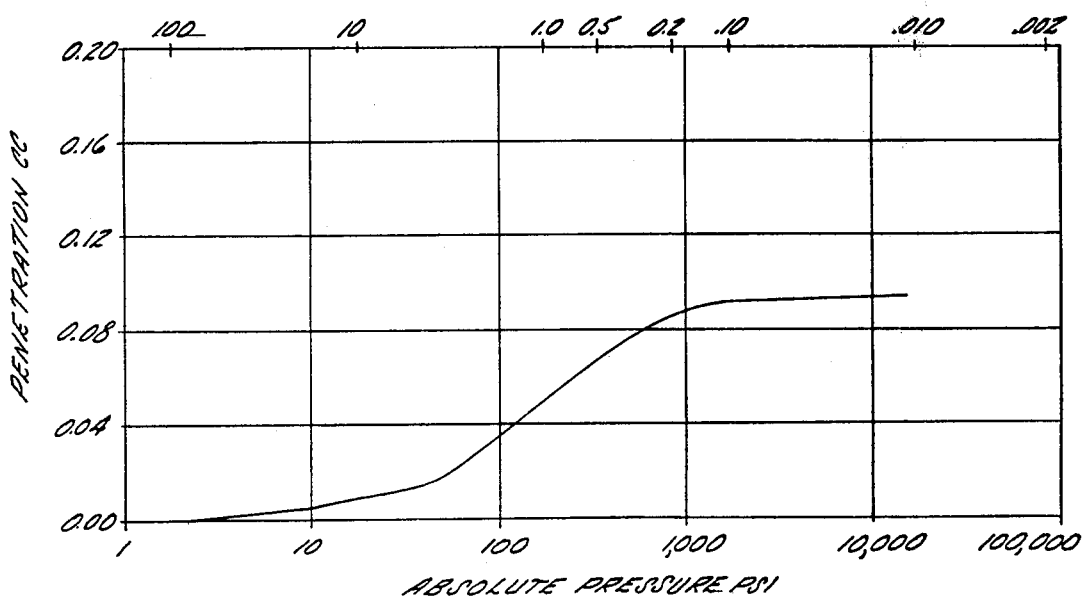

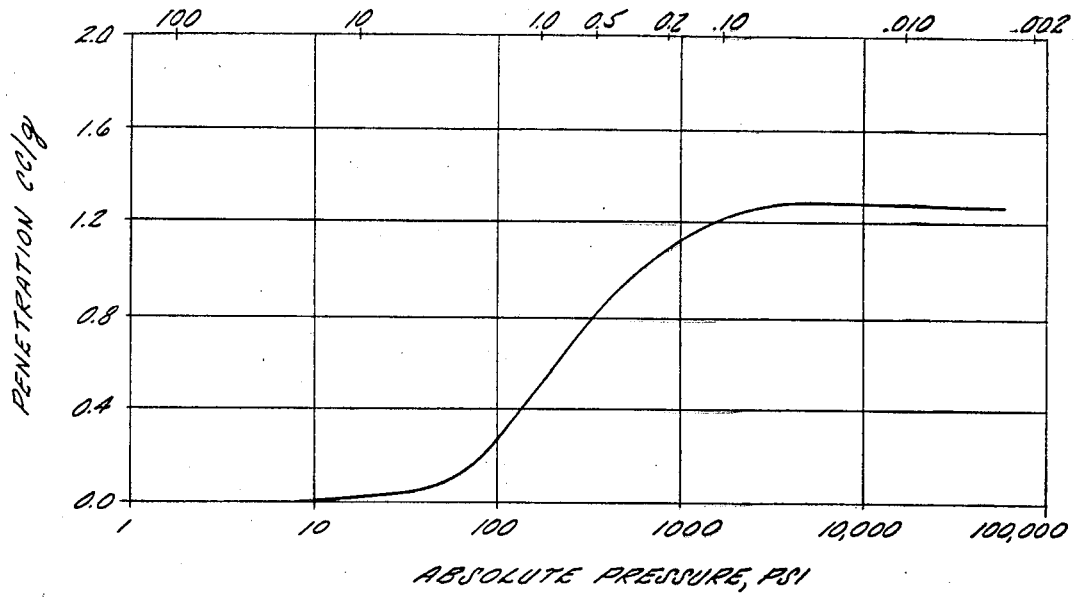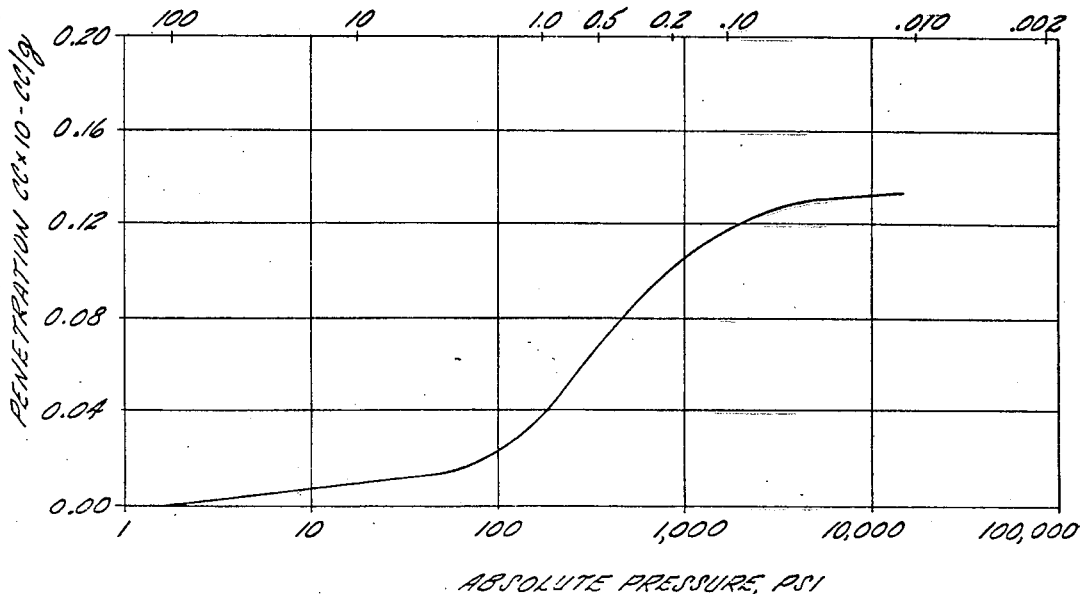

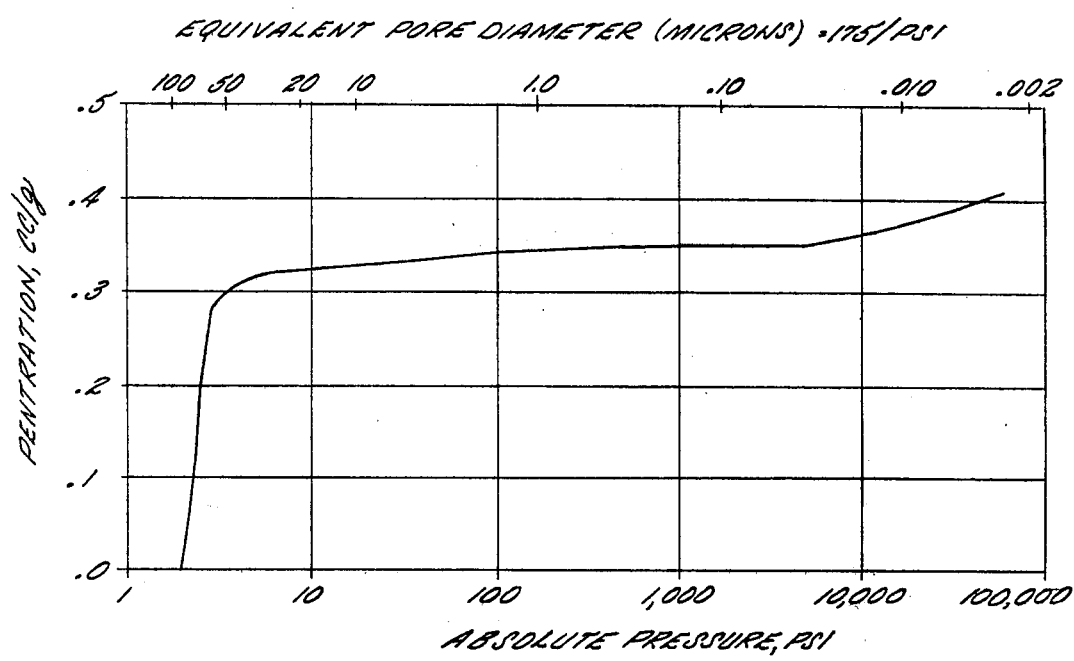

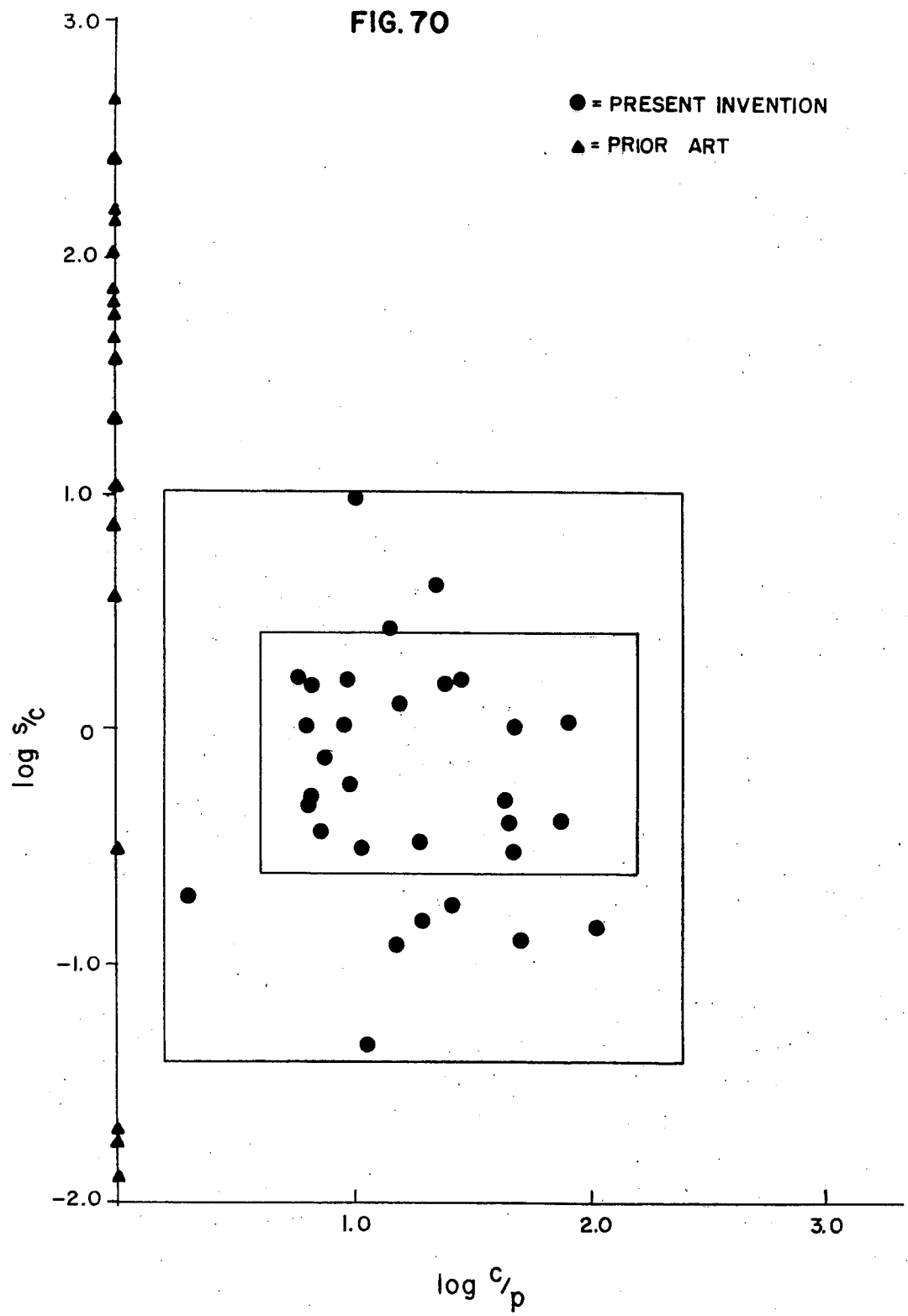

METHODS FOR MAKING MICROPOROUS PRODUCTS

This is a division of application Ser. No. 814,351, filed July 11, 1977, a continuation-in-part of application Ser. No. 718,549, filed Aug. 30, 1976 now abandoned.

RELATED APPLICATIONS

Castro and Stoll, Ser. No. 622,643, filed: Oct. 15, 1975, for: Solid Antistat Compositions; a continuation-in-part of Ser. No. 436,252, filed: Jan. 24, 1974, now abandoned.

BACKGROUND OF THE INVENTION

This invention relates to porous polymer structures and a method of preparing the same. More particularly, this invention relates to microporous polymer structures that may be readily prepared and are characterized by relatively homogeneous, three-dimensional, cellular microstructures and to a unique, facile process for preparing microporous polymer structures.

Several widely differing techniques have been previously developed for preparing microporous polymer structures. Such techniques range from what is termed, in the art, classical phase inversion, to nuclear bombardment, to incorporation of microporous solid particles in a substrate which are subsequently leached out, to sintering microporous particles together in some fashion. Prior efforts in the field have entailed still other techniques as well as innummerable variations of what may be considered as the classical or basic techniques.

The interest in microporous polymer products has been engendered by the numerous potential applications for materials of this type. These potential applications are well known and range from ink pads, or the like, to leather-like breathable sheets, to filter media. Yet, with all of the potential applications, the commercial usage has been relatively modest. And, the techniques being commercially utilized have various limitations which do not allow the versatility required to expand the applications to reach the potential market for microporous products.

As mentioned, some commercially available microporous polymer products are made by a nuclear bombardment technique. Such a technique is capable of achieving a rather narrow pore size distributing; however, the pore volume must be relatively low (i.e.—less than about 10% void space) to insure that the polymer will not be degraded during preparation. Many polymers cannot be utilized in such a technique due to the lack of the ability of the polymer to etch. Still further, the technique requires that a relatively thin sheet or film of the polymer be used and considerable expertise must be employed in carrying out the procedure to avoid "double tracking", which results in the formation of oversized pores.

Classical phase inversion has also been commercially utilized to form microporous polymers from cellulose acetate and certain other polymers. Classical phase inversion has been reviewed in great detail by R. E. Kesting in *SYNTHETIC POLYMERIC MEMBRANES*, McGraw-Hill, 1971. In particular at page 117 of said reference it is explicitly stated that classical phase inversion involves the use of at least three components, a polymer, a solvent for said polymer and a nonsolvent for said polymer.

Reference may also be made to U.S. Pat. No. 3,945,926 which teaches the formation of polycarbonate resin membranes from a casting solution containing the resin, a solvent, and a swelling agent and/or a nonsolvent. It is stated at lines 42–47, column 15, of said patent that in the complete absence of a swelling agent phase inversion usually does not occur and that with low concentrations of swelling agents, structures possessing closed cells are encountered.

From the foregoing discussion it is quite apparent that classical phase inversion requires the use of a solvent for the system at room temperature so that many other useful polymers cannot be substituted for the polymers such as cellulose acetate. Also from the process standpoint, the classical phase inversion process will generally be restricted to the formation of films due to the large amount of solvent used in the preparation of solutions which must be subsequently extracted. It is also apparent that classical phase inversion requires a relatively high degree of process control to obtain structures of desired configuration. Thus the relative concentrations of solvent, nonsolvent, and swelling agent must be critically controlled, as discussed in column 14–16 of U.S. Pat. No. 3,945,926. Conversely, to alter the number, size, and homogeneity of the resultant structure, one must modify the aforementioned parameters by trial-and-error.

Other commercially available microporous polymers are made by sintering microporous particles of polymers ranging from high density polyethylene to polyvinylidene fluoride. However, it is difficult with such a technique to obtain a product with the narrow pore size distribution required for many applications.

A still further general technique which has been the subject of considerable prior effort involves heating a polymer with various liquids to form a dispersion or solution and thereafter cooling, followed by removal of the liquid with a solvent or the like. This type of process is disclosed in the following U.S. Patents which are only representative and not cumulative: Nos. 3,607,793; 3,378,507; 3,310,505; 3,748,287; 3,536,796; 3,308,073; and 3,812,224. It is not believed that the foregoing technique has been utilized commercially to any significant extent, if at all, probably due to the lack of economic feasibility of the particular processes which have previously been developed. Also, the prior processes do not allow the preparation of microporous polymers which combine relatively homogeneous microcellular structures with the pore size and pore size distributions which are typically desired.

With respect to the microporous polymers obtained by prior art techniques, no process known heretofore has been capable of yielding isotropic olefinic or oxidation polymers which have the major portion of pore sizes in the range of about 0.1 to about 5 microns while having a relatively narrow pore size distribution, thus exhibiting a high degree of pore size uniformity throughout a sample thereof. Some prior art olefinic or oxidation polymers have had pore sizes in the foregoing range, but without a relatively narrow pore size distribution, thus making such materials without significant value in application areas, such as filtration, which require a high degree of selectivity. Furthermore, prior microporous olefinic or oxidation polymers which may be considered to have relatively narrow pole size distributions have had absolute pore sizes which are outside the aforementioned range, usually having substantially smaller pore sizes, for use in application areas such as ultra-filtration. Finally, some prior art olefinic polymers have had pore sizes in the foregoing range and what may be considered to be relatively narrow pore size distributions. However, such materials have been made by use of techniques, such as stretching which impart a high degree of orientation to the resultant anisotropic material, rendering it undesirable for many application areas. There thus has existed a need for microporous olefinic and oxidation polymers having a pore size in a range of from about 0.1 to about 5 microns and characterized as having a relatively narrow isotropic pore size distribution.

Also, a major drawback of many microporous polymers available heretofore has been the low flow rate of such polymers when used in structures such as microfiltration membranes. One of the major reasons for such low flow rates is the typically low void volume of many such polymers. Thus, perhaps 20 percent of the polymer structure, or less, may be "void" volume through which a filtrate may flow, the remaining 80 percent of the structure being the polymer resin which forms the microporous structure. Thus, there has also existed a need for microporous polymers having a high degree of void volume, especially with respect to olefinic polymers.

The copending Castro and Stoll application, previously identified herein, discloses a highly advantageous method for converting a particular type of liquid amine antistatic agent to a material which behaves as a solid. The advantages in processing which result are real and significant. It would be similarly beneficial to be able to convert other useful functional liquids such as flame retardants and the like to materials which behave as solids.

It is accordingly an object of the present invention to provide microporous polymer products characterized by relative homogeneity and narrow pore size distributions.

Another object is to provide a facile process which allows the economic production of microporous polymers.

A still further object lies in the provision of a process for making microporous polymer products, which has applicability to a wide number of useful thermoplastic polymers. A related and more specific object is to provide such a process which is capable of readily forming microporous polymers from any synthetic thermoplastic polymer including polyolefins, condensation polymers and oxidation polymers.

Yet another object of this invention is to provide microporous polymers in structures ranging from thin films to relatively thick blocks. A related object is to provide the ability to form microporous polymers in intricate shapes.

A further object is to provide the conversion of functional liquids to materials which possess the characteristics of a solid.

Other objects and advantages of the present invention will become apparent from the following discussion, and from the drawings, in which:

FIG. 1 is a graph of temperature vs. concentration for a hypothetical polymer-liquid system, setting forth the binodial and spinodal curves, and illustrating the concentration necessary to achieve the microporous polymers and to practice the process of the present invention;

FIG. 1A is a graph of temperature vs. concentration similar to that of FIG. 1, but also including the freezing point depression phase line;

Figure 11:
Figure 12:
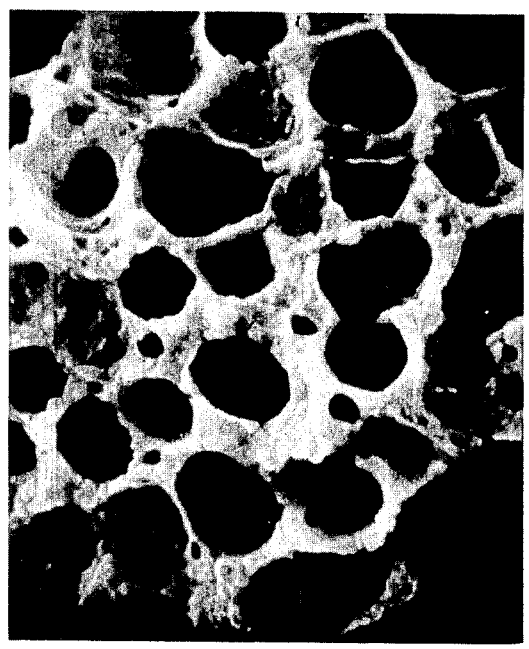
Figure 13:
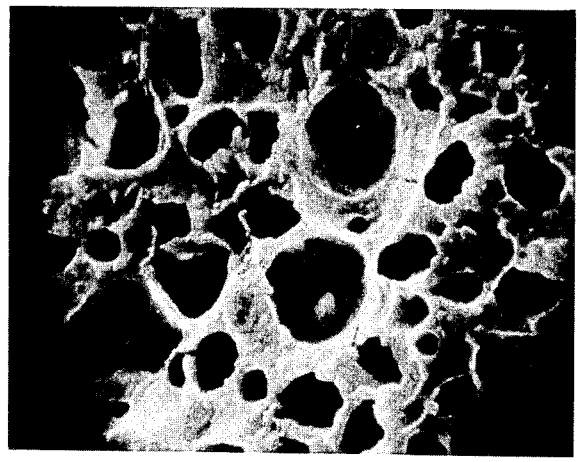
Figure 14:
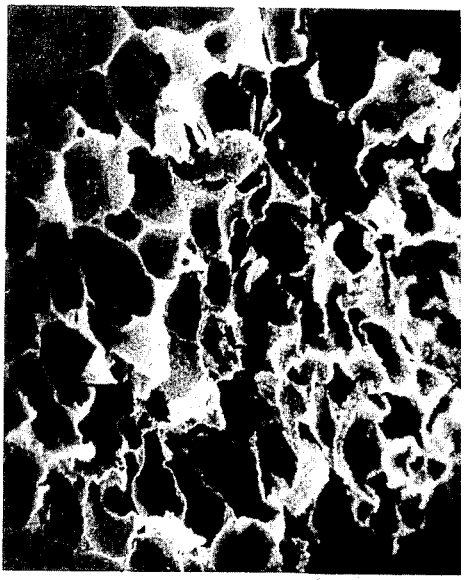
Figure 15:
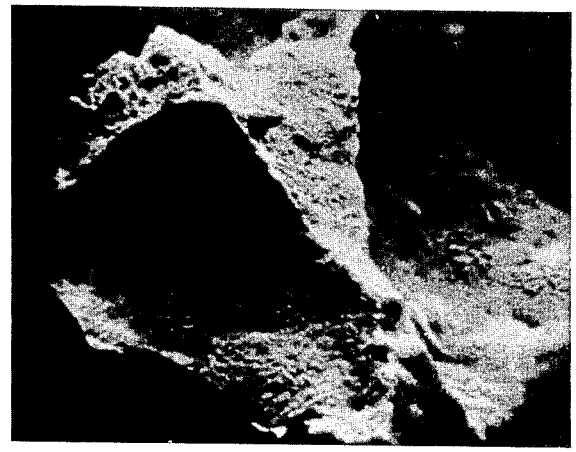
Figure 16:
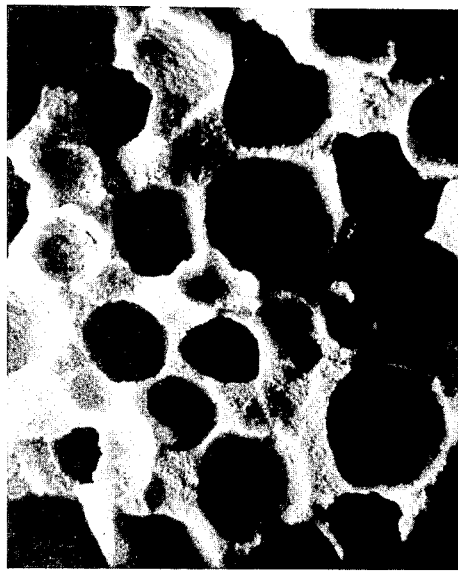
Figure 17:
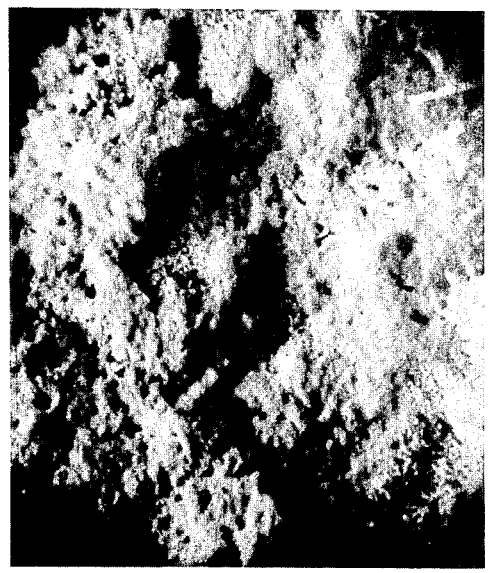
Figure 18:
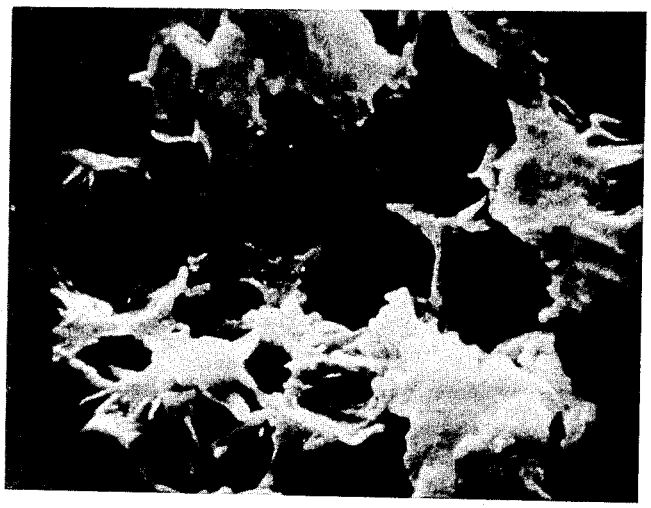
Figure 19:
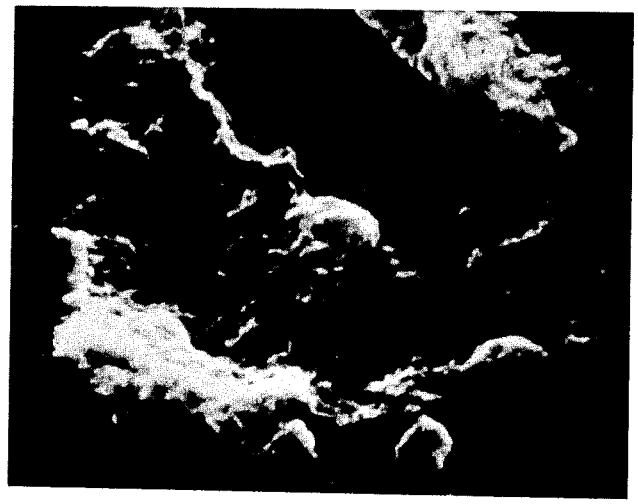
Figure 20:
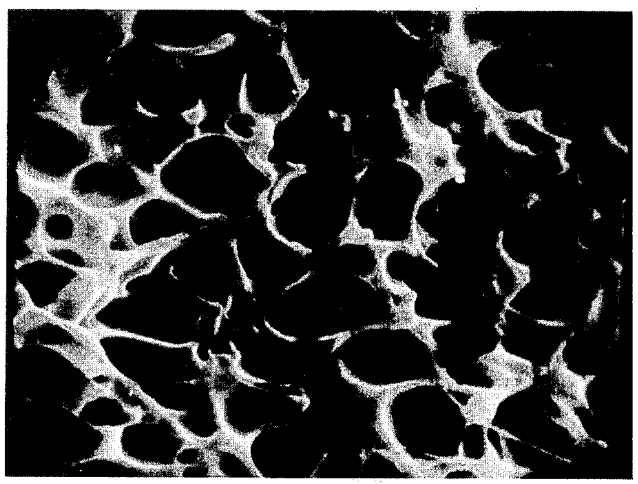
Figure 21:
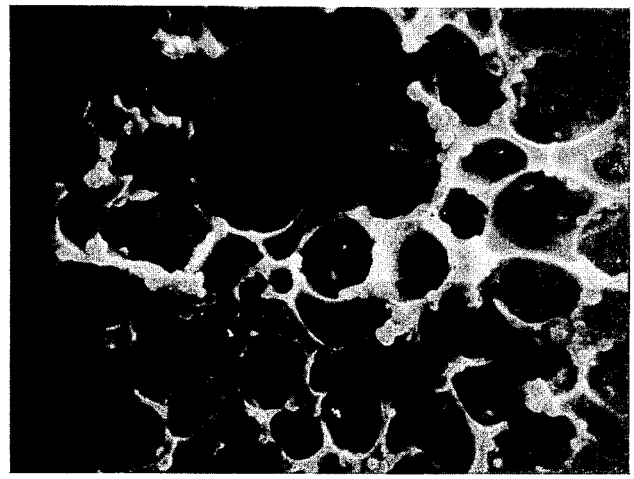
Figure 25:
Figure 26:
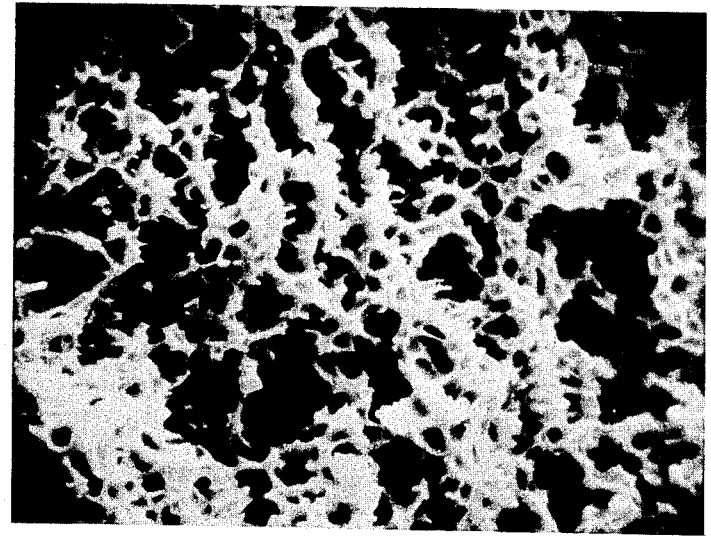
Figure 27:
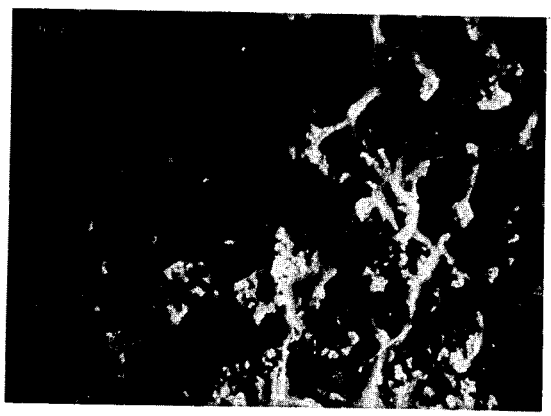
Figure 28:
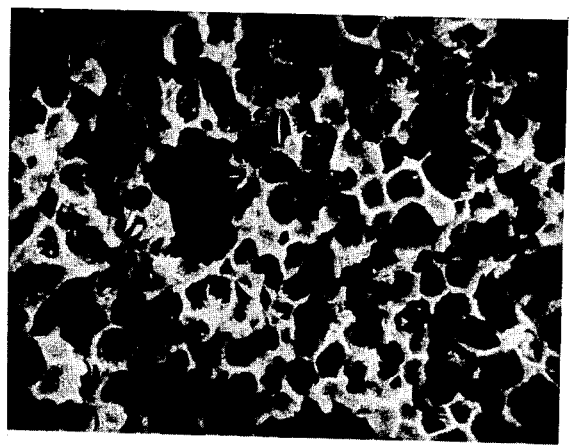
Figure 29:
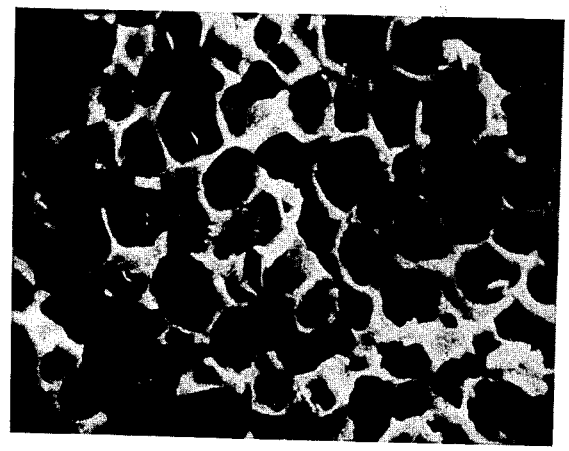
Figure 33:
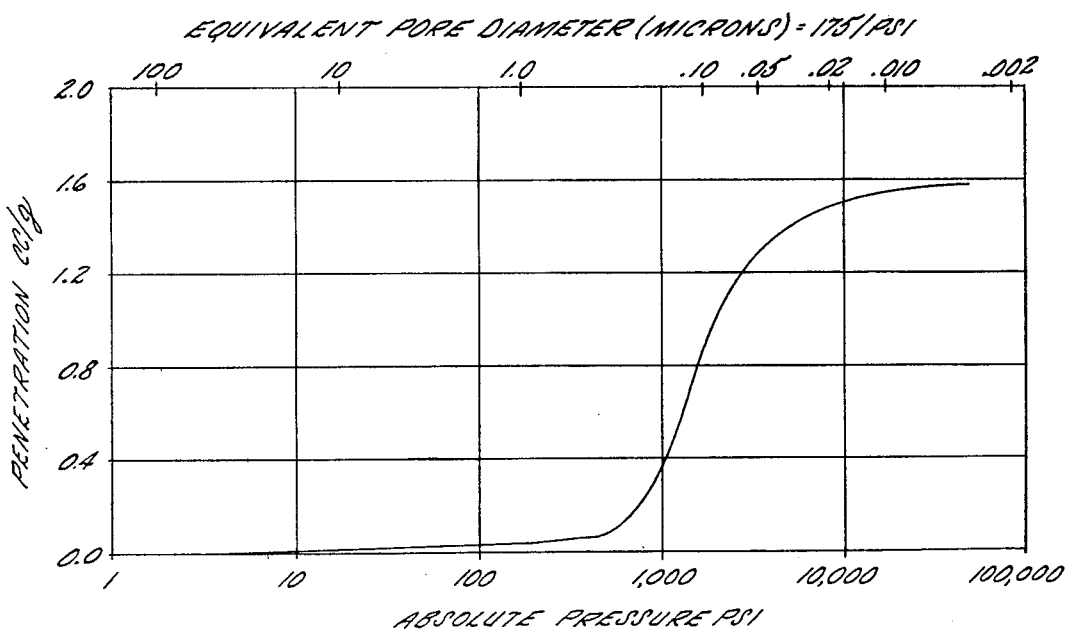
Figure 37:
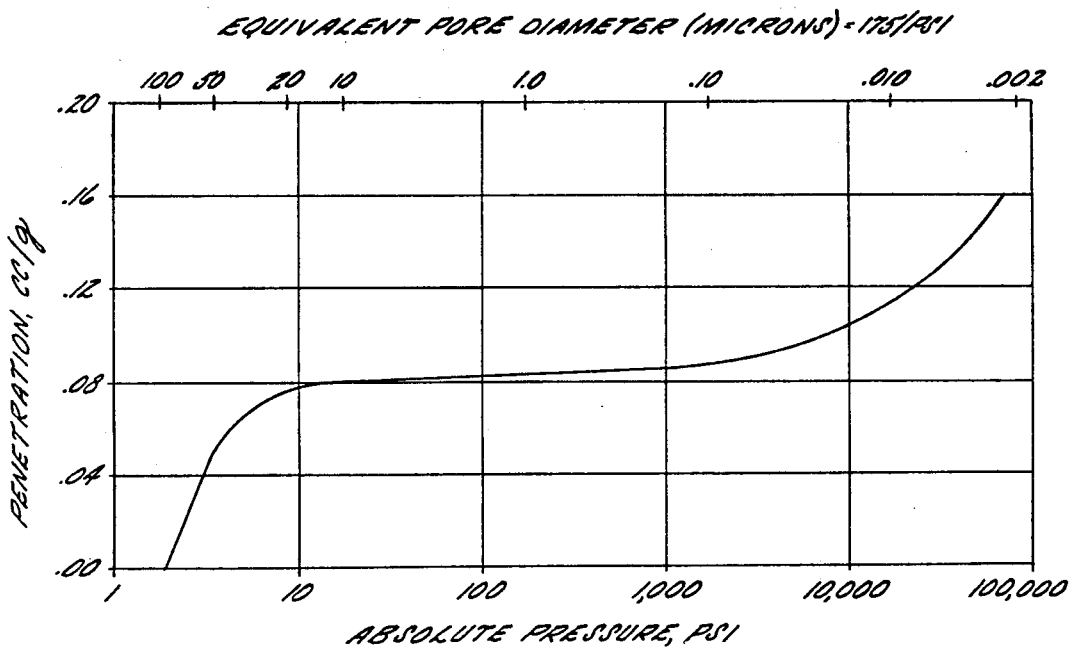
Figure 38:
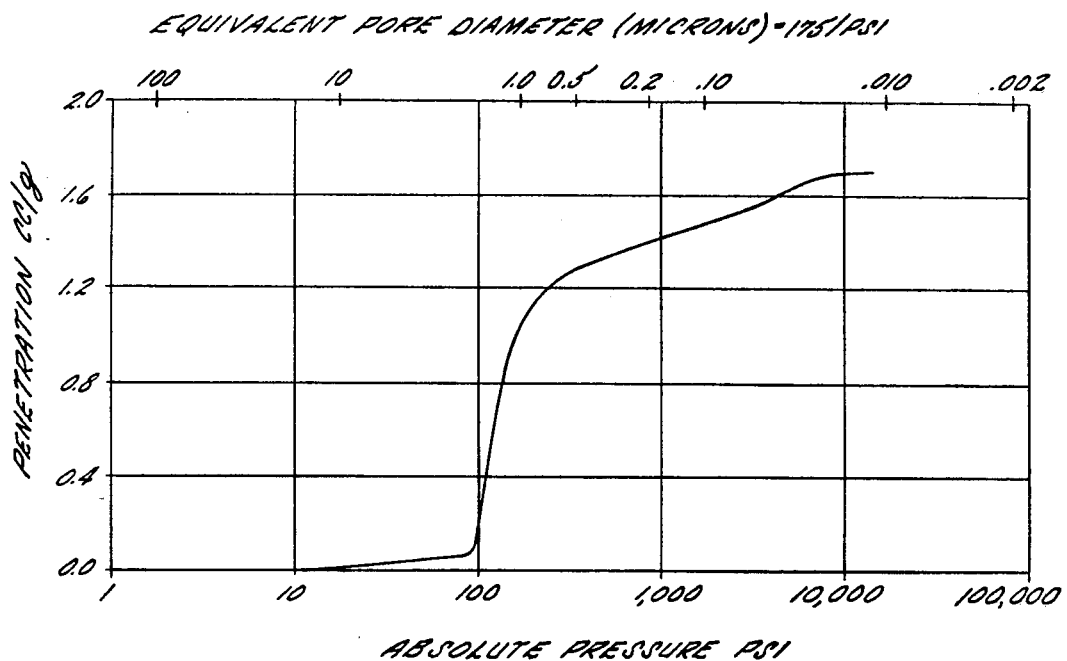
Figure 39:
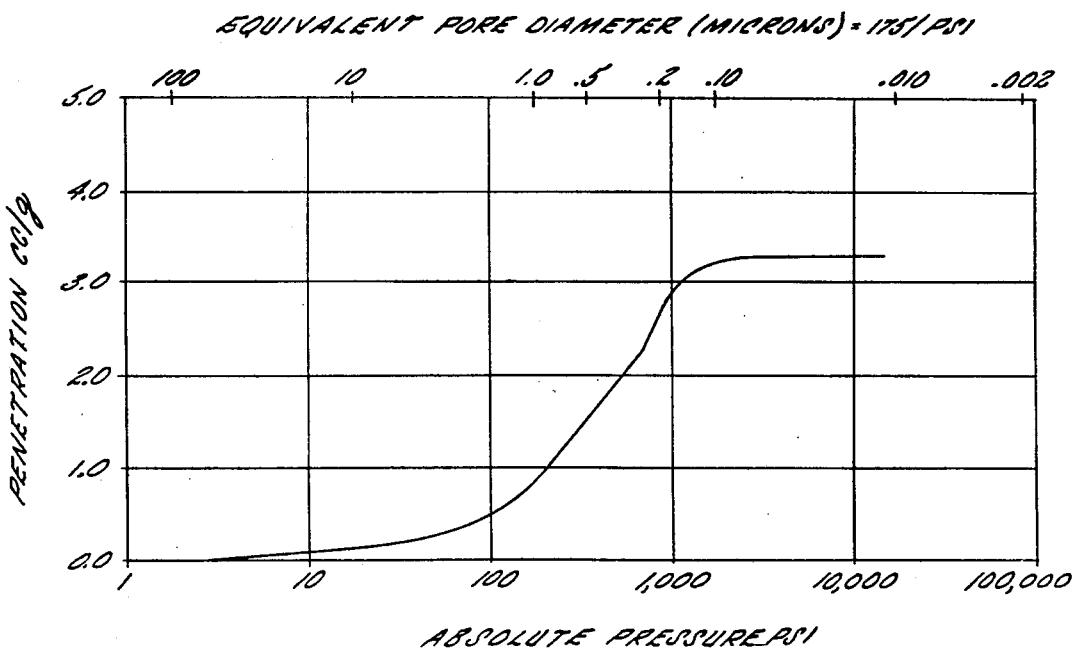
Figure 45:
Figure 46:
Figure 47:
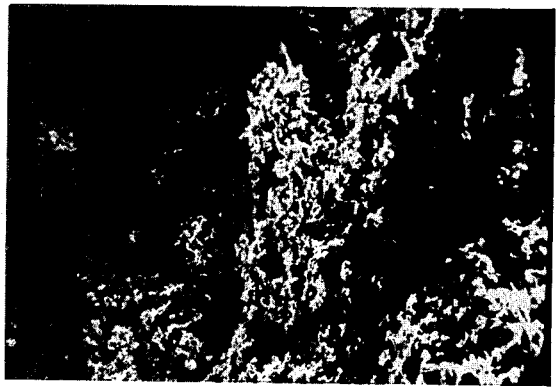
Figure 48:
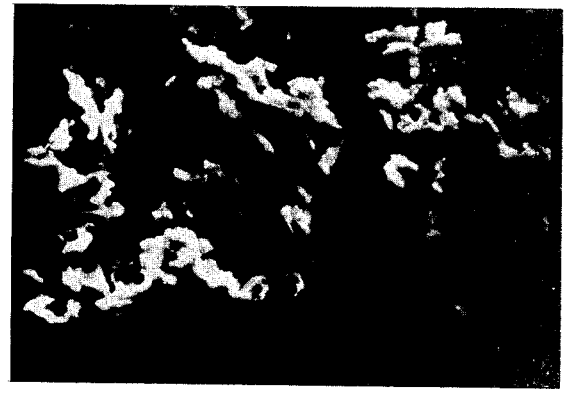
Figure 49:
Figure 50:
Figure 51:
Figure 52:
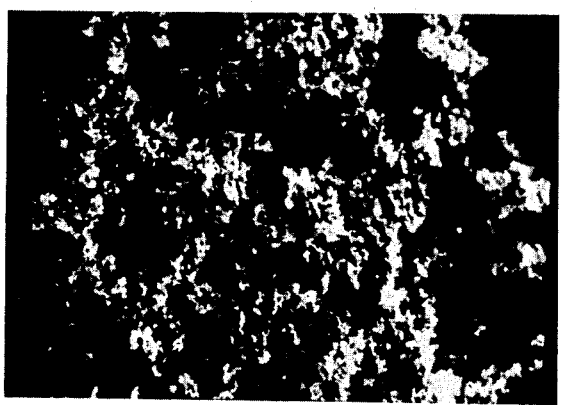
Figure 53:
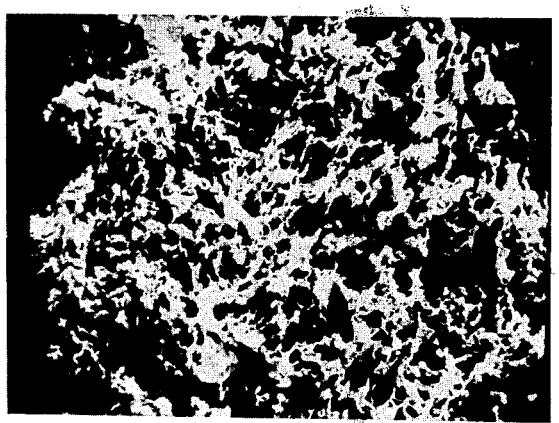
Figure 54:

FIGS. 11 through 13 are photomicrographs at, respectively, 2000X, 2050X and 1950X amplification of still further microporous polypropylene structures of the present invention and illustrate the decreasing cell size as the polypropylene content is increased from the 10% by weight level in FIG. 11, to 20%, and to 30%, in FIGS. 12 and 13, respectively;

FIGS. 14 through 17 are photomicrographs at, respectively, 250X, 2500X, 2500X and 2475X amplification of microporous low density polyethylene structures of the present invention, FIGS. 14 and 15 showing the macro- and microstructure of a microporous polymer containing 20% by weight polyethylene and FIGS. 16 and 17 showing the microstructure with 40% and 70% polyethylene respectively;

FIGS. 18 and 19 are photomicrographs at, respectively, 2100X and 2000X amplification of microporous high density polyethylene structures of the present invention and illustrate the structures at 30% and 70% by weight polyethylene, respectively;

FIGS. 20 and 21 are photomicrographs, at, respectively, 2550X and 2575X amplification of microporous SBR polymers of the present invention and show a homogeneous cellular structure;

FIG. 22 is a photomicrograph at 2400X amplification of a microporous methylpentene polymer;

FIGS. 23 and 24 are photomicrographs at, respectively, 255X and 2550X amplification of a microporous ethyleneacrylic acid copolymer;

FIG. 25 is a photomicrograph at 2500X amplification of a microporous polymer formed from a polyphenylene oxidepolystyrene blend;

FIG. 26 is a photomicrograph at 2050X amplification and illustrates a polystyrene microporous polymer;

FIG. 27 is a photomicrograph at 2000X amplification and showing a polyvinylchloride microporous polymer;

FIGS. 28 and 29 are photomicrographs at 2000X amplification of low density polyethylene microporous polymers and showing the partial masking of the basic structure by the "foliage" mode structure;

FIGS. 20 and 33 are mercury intrusion curves of microporous polypropylene structures of the present invention and illustrating the narrow pore diameter distribution which is characteristic of the polymers of the instant invention;

FIGS. 34 to 40 are mercury intrusion curves of commercial microporous products including "Celgard" polypropylene (FIG. 34), "Amerace A20" and "Amerace A30" polyvinyl chloride (FIGS. 35 and 36 respectively), "Porex" polypropylene (FIG. 37), "Millipore BDWP 29300" cellulose acetate (FIG. 38), "Gelman TCM-200" cellulose triacetate and "Gelman Acropor WA" acrylonitrile-polyvinyl chloride copolymer (FIGS. 39 and 40 respectively);

FIGS. 41 through 43 are mercury intrusion curves of microporous structures made in accordance with U.S. Pat. No. 3,378,507, using polyethylene (FIGS. 41 and 42) and polypropylene (FIG. 43);

FIG. 44 is a mercury intrusion curve of a polyethylene microporous material made in accordance with U.S. Pat. No. 3,310,505;

FIGS. 45 to 46 are photomicrographs of a porous polyethylene product prepared by duplicating Example 2 of U.S. Pat. No. 3,378,507 using an injection molding technique, FIG. 45 (240X amplification) showing the macrostructure and FIG. 46 (2400X amplification) showing the microstructure;

FIGS. 47 to 48 are photomicrographs of a porous polyethylene product prepared by duplicating Example 2 of U.S. Pat. No. 3,378,507 using a compression molding technique, FIG. 47 (195X amplification) showing the macrostructure and FIG. 48 (2000X amplification) showing the microstructure;

FIGS. 49 to 50 are photomicrographs of a porous polypropylene product prepared by duplicating Example 2 of U.S. Pat. No. 3,378,507 using an injection molding technique, FIG. 49 (195X amplification) showing the macrostructure and FIG. 50 (2000X amplification) showing the microstructure;

FIGS. 51 to 52 are photomicrographs of a porous polypropylene product prepared by duplicating Example 2 of U.S. Pat. No. 3,378,507 using a compression molding technique, FIG. 51 (206X amplification) showing the macrostructure and FIG. 52 (2000X amplification) showing the microstructure, and FIGS. 53 to 54 are photomicrographs of a porous polyethylene product prepared by duplicating Example 2 of U.S. Pat. No. 3,310,505, FIG. 53 (205 amplification) showing the macrostructure and FIG. 54 (200X amplification) showing the microstructure.

Figure 55:
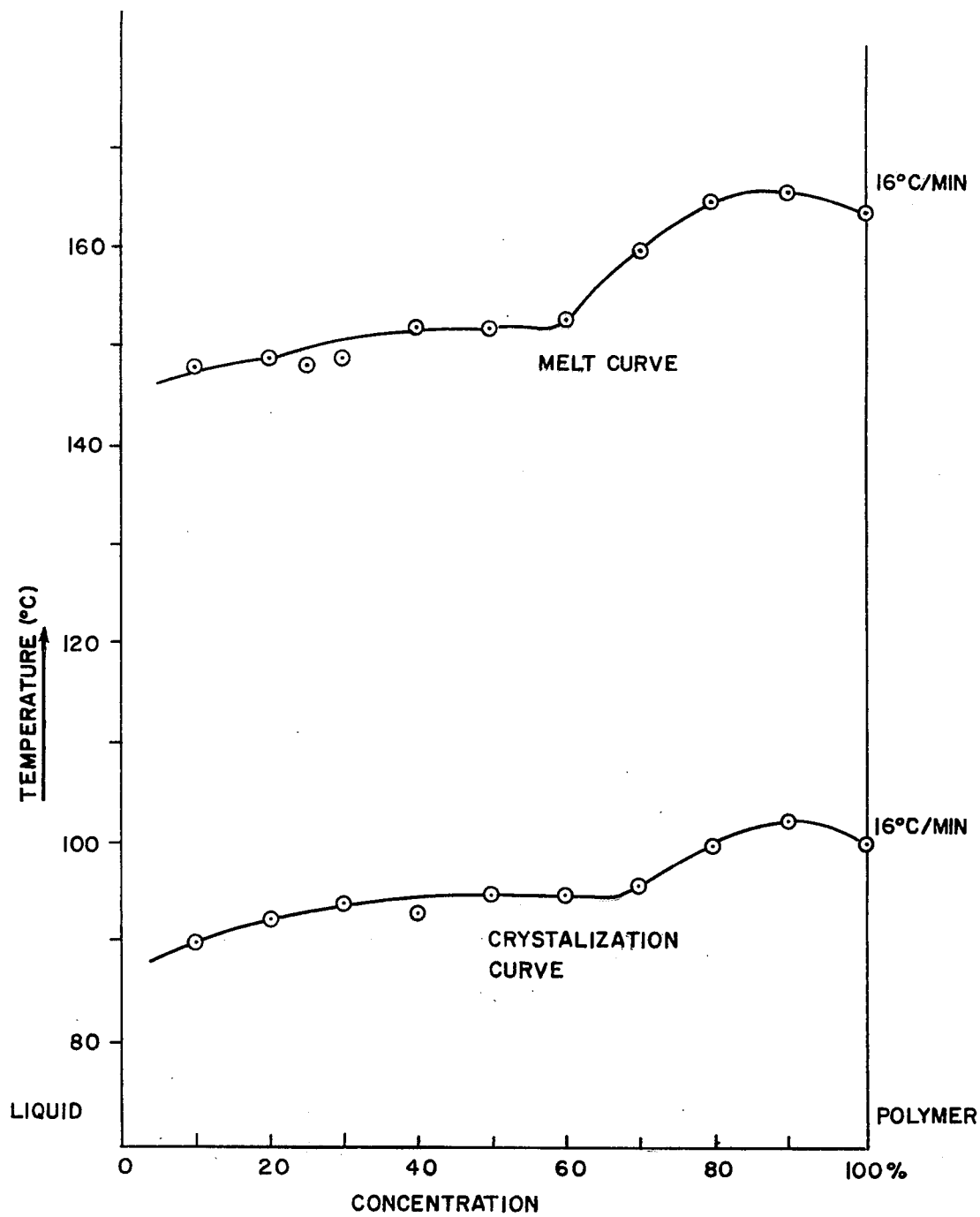

FIG. 55 shows a melt curve and a crystallization curve for a polypropylene and quinoline polymer/liquid system.

Figure 56:
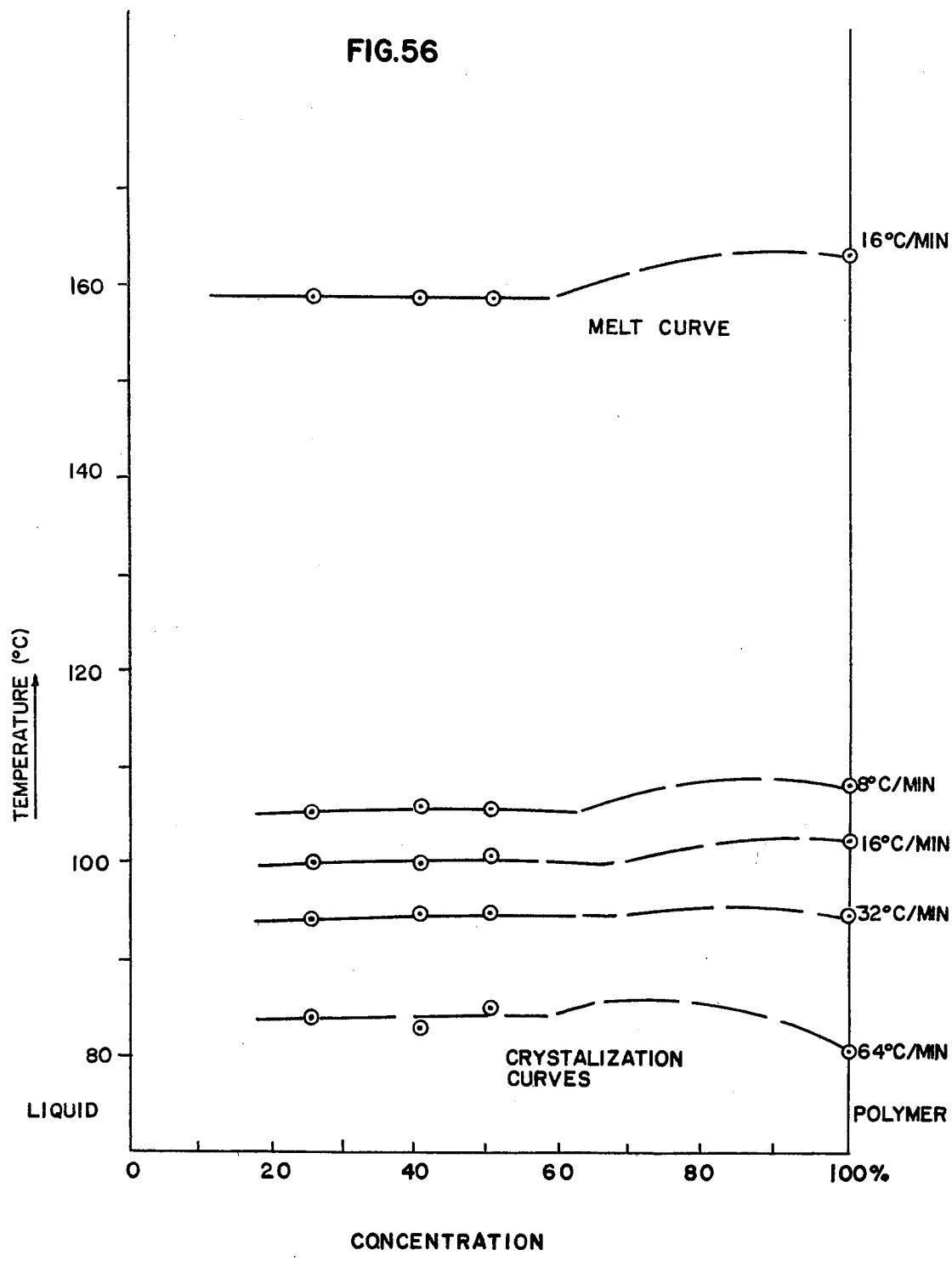

FIG. 56 shows a melt curve and several crystallization curves for a polypropylene and N,N bis(2-hydroxyethyl) tallowamine polymer/liquid system.

Figure 57:
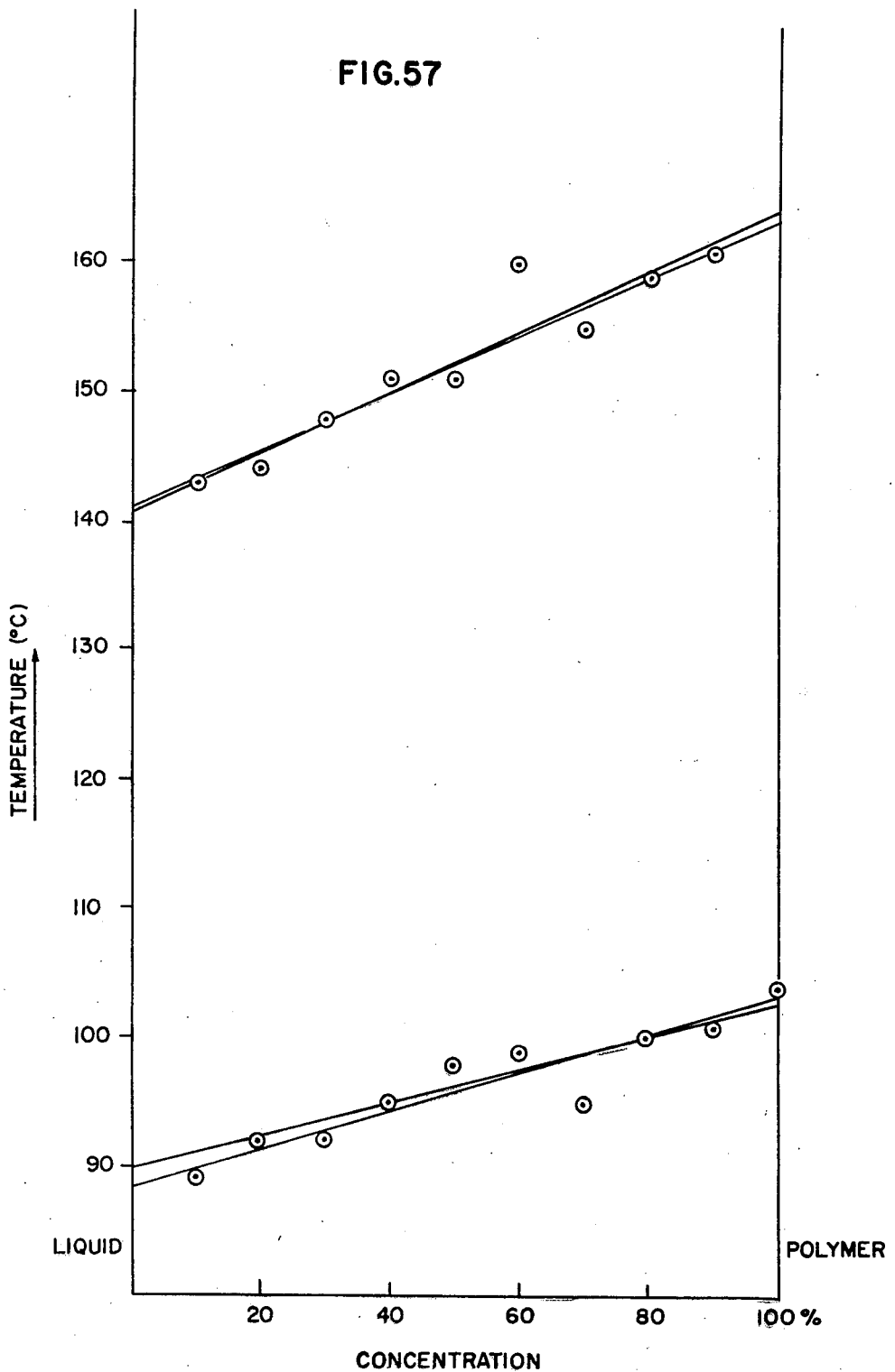

FIG. 57 shows a melt curve and a crystallization curve for a polypropylene and dioctyl phthalate polymer/liquid system, demonstrating a system which is not within the scope of the present invention.

Figure 58:
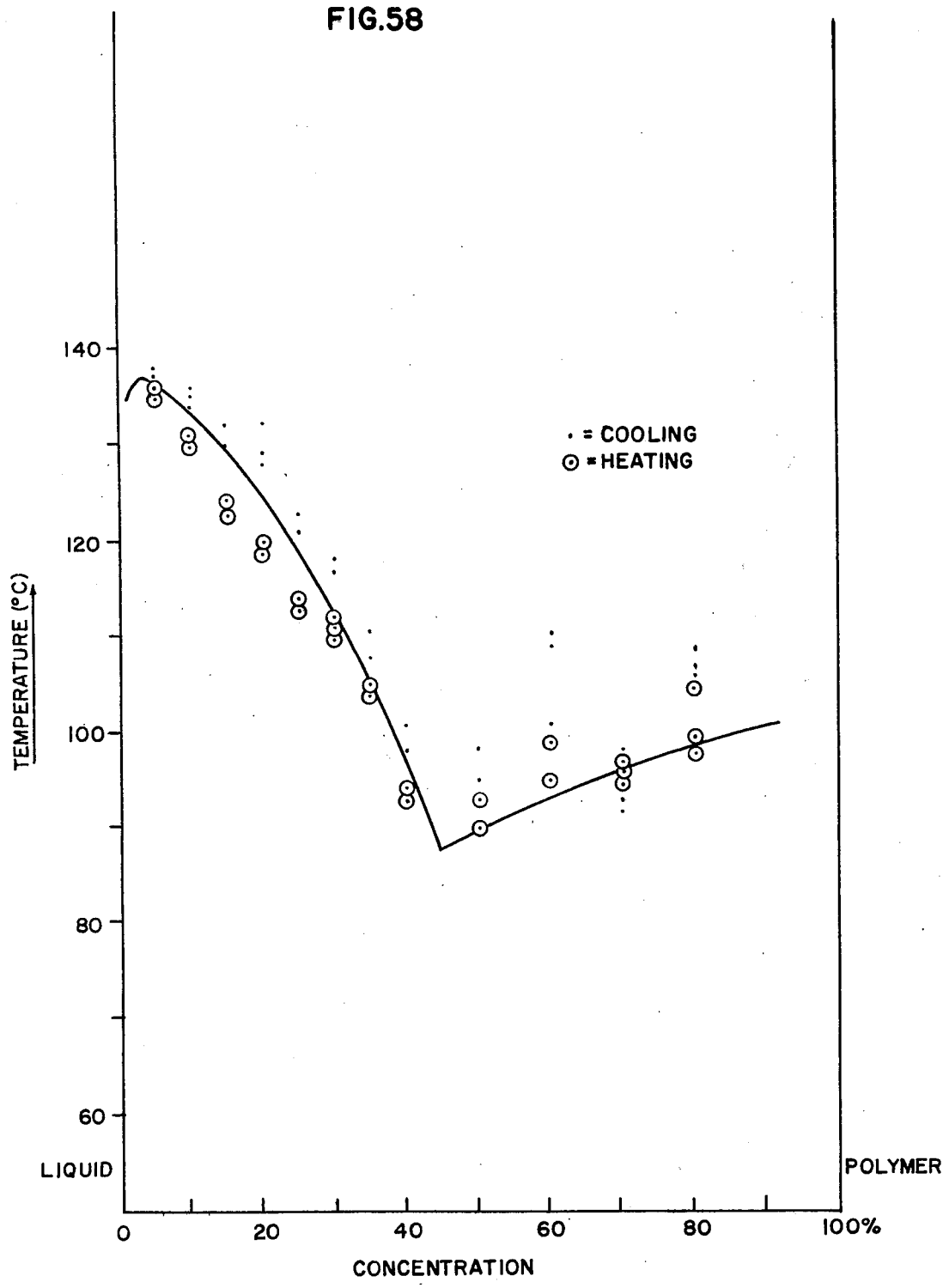

FIG. 58 shows the phase diagram for a low molecular weight polyethylene and diphenyl ether polymer/liquid system, determined at cooling and heating rates of 1° C./minute.

Figure 59:
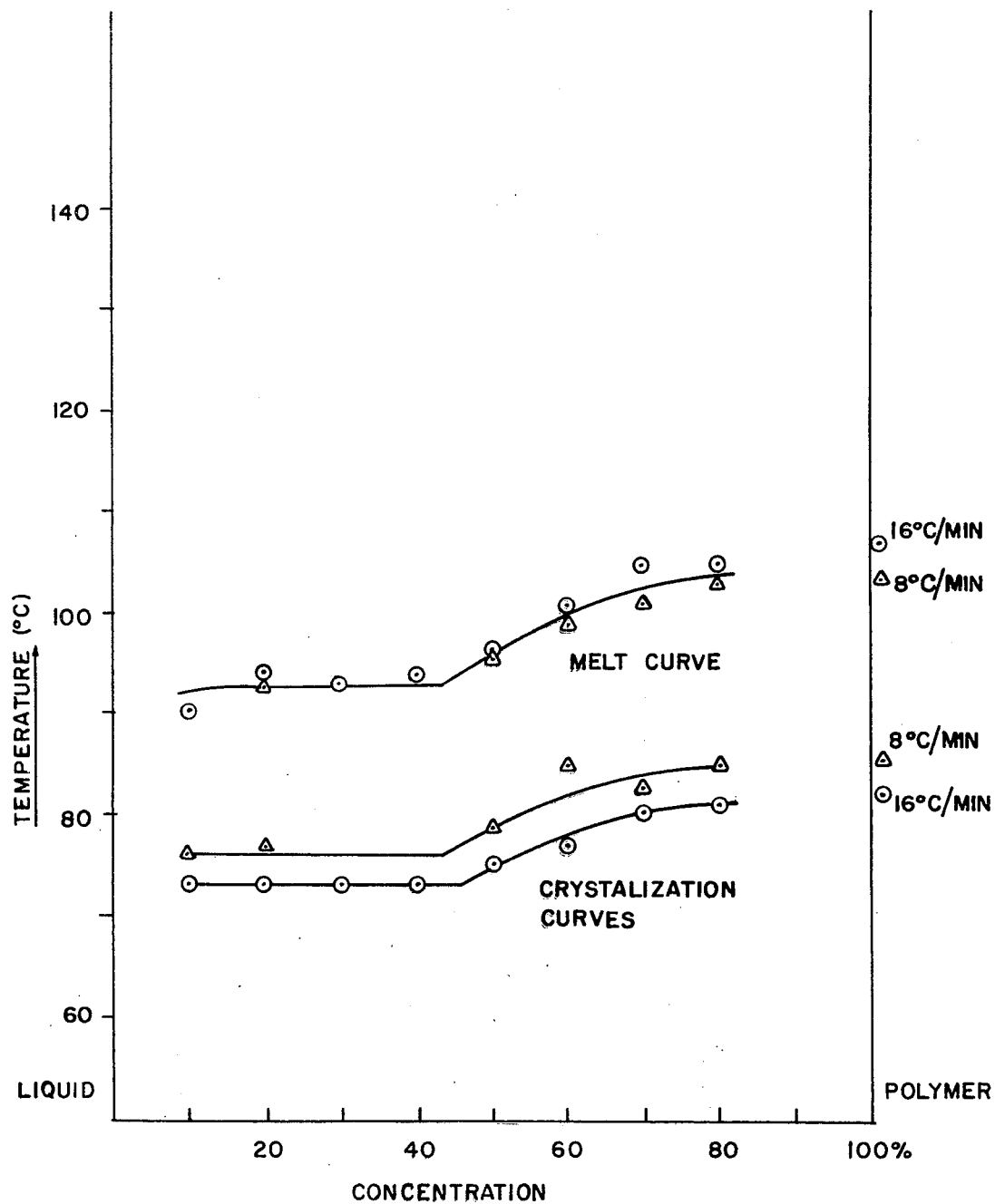

FIG. 59 shows several melt and crystallization curves for a low molecular weight polyethylene and diphenyl ether polymer/liquid system.

Figure 60:
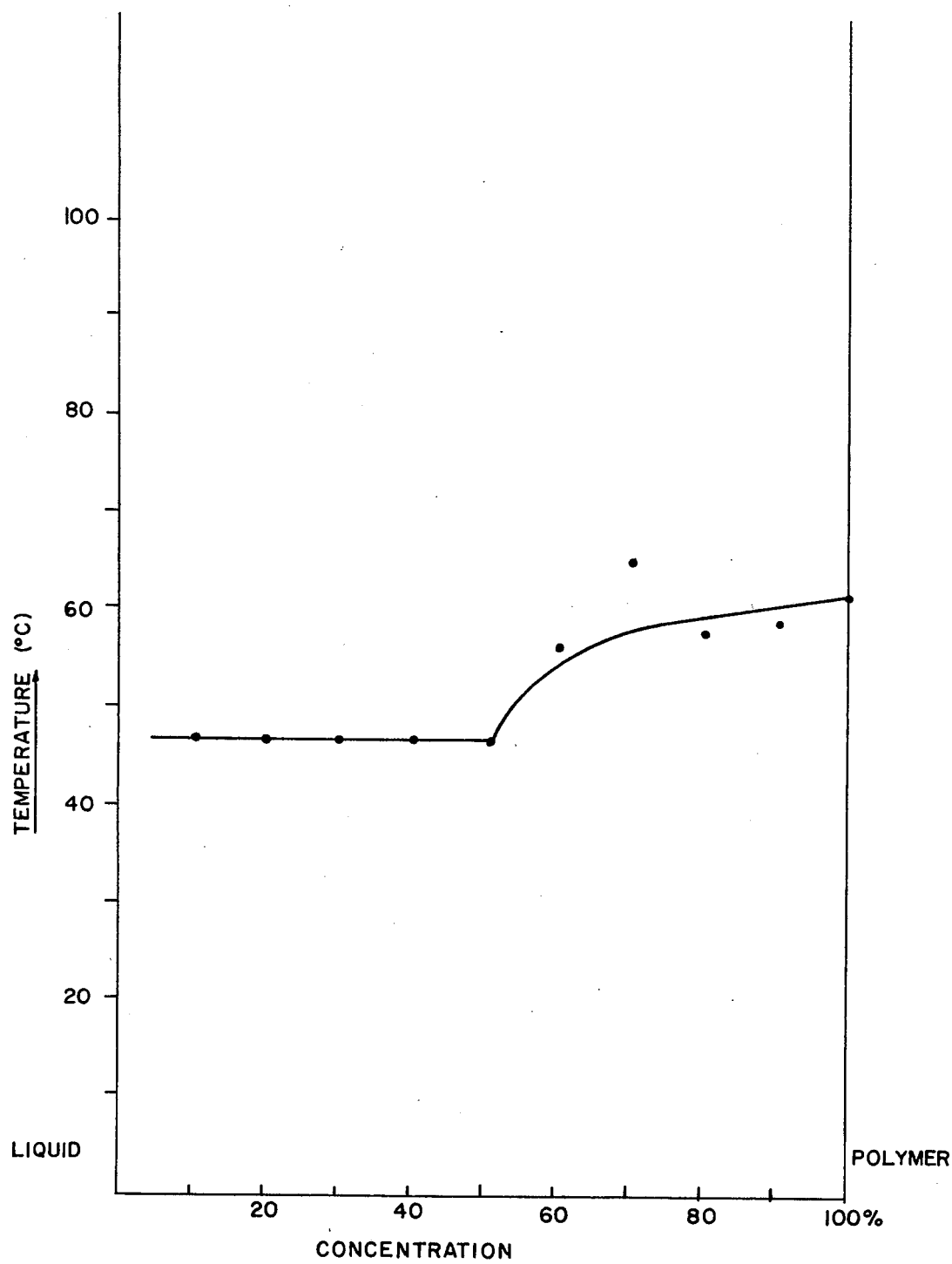

FIG. 60 shows a glass transition curve for a low molecular weight polystyrene and 1-dodecanol polymer/liquid system.

Figure 61:
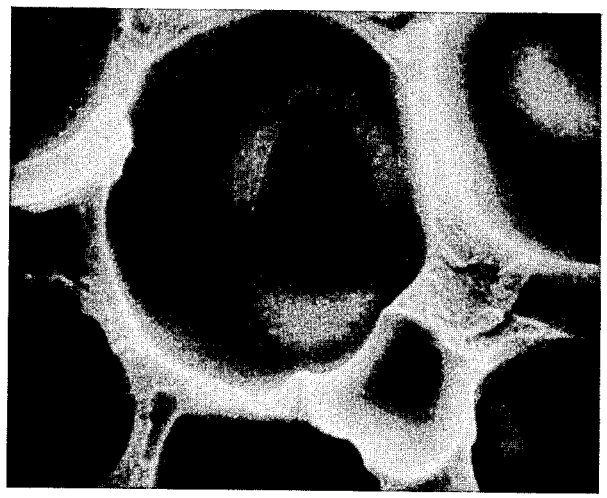

FIG. 61 is a photomicrograph at 5000X amplification of a 70 percent void microporous cellular structure of the present invention, made from polymethylmethacrylate.

Figure 62:
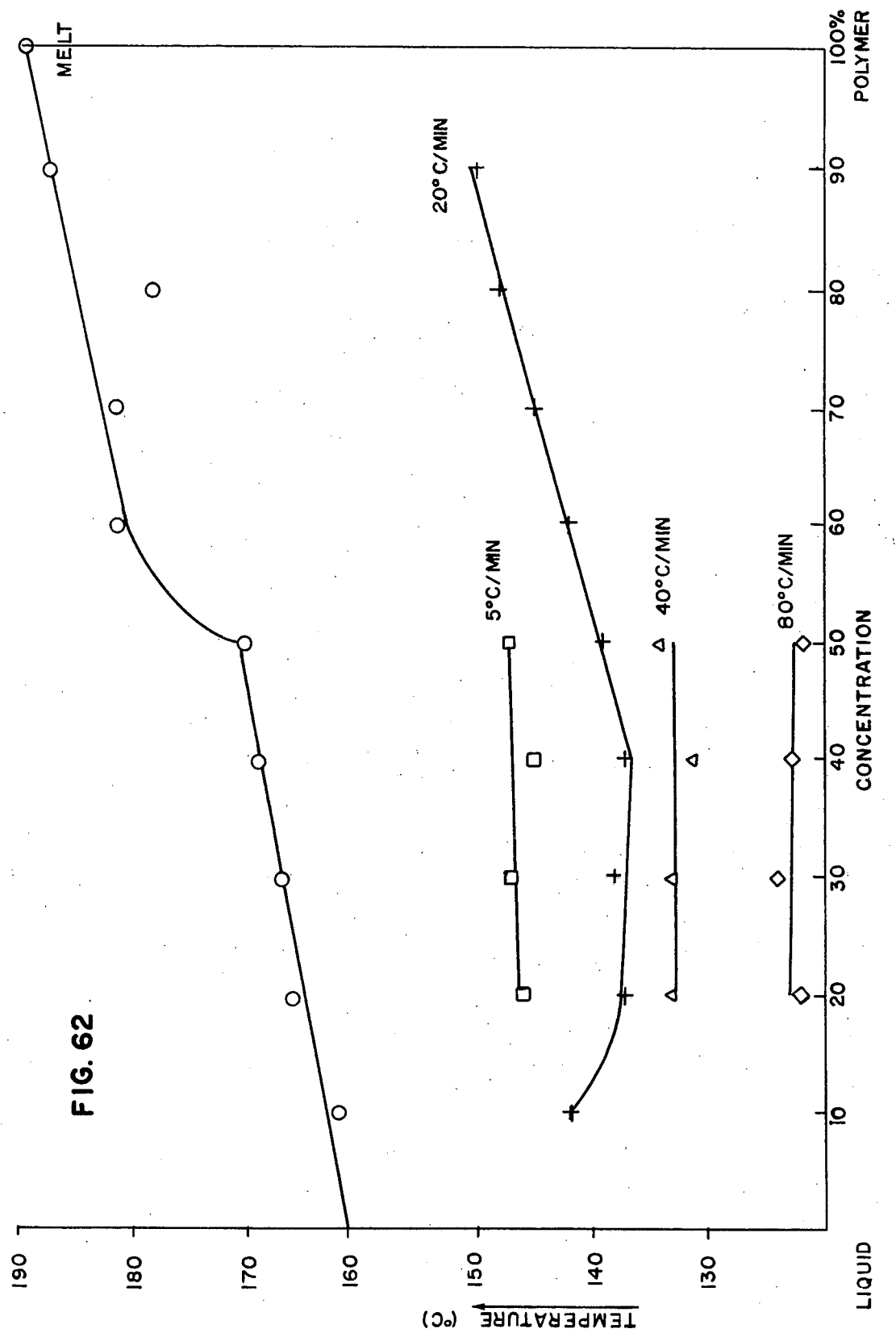

FIG. 62 shows melt and crystallization curves for a Nylon 11 and tetramethylene sulfone polymer/liquid system.

Figure 63:
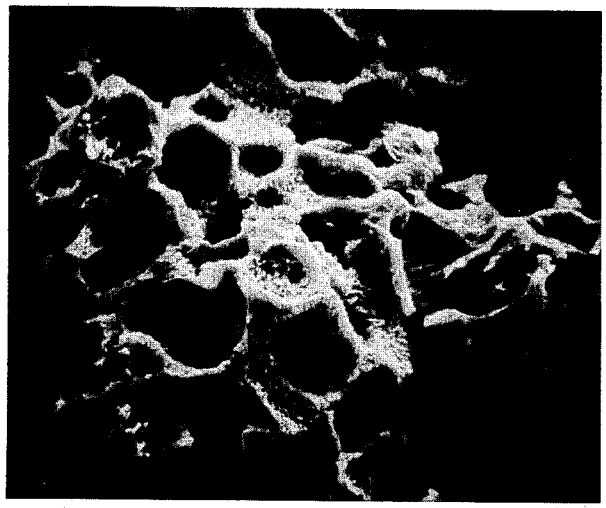

FIG. 63 is a photomicrograph at 2000X amplification of a 70 percent void microporous cellular structure of the present invention, made from Nylon 11.

Figure 64:
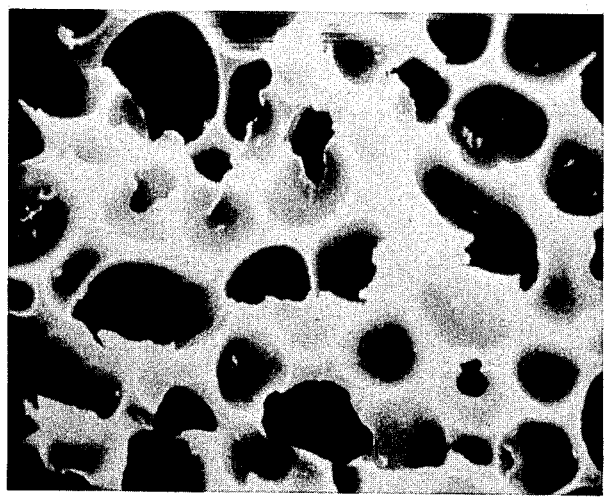

FIG. 64 is a photomicrograph at 2000X amplification of a 70 percent void microporous cellular structure of the present invention, made from polycarbonate.

Figure 65:
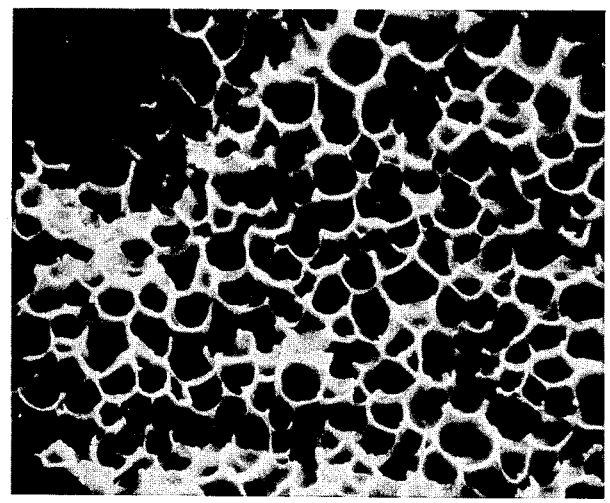

FIG. 65 is a photomicrograph at 2000X amplification of a 70 percent void microporous cellular structure of the present invention, made from polyphenylene oxide.

Figure 66:
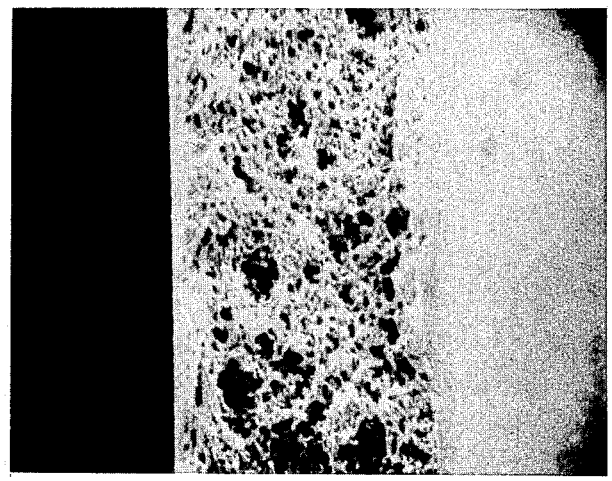
Figure 67:
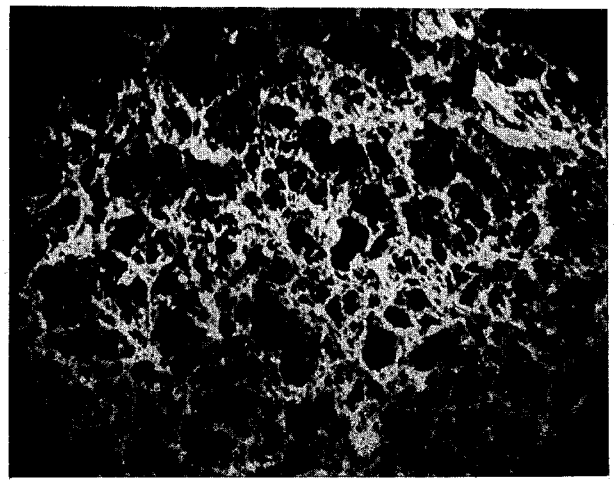

FIGS. 66 and 67 are photomicrographs at 2000X amplification of a 60 percent void and a 75 percent void, respectively, microporous non-cellular structure of the present invention, made from polypropylene.

Figure 68:
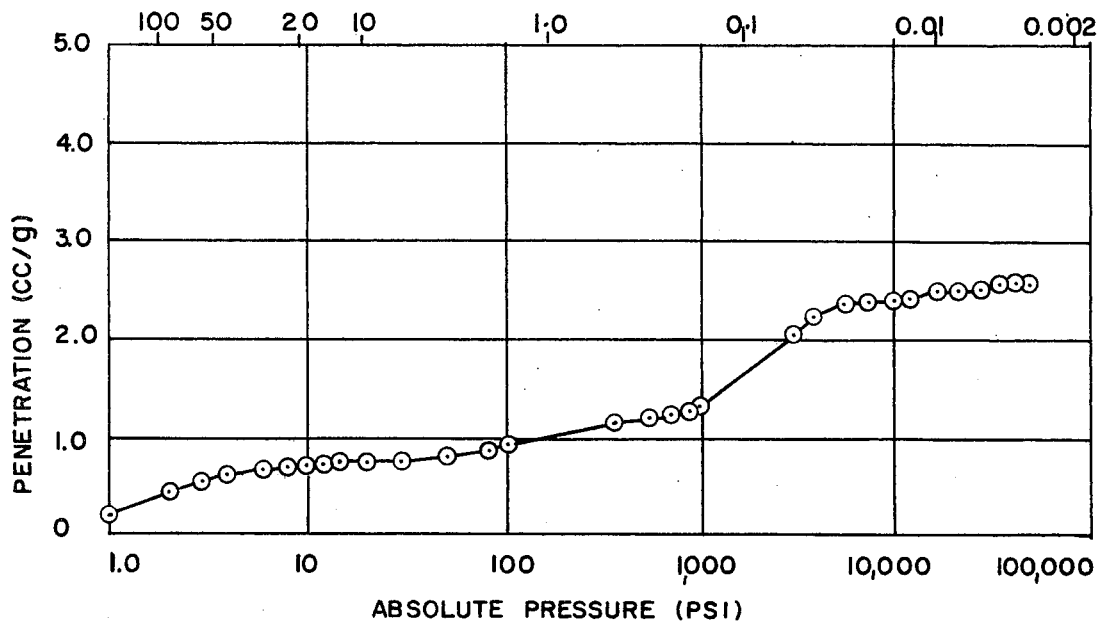
Figure 69:
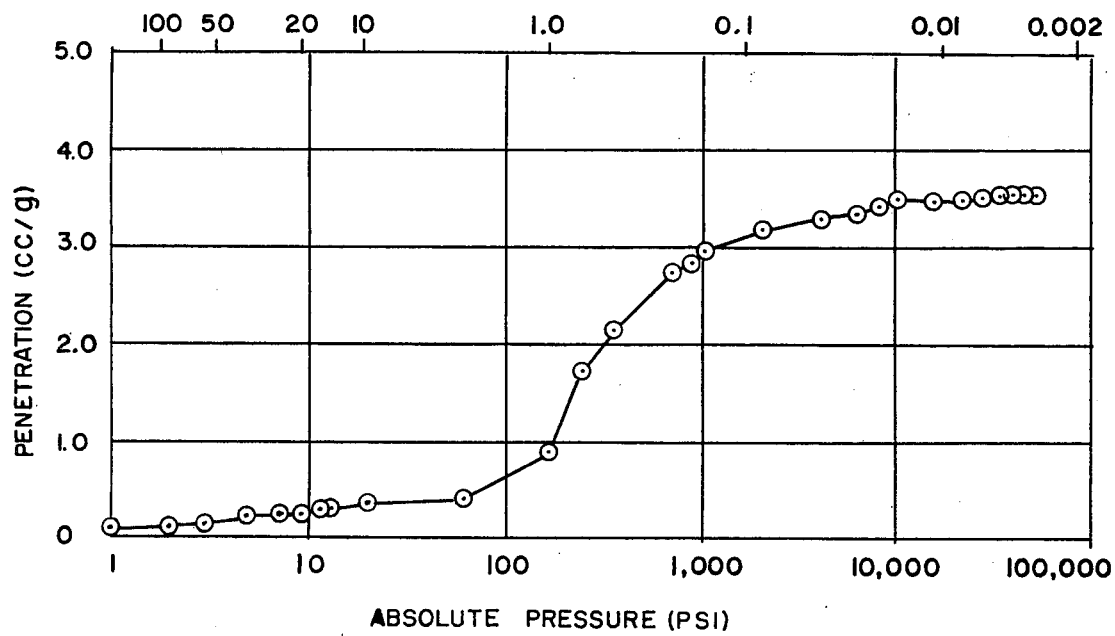

FIGS. 68 and 69 are, respectively, mercury intrusion curves of a 60 percent void and a 75 percent void non-cellular microporous polypropylene structure within the scope of the present invention.

FIG. 70 is a graphical representation of the unique microporous cellular structures of the present invention as compared to certain prior art compositions.

While the invention is susceptible of various modifications and alternative forms, there will be herein described in detail the preferred embodiments. It is to be understood, however, that it is not intended to limit the invention to the specific forms disclosed. On the contrary, it is intended to cover all modifications and alternative forms falling within the spirit and scope of the invention as expressed in the appended claims.

SUMMARY OF THE INVENTION

It has now been discovered that any synthetic thermoplastic polymer may be rendered microporous by first heating said polymer and a compatible liquid, discussed hereinbelow, to a temperature and for a time sufficient to form a homogeneous solution. The so formed solution is then allowed to assume a desired shape and subsequently cooled in said shape at a rate and to a temperature sufficient so that thermodynamic non-equilibrium liquid-liquid phase separation is initiated. As the solution is cooled in the desired shape, no mixing or other shear force is applied while the solution is undergoing the cooling. The cooling is continued so that a solid results. The solid needs only to attain sufficient mechanical integrity to allow it to be handled, without causing physical degradation. Finally, at least a substantial portion of the compatible liquid is removed from the resulting solid to form the desired microporous polymer.

Certain novel microporous olefinic and oxidation polymers of the present invention are characterized by a narrow pore size distribution, as determined by mercury intrusion porosimetry. The narrow pore size distribution may be analytically expressed in terms of a sharpness function "S" which is explained in detail hereinbelow. The "S" values of the olefinic and oxidation polymer of the present invention range from about 1 to about 10. Also, said polymers of the present invention are characterized by average pore sizes which range from about 0.10 to about 5 microns about 0.2 to about 1 micron being preferred. Furthermore, such microporous products are substantially isotropic, and thus have essentially the same cross-sectional configuration when analyzed along any spatial plane.

In another aspect of the present invention the method of preparing microporous polymers is performed so that a mixture comprising a synthetic thermoplastic polymer, especially a polyolefin, an ethylene-acrylic acid copolymer, a polyphenylene oxide-polystyrene blend, or a blend of one or more of the foregoing polymers, and a compatible liquid is heated to a temperature and for a time sufficient to form a homogeneous solution.

The solution is then cooled, thus forming at substantially the same time a plurality of liquid droplets of substantially the same size. The cooling is then continued to solidify the polymer and at least a substantial portion of the liquid is removed from the resulting solid to form the desired cellular polymer structure.

The foregoing method will result in microporous polymer products characterized by a cellular, three-dimensional, void microstructure, i.e.—a series of enclosed cells having substantially spherical shapes and pores or passageways interconnecting adjacent cells. The basic structure is relatively homogeneous with the cells being uniformly spaced throughout the three dimensions, and the interconnecting pores have diameters which are relatively narrow in size distribution as measured by mercury intrusion. For ease of reference, microporous polymers having such a structure will be referred to as "cellular."

A related aspect of this invention provides novel microporous polymer products which behave as solids and contain relatively large amounts of functionally useful liquids such as, for example, polymer additives including flame retardants and the like. In this fashion, useful liquids may obtain the processing advantages of a solid material which may be used directly, as for example, in a master batch. Such products may be formed directly by using a functional liquid as the compatible liquid and not carrying out the removal of the compatible liquid or indirectly by either reloading the microporous polymer after the removal of the compatible liquid or displacing the compatible liquid before removal to incorporate the functional liquid.

DETAILED DESCRIPTION OF THE INVENTION

Broadly, the practice of the process of the instant invention involves heating the desired polymer with an appropriate compatible liquid to form a homogeneous solution, cooling said solution in an appropriate manner to form a solid material and subsequently extracting the liquid to form a microporous material. The considerations involved in practicing the instant invention will be described in detail hereinbelow.

SELECTION OF THE POLYMER

As indicated, the present invention surprisingly affords a technique for rendering any synthetic thermoplastic polymer microporous. Thus, the process of the present invention applies to olefinic polymers, condensations polymers, and oxidation polymers.

Exemplary of the useful non-acrylic polyolefins are low density polyethylene, high density polyethylene, polypropylene, polystyrene, polyvinylchloride, acrylonitrile-butadiene-styrene terpolymers, styrene-acrylonitrile copolymer, styrene butadiene copolymers, poly (4-methyl-pentene-1), polybutylene, polyvinylidene chloride, polyvinyl butyral, chlorinated polyethylene, ethylene-vinyl acetate copolymers, polyvinyl acetate, and polyvinyl alcohol.

Useful acrylic polyolefins include polymethyl-methacrylate, polymethyl-acrylate, ethylene-acrylic acid copolymers, and ethylene-acrylic acid metal salt copolymers.

Polyphenylene oxide is representative of the oxidation polymers which may be utilized. The useful condensation polymers include polyethylene terephthalate, polybutylene terephthalate, Nylon 6, Nylon 11, Nylon 13, Nylon 66, polycarbonates and polysulfone.

SELECTION OF THE COMPATIBLE LIQUID

Thus, to practice the present invention one need only first choose the synthetic thermoplastic polymer which is to be rendered microporous. Having selected the polymer, the next procedure is the selection of the appropriate compatible liquid and the relative amounts of polymer and liquid to be utilized. Of course blends of one or more polymers may be utilized in the practice of the present invention. Functionally, the polymer and liquid are heated with stirring up to the temperature required to form a clear, homogeneous solution. If a solution cannot be formed at any liquid concentration, then the liquid is inappropriate and cannot be utilized with that particular polymer.

Because of the selectivity, absolute predictability for predetermining the operability of a particular liquid with a particular polymer is not possible. However, some useful general guidelines can be set forth. Thus when the polymer involved is non-polar, non-polar liquids with similar solubility parameters at the solution temperature are more likely to be useful. When such parameters are not available, one may refer to the more readily available room temperature solubility parameters, for general guidance. Similarly, with polar polymers, polar organic liquids with similar solubility parameters should be initially examined. Also, the relative polarity or non-polarity of the liquid should be matched with the relative polarity or non-polarity of the polymer. In addition, with hydrophobic polymers, useful liquids will typically have little or no water solubility. On the other hand, polymers which tend to be hydrophilic will generally require a liquid having some water solubility.

With respect to appropriate liquids, particular species of various types of organic compounds have been found useful, including aliphatic and aromatic acids, aliphatic, aromatic and cyclic alcohols, aldehydes, primary and secondary amines, aromatic and ethoxylated amines, diamines, amides, esters and diesters, ethers, ketones and various hydrocarbons and heterocycles. It should, however, be noted that the concept is quite selective. Thus, for example, not all saturated aliphatic acids will be useful; and, further, not all liquids useful for high density polyethylene will necessarily be useful for, as an example, polystyrene.

As will be appreciated, the useful proportions of polymer and liquid for any particular system can readily be developed from an evaluation of the parameters which will be discussed subsequently.

Where blends of one or more polymers are used, as should be understood, useful liquids must typically be operable with all of the polymers included. It may however be possible for the polymer blend to have characteristics such that the liquid need not be operable with all polymers used. As one example, where one or more polymeric constituents are present in such relatively small amounts as to not significantly affect the properties of the blend, the liquid employed need only be operable with the principal polymer or polymers.

Also, while most useful materials are liquids at ambient temperatures, materials which are solid at room temperature may be employed so long as solutions can be formed with the polymer at elevated temperatures and the material does not interfere with the formation of the microporous structure. More specifically, a solid material may be used so long as phase separation occurs by liquid-liquid separation rather than liquid-solid separation during the cooling step which will hereinafter be discussed. The amount of liquid used can be, in general, varied from about 10 to about 90%.

As presently discussed any synthetic thermoplastic polymer may be employed so long as the liquid selected forms a solution with the polymer and the concentration yields a continuous polymer phase upon separation during cooling, as will be discussed in more detail hereinafter. So that one may appreciate the range of operable polymer and liquid systems, a brief summary of some of such systems may be useful.

In forming microporous polymers from polypropylene, alcohols such as 2-benzylamino-1-propanol and 3-phenyl-1-propanol; aldehydes such as salicylaldehyde; amides such as N,N-diethyl-m-toluamide; amines such as N-hexyl diethanolamine, N-behenyl diethanol amine, N-coco-diethanolamine, benzyl amine, N,N-bis-$\beta$-hydroxyethyl cyclohexyl amine, diphenyl amine and 1,12- diamino dodecane; esters such as methyl benzoate, benzyl benzoate, phenyl salicylate, methyl salicylate and dibutyl phthalate; and ethers such as diphenyl ether, 4-bromodiphenyl ether and dibenzyl ether have been found useful. In addition, halocarbons such as 1,1,2,2-tetrabromoethane and hydrocarbons such as trans-stilbene and other alkyl/aryl phosphites are also useful as are ketones such as methyl nonyl ketone.

In forming microporous polymers from high density polyethylene, a saturated aliphatic acid such as decanoic acid, primary saturated alcohols such as decyl alcohol, and 1-dodecanol, secondary alcohols such as 2-undecanol and 6-undecanol, ethoxylated amines such as N-lauryldiethanolamine, aromatic amines such as N,N-diethylaniline, diesters such as dibutyl sebacate and dihexyl sebacate and ethers such as diphenyl ether and benzyl ether have been found useful. Other useful liquids include halogenated compounds such as octabromodiphenyl, hexabromobenzene and hexabromocyclodecane, hydrocarbons such as 1-hexadecane, diphenylmethane and naphthalene, aromatic compounds such as acetophenonone and other organic compounds such as alkyl/aryl phosphites, and quinoline and ketones such as methylnonyl ketone.

To form microporous polymers from low density polyethylene, the following liquids have been found useful: saturated aliphatic acids including hexanoic acid, caprylic acid, decanoic acid, undecanoic acid, lauric acid, myristic acid, palmitic acid and stearic acid, unsaturated aliphatic acids including oleic acid and erucic acid, aromatic acids including benzoic acid, phenyl stearic acid, polystearic acid and xylyl behenic acid and other acids including branched carboxylic acids of average chain lengths of 6, 9, and 11 carbons, tall oil acids and rosin acid, primary saturated alcohols including 1-octanol, nonyl alcohol, decyl alcohol, 1-decanol, 1-dodecanol, tridecyl alcohol, cetyl alcohol and 1-heptadecanol, primary unsaturated alcohols including undecylenyl alcohol and oleyl alcohol, secondary alcohols including 2-octanol, 2-undecanol, dinonyl carbinol and diundecyl carbinol and aromatic alcohols including 1-phenyl ethanol, 1-phenyl-1-pentanol, nonyl phenyl, phenylstearyl alcohol and 1-naphthol. Other useful hydroxyl-containing compounds include polyoxyethylene ethers of oleyl alcohol and a polypropylene glycol having a number average molecular weight of about 400. Still further useful liquids include cyclic alcohols such as 4, t-butyl cyclohexanol and methanol, aldehydes including salicyl aldehyde, primary amines such as octylamine, tetradecylamine and hexadecylamine, secondary amines such as bis-(1-ethyl-3-methyl pentyl) amine and ethoxylated amines including N-lauryl diethanolamine, N-tallow diethanol-amine, N-stearyl diethanol-amine and N-coco diethanolamine.

Additional useful liquids comprise aromatic amines including N-sec-butylaniline, dodecylaniline, N,N-dimethylaniline, N,N-diethylaniline, p-toluidine, N-ethyl-o-toluidine, diphenylamine and aminodiphenylmethane, diamines including N-erucyl-1,3-propane diamine and 1,8-diamino-p-methane, other amines including branched tetramines and cyclodecylamine, amides including cocoamide, hydrogenated tallow amide, octadecylamide, eruciamide, N,N-diethyl toluamide and N-trimethylopropane stearamide, saturated aliphatic esters including methyl caprylate, ethyl laurate, isopropyl myristate, ethyl palmitate, isopropropyl palmitate, methyl stearate, isobutyl stearate and tridecyl stearate, unsaturated esters including stearyl acrylate, butyl undecylenate and butyl oleate, alkoxy esters including butoxyethyl stearate and butoxyethyl oleate, aromatic esters including vinyl phenyl stearate, isobutyl phenyl stearate, tridecyl phenyl stearate, methyl benzoate, ethyl benzoate, butyl benzoate, benzyl benzoate, phenyl laurate, phenyl salicylate, methyl salicylate and benzyl acetate and diesters including dimethyl phenylene distearate, diethyl phthalate, dibutyl phthalate, di-iso-octyl phthalate, dicapryl adipate, dibutyl sebacate, dihexyl sebacate, di-iso-octyl sebacate, dicapryl sebacate and dioctyl maleate. Yet other useful liquids comprise polyethylene glycol esters including polyethylene glycol (having a number of average molecular weight of about 400), diphenylstearate, polyhydroxylic esters including castor oil (triglyceride), glycerol monostearate, glycerol monooleate, glycol distearate glycerol dioleate and trimethylol propane monophenylstearate, ethers including diphenyl ether and benzyl ether, halogenated compounds including hexachlorocyclopentadiene, octabromobiphenyl, decabromodiphenyl oxide and 4-bromodiphenyl ether, hydrocarbons including 1-nonene, 2-nonene, 2-undecene, 2-heptadecene, 2-nonadecene, 3-eicosene, 9-nonadecene, diphenylmethane, triphenylmethane and trans-stilbene, aliphatic ketones including 2-heptanone, methyl nonyl ketone, 6-undecanone, methylundecyl ketone, 6-tridecanone, 8-pentadecanone, 11-pentadecanone, 2-heptadecanone, 8-heptadecanone, methyl heptadecyl ketone, dinonyl ketone and distearyl ketone, aromatic ketones including acetophenone and benzophenone and other ketones including xanthone. Still further useful liquids comprise phosphorous compounds including trixylenyl phosphate, polysiloxanes, Muget hyacinth (An Merigenaebler, Inc), Terpineol Prime No. 1 (Givaudan-Delawanna, Inc), Bath Oil Fragrance #5864 K (International Flavor & Fragrance, Inc), Phosclere P315C (organophosphite), Phosclere P576 (organophosphite), styrenated nonyl phenol, quinoline and quinalidine.

To form microporous polymer products with polystyrene, useful liquids include tris-halogenated propylphosphate, aryl/alkyl phosphites, 1,1,2,2, tetrabromoethane, tribromoneopentylalcohol, 40% Voranol C.P. 3000 polyol and tribromoneopentyl alcohol 60%, tris-$\beta$-chloroethylphosphate, tris (1,3-dichloroisopropyl) phosphate, tri-(dichloropropyl) phosphate, dichlorobenzene, and 1-dodecanol.

In forming microporous polymers using polyvinyl chloride, useful liquids comprise aromatic alcohols including methoxy benzyl alcohol, 2-benzylamino-1-propanol, and other hydroxyl-containing liquids including 1,3-dichloro-2-propanol. Still other useful liquids comprise halogenated compounds including Firemaster T33P (tetrabromophthalic diester), and aromatic hydrocarbons including trans-stilbene.

In addition, in accordance with the present invention, microporous products have been made from other polymers and copolymers and blends. Thus, to form microporous products from styrene-butadiene copolymers, useful liquids include decyl alcohol, N-tallow diethanol amine, N-coco diethanol amine and diphenyl amine. Useful liquids for forming microporous polymers from ethylene-acrylic acid copolymer salts include N-tallow diethanolamine, N-coco diethanolamine, dibutyl phthalate and diphenyl ether. Microporous polymer products using high impact polystyrene can be formed by employing as liquids, hexabromobiphenyl and alkyl-/aryl phosphites. With "Noryl" polyphenylene oxide-polystyrene blends (General Electric Company), microporous polymers can be made utilizing N-coco diethanol amine, N-tallow diethanolamine, diphenylamine, dibutyl phthalate and hexabromophenol. Microporous polymers from blends of low density polyethylene and chlorinated polyethylene can be made by utilizing 1-dodecanol, diphenyl ether and N-tallow diethanolamine. Utilizing 1-dodecanol as the liquid, microporous polymer products can be made from the following blends: polypropylene-chlorinated polyethylene, high density polyethylene-chlorinated polyethylene, high density polyethylene-polyvinyl chloride and high density polyethylene and acrylonitrile-butadiene-styrene (ABS) terpolymers. To form microporous products from polymethylmethacrylate, 1-4,butanediol and lauric acid have been found to be useful. Microporous Nylon 11 may be made utilizing ethylene carbonate, 1,2-propylene carbonate, or tetramethylene sulfone. Also, menthol may be utilized to form microporous products from polycarbonate.

SELECTION OF THE CONCENTRATIONS OF POLYMER AND LIQUID

The determination of the amount of the liquid used is obtained by reference to the binodial and spinodal curves for the system, illustrative curves being set forth in FIG. 1. As shown therein, $T_m$ represents the maximum temperature of the binodial curve (i.e.-the maximum temperature of the system at which binodial decomposition will take place), $T_{ucs}$ represents the upper critical solution temperature (i.e.-the maximum temperature at which spinodal decomposition will take place), $\phi_m$ represents the polymer concentration at $T_m$, $\phi_c$ denotes the critical concentration and $\phi_x$ represents the polymer concentration of the system needed to obtain the unique microporous polymer structures of the present invention. Theoretically, $\phi_m$ and $\phi_c$ should be virtually identical; however, as is known, due to molecular weight distributions of commercially available polymers, $\phi_c$ may be about 5% by weight or so greater than the value of $\phi_m$. To form the unique microporous polymers of the present invention, the polymer concentration utilized for a particular system $\phi_x$, must be greater than $\phi_c$. If the polymer concentration is less than $\phi_c$, the phase separation which will occur as the system is cooled will constitute a continuous liquid phase with a discontinuous polymer phase. On the other hand, utilizing the proper polymer concentration will insure that the continuous phase, which will be formed upon cooling to the phase separation temperature, will be the polymer phase, as is required to obtain the unique microcellular structures of the present invention. Likewise, as will be apparent, the formation of a continuous polymer phase upon phase separation requires that a solution be initially formed. When the process of the present invention is not followed and a dispersion is initially formed, the resulting microporous product is similar to that achieved by sintering together polymer particles.

Accordingly, as will be appreciated, the applicable polymer concentration or amount of liquid which may be utilized, will vary with each system. Suitable phase diagram curves for several systems have already been developed. However, if an appropriate curve is not available, this can be readily developed by known techniques. For example, a suitable technique is set forth in Smolders, van Aartsen and Steenbergen, Kolloid—Z. u. Z. Polymere, 243, 14 (1971).

A more general graph of temperature vs. concentration for a hypothetical polymer-liquid system is given by FIG. 1A. The portion of the curve from $\gamma$ to $\alpha$ represents thermodynamic equilibrium liquid—liquid phase separation. The portion of the curve from $\alpha$ to $\beta$ represents equilibrium liquid-solid phase separation, which will be recognized as the normal freezing point depression curve of a hypothetical liquid-polymer system. The upper shaded areas represents an upper liquid/liquid immiscibility which may be present in some systems. The dotted line represents the lowering of crystallization temperature as a consequence of cooling at a rate sufficient to achieve thermodynamic non-equilibrium liquid-liquid phase separation. The flat portion of the crystallization vs. composition curve defines a useable composition range which is a function of the cooling rate employed, as will be discussed in more detail.

Thus, for any given cooling rate, one may plot the crystallization temperature vs. percentage resin or compatible liquid and in such a manner determine the liquid/polymer concentration ranges which will yield the desirable microporous structures at the given cooling rate. For crystalline polymers, the determination of the useable concentration range via the plotting of the aforementioned crystallization curve is a viable alternative to determining a phase diagram, as shown in FIG. 1. As an example of the foregoing, one may refer to FIG. 55 which is a plot of temperature vs. polymer/liquid concentration showing the melt curve at a heating rate of 16° C. per minute, and crystallization curve for polypropylene and quinoline over a broad concentration range. As may be seen by reference to the crystallization curve, at a cooling rate of 16° C. per minute, the appropriate concentration range extends from about 20 percent polypropylene to about 70 percent polypropylene.

FIG. 56 is a graph of temperature versus polymer/liquid composition for polypropylene and N,N-bis (2-hydroxyethyl) tallowamine. The upper curve is a plot of the melt curve at a heating rate of 16° C. per minute. The lower curves, in descending order, are plots of the crystallization curves at cooling rates of 8° C., 16° C., 32° C., and 64° C., per minute. The curves demonstrate two concurrent phenomena which occur when the cooling rate is increased. First, the flat portion of the curve demonstrating a relative stable temperature of crystallization across a broad concentration range, is lowered with increased cooling rate showing that the faster the rate of cooling, the lower the actual crystallization temperature.

The second observable phenomenon is the change in the slope of the crystallization curve which occurs with changes in the rate of cooling. Thus, it appears that the flat region of the crystallization curve is expanded when the cooling rate is increased. Accordingly, one may assume that by increasing the rate of cooling, one may correspondingly increase the operable concentration range for forming the microporous structures of the present invention and for practicing the processes of the instant invention. From the foregoing it is apparent that to determine the operable concentration ranges for a given system, one need only prepare a few representative concentrations of polymer/liquid and cool the same at some desired rate. After the crystallization temperatures have been plotted, the operable range of concentrations will be quite apparent.

FIG. 57 is a graph of temperature versus polymer/liquid concentration for polypropylene and dioctyl phthalate. The upper curve represents the melt curve for the system over a range of concentrations and the lower curve represents the crystallization curve over the same concentration range. As the crystallization curve does not exhibit any flat region over which the crystallization temperature remains substantially constant for a range of concentration, one would not expect the polypropylene/dioctyl phthalate system to be capable of forming microporous structures, and, indeed, it does not.

To appreciate the excellent correlation between the phase diagram method of determining operable concentration ranges of polymer and liquid and the crystallization method of making such a determination, one may refer to FIGS. 58 and 59. FIG. 58 is a phase diagram for a low molecular weight polyethylene and diphenyl ether polymer/liquid system, determined by a conventional light scattering technique utilizing a thermally controlled vessel. From the phase diagram of FIG. 58, it appears that $T_m$ is at about 135° C. and $\phi_m$ is at about 7 percent polymer. Furthermore, it is apparent that at about 45 percent polymer concentration, the cloud point curve intersects the freezing point depression curve, thus indicating an operable concentration range of about 7 percent polymer to about 45 percent polymer.

One may compare the operable range determined from FIG. 58 to the range determinable from FIG. 59 which shows melt curves of the same system at heating rates of 8° C. and 16° C./minute and crystallization curves for said system at cooling rates of 8° C. and 16° C./minute. From the crystallization curves it appears that the substantially flat portion thereof extends from somewhat below 10 percent polymer concentration to approximately 42–45 percent polymer, depending on the cooling rate. Thus, the results obtained from the crystallization curves agree surprisingly well with the results obtained from the cloud point phase diagram.

For non-crystalline polymers it is believed that one may refer to a temperature vs. concentration plot of the glass transition temperature, as an alternative to referring to a phase diagram such as that of FIG. 1. Thus, FIG. 60 is a graph of temperature vs. concentration for the glass transition temperature of low molecular weight polystyrene, supplied by Pennsylvania Industrial Chemical Corporation under the designation Piccolastic D-125, and 1-dodecanol, at various concentration levels.

From FIG. 60 it is apparent that from about 8 percent polymer to about 50 percent polymer, the glass transition temperature for the polystyrene/1-dodecanol is essentially constant. It has therefore been proposed that the concentrations along the substantially flat portion of the glass transition curve would be operable in the practice of the instant invention, analagous to the flat portion of the crystallization curves previous discussed. It thus appears that a viable alternative to determining the phase diagram for non-crystalline polymer systems is to determine the glass transition curve and to operate in the substantially flat region of such a curve.

In all of the foregoing FIGS., the crystallization temperatures were determined with a DSC-2, differential scanning calorimeter, manufactured by Perkin-Elmer, or comparable equipment. Further effects of cooling rates as the practice on the present invention will be discussed hereinbelow.

After one has chosen the desired synthetic thermoplastic polymer, the compatible liquid and the potentially operable concentration range, one needs to choose, for example, the actual concentration of polymer and liquid which will be utilized. In addition to considering, for example, the theoretically possible concentration range, other functional considerations should be employed in determining the proportions used for a particular system. Thus, insofar as the maximum amount of liquid which should be utilized is concerned, the resulting strength characteristics must be taken into account. More particularly, the amount of liquid used should accordingly allow the resulting microporous structure to have sufficient minimum "handling strength" to avoid collapse of the microporous or cellular structure. On the other hand, the selection of the maximum amount of resin, viscosity limitations of the particular equipment utilized may dictate the tolerable maximum polymer or resin content. Moreover, the amount of polymer used should not be so great as to result in closing off the cells or other areas of microporosity.

The relative amount of liquid used will also, to some extent, be dependent upon the desired effective size of the microporosity, as, for example, the particular cell and pore size requirements for the ultimate application involved. Thus, for example, the average cell and pore size tend to increase somewhat with increasing liquid content.

In any event, the utility of a liquid and the operable concentration thereof, for a particular polymer, can be readily determined by experimentally using the liquid as has been described.

The parameters previously discussed should, of course, be followed. Indeed, as should be appreciated, blends of two or more liquids can be used; and the utility of a particular blend can be ascertained as described herein. Also, while a particular blend may be useful, one or more of the liquids may conceivably be unsuitable individually.

As may be appreciated, the particular amount of liquid employed will likewise be often dictated by the particular end use application. As illustrative examples of specific examples, utilizing high density polyethylene and N,N-bis(2-hydroxyethyl) tallowamine, useful microporous products can be made by utilizing, by weight, from about 30 to about 90% amine, 30 to 70 being preferred. With low density polyethylene and the same amine, the amount of liquid can usefully be varied within the range from about 20 to 90%, 20 to 80 being preferred. In contrast, when diphenylether is used as the liquid, useful low density polyethylene systems contain no more than about 80% of the liquid, a maximum of about 60% being preferred. When 1-hexadecene is used with low density polyethylene, amounts up to about 90% or more may be readily utilized. When polypropylene is used with the tallowamine previously described, the amine may be suitably employed in amounts of from about 10 to 90%, with a maximum amount of no more than about 85% being preferred. With polystyrene and 1-dodecanol, the concentration of the alcohol can vary from about 20 to about 90%, with from about 30 to about 70% being preferred. When styrene-butadiene copolymers are employed, the amine content may range from about 20 to about 90%. When a decanol and styrene-butadiene copolymer (i.e.-SBR) system is used, the liquid content can suitably vary from about 40 to about 90%; with diphenylamine, the liquid content is suitable within the range of from about 50 to about 80%. When microporous polymers are formed from the amine and an ethylene-acrylic acid copolymer, the liquid content may vary within the range of from about 30 to about 70%; with diphenyl ether, the liquid content may vary from about 10 to about 90%, as is the case when dibutylphthalate is used as the solvent.

SHAPING OF THE HOMOGENEOUS LIQUID

Following the formation of the solution, the same may then be processed to provide any desired shape or configuration. In general, and depending upon the particular system involved, the thickness of the article can vary from a thin film of about 1 mil. or less up to a relatively thick block of thickness of about 2½ inches or even more. The ability to form blocks thus allows the microporous material to be processed into any desired intricate shape, as by using conventional extrusion, injection molding or other related techniques. The practical considerations involved in determining the range of thicknesses which can be made from a particular system include the rate of viscosity build-up which the system undergoes as it cools. Generally, the higher the viscosity, the thicker the structure can be. The structures can accordingly be of any thickness so long as gross phase separation does not occur, i.e.—2 discernible layers become visually apparent.

It will be appreciated that if liquid-liquid phase separation is allowed to take place under thermodynamic equilibrium conditions the result will be a complete separation into two distinct layers. One layer consisting of molten polymer containing the soluable amount of liquid and a liquid layer containing the soluable amount of polymer in the liquid. This condition is represented by the binodial line in the phase diagram in FIGS. 1 and 1A. It is apparent that a limitation as to the size of object which may be prepared is governed by the heat transfer characteristics of the composition for if the object is thick enough and the heat transfer is poor enough the rate of cooling in the center of the object may be slow enough to approach thermodynamic equilibrium conditions and result in a distinct layer phase separation as previously described.

Increased thicknesses may also be achieved by the addition of minor amounts of thixotropic materials. For example, the addition of commercially available colloidal silica prior to cooling significantly increases useful thicknesses yet does not adversely affect the characteristic microporous structure. The particular amounts to be used can be readily determined.

COOLING OF THE HOMOGENEOUS SOLUTION

As is apparent from the above discussion, regardless of the type of processing (e.g.—casting into a film or the like), the solution must be cooled down to form what behaves as, and appears as, a solid. The resulting material should have sufficient integrity so that it will not crumble upon handling, as in one's hand. A further test to ascertain whether the requisite system possesses the desired structure is to employ a solvent for the liquid employed but not for the polymer. If the material disintegrates, the system employed did not satisfy the necessary criteria.

The rate of cooling of the solution may be varied within wide limits. Indeed, in the usual case, no external cooling need be employed, and it is satisfactory merely to, for example, cast a film by pouring the hot liquid system onto a metallic surface heated to a temperature which allows the drawing of the film or, alternatively, forming a block by pouring onto a substrate at ambient conditions.

The rate of cooling, as previously discussed must be sufficiently fast so that the liquid-liquid phase separation does not occur under thermodynamic equilibrium conditions. Furthermore, the rate of cooling may have substantial effect upon the resultant microporous structure. For many polymer/liquid systems, if the rate of cooling is sufficiently slow, but still satisfying the aforementioned criteria, then the liquid-liquid phase separation will result at substantially the same time in the formation of a plurality of liquid droplets of substantially the same size. If the cooling rate is such that the plurality of liquid droplets does form, as long as all other conditions discussed herein have been satisfied, the resultant microporous polymer will have the cellular microstructure, as previously defined.

In general, it is believed that the unique structures of the microporous polymers of the present invention are obtained by cooling the liquid system to a temperature below the binodial curve, as shown in FIG. 1, so that liquid-liquid phase separation is initiated. At this state, nuclei will begin to form, consisting principally of pure solvent. When the rate of cooling is such that the cellular microstructure results, it is also believed that as each such nucleus continues to grow, it becomes surrounded by a polymer-rich region which increases in thickness as it becomes depleted of liquid. Eventually, this polymer-rich region resembles a skin or film covering the growing droplet of solvent. As the polymer-rich region continues to thicken, the diffusion of additional solvent through the skin decreases; and the growth of the liquid droplet correspondingly decreases until it effectively stops, the liquid droplet having reached its maximum size. At this point, the formation of a new nucleus is more probable than continued growth of the large solvent droplet. However, to achieve this mode of growth, it is necessary that nucleation be initiated by spinodal decomposition rather than by binodial decomposition.

The cooling is thus carried out in such a fashion as to form at substantially the same time a plurality of liquid droplets of substantially the same size in a continuous polymer phase. If this decomposition mode does not take place, the cellular structure will not result. The appropriate decomposition mode is achieved, in general, by employing conditions which insure that the system does not achieve thermodynamic equilibrium until at least the nucleation or droplet growth has been initiated. Process-wise, this can be accomplished by merely allowing the system to cool without subjecting it to mixing or other shear forces. The time parameter may also be significant where relatively thick blocks are being formed, making more rapid cooling desirable in such instances.

Within the range over which cooling results in the formation of a plurality of liquid droplets, there is a general indication that the rate of cooling may affect the size of the resulting cells, with increasing rates of cooling resulting in smaller cells. In this connection, it has been observed that an increase in the cooling rate from about 8° C./minute will apparently result in decreasing the cell size in half for a polypropylene microporous polymer. Accordingly, external cooling may be utilized, if desired, to control the ultimate cell and pore size, as will be discussed in more detail.

The manner in which the interconnecting passageways or pores are formed in the cellular structure is not fully understood. However, and while the applicant does not wish to be bound by any particular theory there are various possible mechanisms that serve to explain this phenomenon, each of which is consistent with the concept described herein. The formation of the pores may accordingly be due to thermal shrinkage of the polymer phase upon cooling, the liquid solvent droplets behaving as incompressible spheres when the solvent has a smaller expansion coefficient than the polymer. Alternatively, and as has been pointed out, even after the solvent droplets have reached their maximum size, the polymer-rich phase will still contain some residual solvent and vice versa. When the system continues to cool, additional phase separation may accordingly occur. The residual solvent in the polymer-rich skin can therefore diffuse to the solvent droplet, reducing the volume of the polymer-rich skin and increasing the volume of the solvent droplet. Conceptually, this may weaken the polymer skin; and the volume increase of the solvent or liquid phase may result in internal pressure which is capable of bursting through the polymer skin, connecting adjacent solvent droplets. Related to this last mechanism, the polymer may redistribute itself into a more compact state as the residual liquid migrates out of the polymer skin, as by crystallization when this type of polymer is employed. In such a situation, the resulting polymer skin would likely shrink and have imperfections or apertures, likely located in the areas of particular weakness. The weakest ares would, it can be expected, be located between adjacent liquid droplets; and, in such a situation, the apertures would form between adjacent liquid droplets and result in the interconnection of the solvent droplets. At any rate, and regardless of the mechanism, the interconnecting pores or passageways inherently result when the process is carried out as has been described herein.

An alternative explanation of the mechanism by which the pores are formed is based on the "Marangoni effect", which has been discussed in Marangoni, C. *Nuovo Cimento* [2] 5–6.239 (1871; [3], 3,97,193 (1878) and Marangoni, C. *Ann. Phys. Lpz.* (1871), 143,337. The Marangoni effect has been utilized to explain the phenomenon occurring when alcoholic beverages spontaneously reflux off the sides of drinking glasses, particularly, the mechanism occurring when a condensed droplet flows back into the bulk of the liquid. The fluid of the droplet first penetrates that of the bulk, followed by the rapid retreat of part of the fluid back into the droplet. It has been hypothesized that a similar physical phenomenon is occurring with the liquid droplets which have formed as a result of the liquid-liquid phase separation. Thus, one droplet may encounter another and the fluid of one may penetrate that of the other, followed by rapid separation of the two droplets, perhaps then leaving a portion of the liquid connecting the two droplets and forming the basis for the interconnecting pores of the cellular structure. For a more recent discussion of the Marangoni effect, one may refer to Charles & Mason, *J. Colloid Sc.*, 15, 236–267 (1960).

If the cooling of the homogeneous solution occurs at a sufficiently fast rate, liquid-liquid phase separation may occur under non-equilibrium thermodynamic conditions, but substantial solidification of the polymer may occur so rapidly that essentially no nucleation and subsequent growth may occur. In such an instance there will be no formation of a plurality of liquid droplets and the resulting microporous polymer will not have the distinct cellular structure.

Thus, under some circumstances it is possible to obtain different microporous structures by use of exceptionally high cooling rates. For example, when a solution of 75 parts of N,N-bis(2-hydroxyethyl) tallowamine and 25 parts of polypropylene is cooled at rates varying from about 5° C. to about 1350° C. per minute, the cellular microstructure results. The main effect of different cooling rates in the foregoing range on the composition is the alteration of the absolute cell size. Where cooling rates of about 2000° C./minute are achieved, the microstructures take on, for example, a fine lacey, non-cellular appearance. When a solution of 60 parts of N,N-bis(2-hydroxyethyl) tallowamine and 40 parts of polypropylene are treated in the same fashion, cooling rates in excess of 2000° C. per minute must be achieved before the lacey non-cellular structure is obtained.

To investigate the effect of cooling system rate on the cell size of the cellular structure and to investigate the rate of cooling necessary for transition from production of the cellular structure to production of a structure having no distinct cells, various concentration of polypropylene and N,N-bis(2-hydroxyethyl) tallowamine were prepared as homogeneous solutions. To accomplish such an investigation, the DSC-2, previously discussed, was utilized in conjunction with standard X-ray equipment, and a scanning electron microscope. As the DSC-2 is capable of a maximum cooling rate of about 80° C./minute, a thermal gradient bar was also utilized. The thermal gradient bar was a brass bar which was capable of having a temperature differential of greater then 2000° C. across its one meter length, upon which samples could be placed.

An infrared camera was utilized to determine the temperatures of the samples by first focusing the camera on a pan which was placed in the closest of the ten bar sites to a temperature of 110° C., as measured with a thermocouple. The camera emissivity control was then adjusted until the camera temperature readout agreed with the thermocouple reading.

For any given run, the camera was focused on a location at which a given pan containing the sample solution was to cool. The pan with the sample was then placed on the thermal gradient bar for two minutes. As the pan was removed from the bar to be placed in the field of the camera, a stopwatch was started. As soon as the camera indicated that the pan was at a temperature of 110° C., the stopwatch was stopped and the time recorded. Thus, the determined cooling rates were based on the time needed for the sample to cool over a temperature range of approximately 100° C.

It was found that the controlling limitation on the rate of cooling was not the amount of material being cooled. It was noted that although heavier samples cooled more slowly than light ones, the silicon oil which was used on the bottom of the pan for thermal conductivity between the pan and bar had significant influence on the rate of cooling. Thus the highest cooling rates were obtained by placing a pan without any silicon oil on an ice cube and the slowest cooling rates were obtained with a pan having a heavy coating of silicon oil which was placed onto a piece of paper.

Five samples of polypropylene were prepared containing from 0 percent N,N-bis(2-hydroxyethyl) tallowamine to 80 percent of said amine, for use in investigating the effect of cooling rate on the resultant structures. Approximately 5 milligrams of each of said samples were heated on the DSC-2 inside of sealed pans at 40° C. per minute to a holding temperature of 175° C. for the sample containing 20 percent polypropylene, 230° C. for the sample containing 40 percent polypropylene, 245° C. for the sample containing 60 percent polypropylene, 265° C. for the sample containing 80 percent polypropylene and 250° C. for the 100 percent polypropylene.

Each of the samples were heated to and maintained at the appropriate holding temperature for five minutes prior to being cooled. After the samples were cooled at the desired cooling rate, the N,N-bis(2-hydroxyethyl) tallowamine was extracted from the sample with methanol and the sample analyzed. The results of the study are summarized in TABLE I showing the sizes of the cells in microns, in the resulting compositions. All cell sizes were determined by making measurements from the respective scanning electron micrographs.

TABLE I

| Cooling Rate | 5° C./Min. | 20° C./Min. | 40° C./Min. | 80° C./Min. |
|---|---|---|---|---|
| Composition | | | | |
| 0% Amine | None[1] | None[1] | None[1] | None[1] |
| 20% Amine | 0.5[2] | 0.5[2] | None[3] | None[3] |
| 40% Amine | 2.5[4] | 2.0[4] | 2.0[4] | 0.7[5] |
| 60% Amine | 4.0 | 3.0 | 2.0 | 1.5[6] |
| 80% Amine | 0.5 | 4.0 | 3.0 | 3.0[6] |

[1]Some irregular holes present
[2]Approximation of largest cell size
[3]Porosity probably too small to measure
[4]Some small cells present at 1/10 size of larger cells
[5]Additional cells present too small to measure
[6]Some formation of non-cellular structure An additional cooling rate study was conducted utilizing samples of 20 percent polypropylene and 80 percent N,N-bis(2-hydroxyethyl) tallowamine on the thermal gradient bar. Five of such samples were cooled at various rates from a melt temperature of 210° C. and the results are summarized in TABLE II, showing the sizes of the cells in microns, the same procedure being utilized as for obtaining the data for TABLE I.

TABLE II

| Cooling Rate | 200° C. | 870° C./Min. | 1350° C./Min. | 1700° C./Min. |
|---|---|---|---|---|
| Composition | | | | |
| 80% Amine | 0.5-3 | 0.5-1.5 | 1.5-2.5 | Non-cellular |

From TABLES I and II it is apparent that for increasing cooling rates, the size of the cells in the resulting compositions decrease, in general. Furthermore, with respect to the polymer/liquid system comprised of 20 percent polypropylene and 80 percent N,N-bis(2-hydroxyethyl) tallowamine, it is apparent that at a cooling rate between about 1350° C. per minute and 1700° C. per minute a transition is completed in the nature of the resultant polymer from essentially cellular to non-cellular. Such a transition in the resultant structure corresponds to the fact that the polymer becomes substantially solidified after liquid-liquid phase separation has been initiated but prior to the formation of a plurality of liquid droplets, as previously discussed.

Additionally five samples of 40 percent polypropylene and 60 percent N,N-bis(2-hydroxyethyl) tallowamine were prepared and cooled at rates from 690° C. per minute to over 7000° C. per minute, from melt temperatures of 235° C., in accordance with the procedure discussed previously. It was determined that for such a concentration of polypropylene and said amine, the transition from cellular to non-cellular occurs at about 2000° C. per minute.

Finally, to investigate the crystallinity of structures prepared over a range of cooling rates, three samples of 20 percent polypropylene and 80 percent of N,N-bis(2-hydroxyethyl) tallowamine were prepared and cooled at rates of 20° C., 1900° C. and 6500° C. per minute. From the DSC-2 data for such samples it was determined that the degree of crystallinity in the three samples was essentially equivalent. Thus it appears that variations in the cooling rate have no significant effect upon the degree of crystallinity of the resulting structures. However, it was determined that as the rate of cooling was significantly increased, the crystals which were produced became less perfect, as expected.

REMOVAL OF THE LIQUID

Having formed the homogeneous solution of polymer and liquid and having cooled the solution in an appropriate manner to produce a material having suitable handling strength, the microporous product may be thereafter formed by removing the liquid by, for example, extracting with any suitable solvent for the liquid which is, likewise, quite obviously, a nonsolvent for the polymer in the system. The relative miscibility or solubility of the liquid in the solvent being employed will, in part, determine the effectiveness in terms of the time required for extraction. Also, if desired, the extracting or leaching operation can be carried out at an elevated temperature below the softening point of the polymer to lessen the time requirements. Illustrative examples of useful solvents include isopropanol, methylethyl ketone, tetrahydrofuran, ethanol and heptane.

The time required will vary, depending upon the liquid employed, the temperature used and the degree of extraction required. More particularly, in some instance, it may be unnecessary to extract 100% of the liquid used in the system and minor amounts may be tolerated, the amount which can be tolerated being dependent upon the requirements of the intended end-use application. The time required may accordingly vary anywhere in the range of from several minutes or perhaps less to more than 24 hours or even more, depending upon many factors, including the sample thickness.

Removal of the liquid can also be achieved by other known techniques. Illustrative examples of other useful removal techniques include evaporation, subliation and displacement.

It should be noted in addition, when using conventional liquid extraction techniques, the cellular microporous polymer structures of the present invention may exhibit release of a liquid contained in the structure in a fashion which approaches zero order, i.e., the rate of release may be essentially constant after, perhaps, an initial period at a high release rate. In other words, the rate of release may be independent of the amount of the liquid that has been released; thus, the rate at which the liquid is extracted after, for example, three-fourths of the liquid has been removed from the structure is approximately the same as when the structure was one-half filled with liquid. An example of such a system exhibiting an essentially constant release rate is the extraction of N,N-bis-(2-hydroxyethyl) tallowamine from polypropylene with isopropanol as the extractant. Also, in any situation, there probably will be an initial induction period before the rate of release becomes identifiable. When release of a liquid is allowed to proceed by evaporation, the rate of release tends to be first order.

CHARACTERIZATION OF THE MICROPOROUS POLYMERS CELLULAR STRUCTURE

Figure 2:
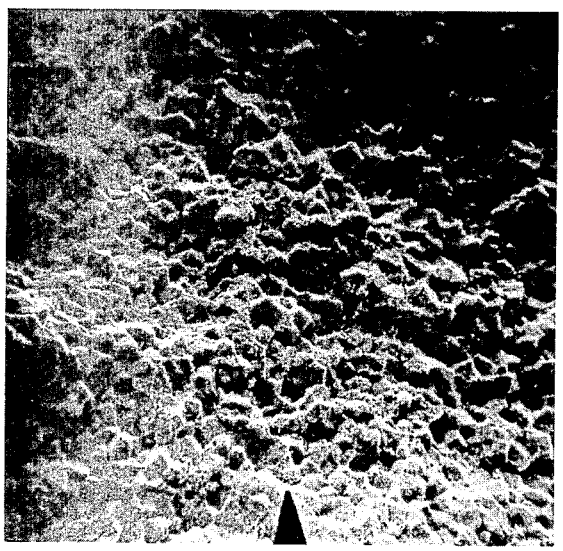
FIG. 2 is a photomicrograph, at 55X amplification, showing the macrostructure of a polypropylene microporous polymer of the present invention with about a 75 percent void volume.
Figure 3:
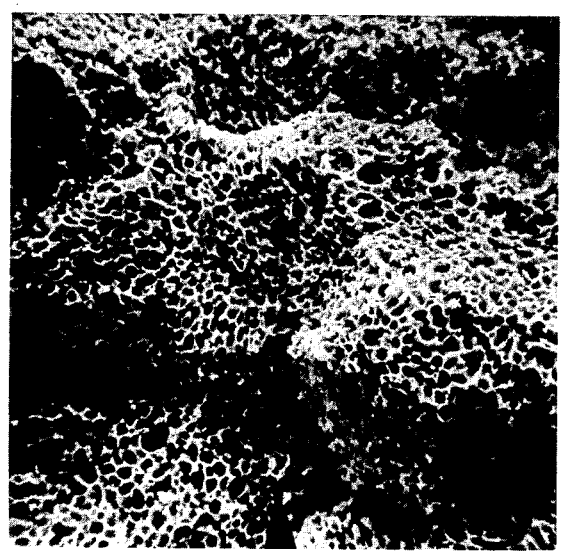
FIGS. 3 through 5 are photomicrographs of the microporous polypropylene structure of FIG. 2 at, respectively, 550X, 2200X and 5500X amplification, and illustrate a homogeneous cellular structure.
Figure 4:
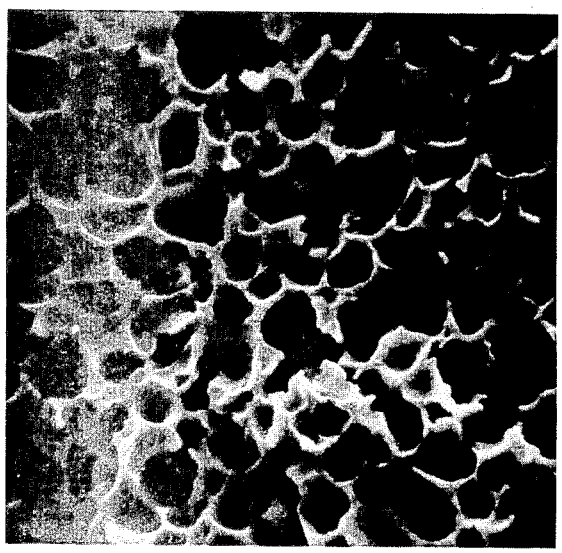
Figure 5:
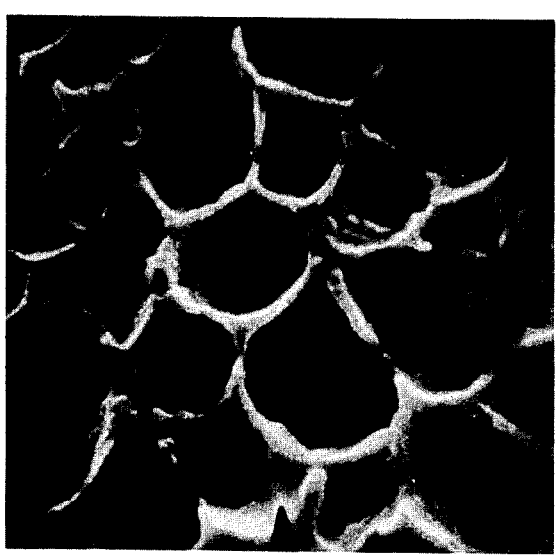

When the cooling of the polymer/liquid solution occurs such that the plurality of liquid droplets form as previously discussed, and the liquid removed therefrom, the resulting microporous product forms a relatively homogeneous cellular structure comprising, on the microscale, a series of substantially spherical, enclosed microcells distributed substantially uniformly throughout the structure. Adjacent cells are interconnected by smaller pores or passageways. This basic structure can be seen from the photomicrographs of FIGS. 4 and 5. It should be appreciated that the individual cells are, in fact, enclosed but appear open in the photomicrographs due to the fracturing involved in the sample preparation for taking the photomicrographs. On a macroscale, at least for the crystalline polymers, the structure appears to have planes similar to the fracture planes along the edges of crystal growth (see FIG. 2) and, as can be seen from FIG. 3, is coral-like in appearance. The cellular microstructure may further be analogized to zeolite clay structures, which contain definite "chamber" and "portal" regions. The cells correspond to the larger chamber areas of zeolite structures while the pores correspond to the portal regions.

In general, in the cellular structure the average diameter of the cells will vary from about ½ micron to about 100 microns, about ½ to about 50 microns being more typical whereas the average diameter of the pores or interconnecting passageways appears to be typically about a magnitude smaller. Thus, for example, if the cell diameter in a microporous polymer structure of the present invention is about 1 micron, the average diameter of the pore or interconnecting passageway will be about 0.1 micron. As has been pointed out previously, the cell diameter and also the diameter of the pore or passageway will be dependent upon the particular polymer-liquid system involved, the rate of cooling and the relative amounts of polymer and liquid utilized. However, a broad range of cell to pore ratios are possible, as, for example, from about 2:1 to about 200:1, typically, from about 5:1 to about 40:1.

Figure 6:
FIGS. 6 through 10 are photomicrographs at, respectively, 1325X, 1550X, 1620X, 1450X and 1250X amplification of additional microporous polypropylene structures and show the modifications in the structure as the void space is reduced from 90%, to 70%, to 60%, to 40%, and to 20%, respectively.
Figure 7:
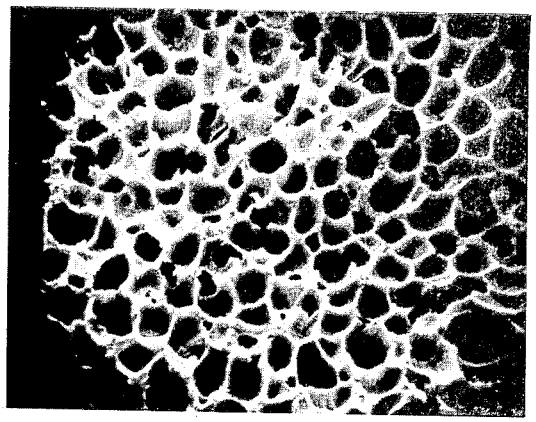

As can be seen from the several Figures, it may be considered that some of the exemplary cellular microporous polymer products do not possess the unique microcellular structure which has been described herein. It must, however, be appreciated that this structure can, in some instances, be masked by additional modifications resulting from the particular liquid or polymer involved or the relative amounts employed. This masking may be in whole or in part, ranging from small polymer particles attached to the walls of the cells to gross "foliage-type" polymer build-ups which, in the micrographs, tend to completely mask the basic structure. Thus, for example, and as can be seen from FIGS. 21 and 25, small polymer balls are adhered to the cell cavities of the structures. This additional formation can be understood by reference to the nucleation and growth concept previously described. Thus, in systems with extremely high solvent or liquid content, the maximum cavity size will typically be comparatively large. This likewise means that the time required for the cavity or droplet to reach its maximum size will similarly be increased. During this time, it is possible for additional nuclei to form thereby. Two or more nuclei may then come into contact with one another prior to each reaching its maximum size. In such instances, the resulting cellular structure has less integrity and somewhat less regularity than the basic structure previously described. Moreover, even after the liquid droplets have reached maximum size, depending upon the system involved, the solvent or liquid phase may still contain some amount of residual polymer or vice versa. In such situations, as the system continues to cool, some additional residual phase separation may occur. When the residual polymer simply separates out of solution, spheres of polymer can form as shown in FIGS. 21 and 25. On the other hand, if the residual polymer diffuses to the polymer skin, the walls will appear fuzzy and irregular, thus providing the "foliage-type" structure. This "foliage-type" structure may only partially mask the basic structure, as seen in FIGS. 28 and 29 or it may wholly mask the structure as shown in FIG. 6.

Figure 8:
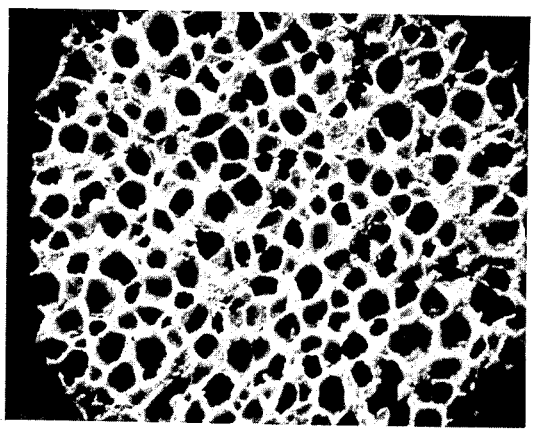
Figure 9:
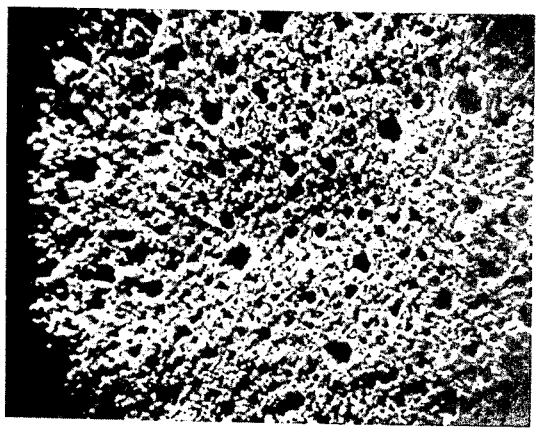
Figure 10:
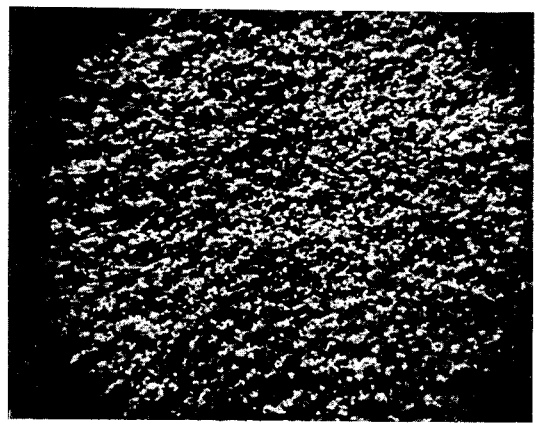

The "foliage-type" structure is also more prone to occur with certain polymers. Thus, the microporous low density polyethylene structures, perhaps due to the solubility or the like of the polyethylene in the particular liquids employed, typically provide this sort of structure. This can be observed from FIG. 14. Further, when the levels of liquid employed are extremely high, this will also occur with polymers such as polypropylene which otherwise exhibit the basic structure. This can be readily observed by contrasting the "foliage-type" structure of the microporous product of FIG. 6 with the basic structure of FIG. 8 in which the polymer content is 40% by weight comparison to the 10% polypropylene in the structure illustrated in FIG. 6.

For most applications, it is preferred to utilize a system which results in the formation of the basic cellular structure. The relative homogeneity and regularity of this structure provides predictable results, such as are required in filtration applications. However, the foliage-type structure may be more desirable where relatively high surface area structures are desired such as in ion exchange or various adsorptive processes.

As can be likewise observed, some of the structures have small holes or apertures in the walls of the cells. This phenomenon can also be understood by reference to the nucleation and growth concept. Thus, in a section of the system in which a few spatially associated liquid droplets have already reached their maximum size, each droplet will be enclosed by a polymer-rich skin. However, in some instances, some solvent may be trapped between the enclosed droplets but cannot continue its migration to the larger droplets to to impenetratibility of the skins. Accordingly, in such instances, a nucleus of the liquid may form and grow, resulting in a small cavity embedded adjacent to the larger droplets. After extraction of the liquid, the smaller droplets will appear as a small hole or aperture. This can be observed in the microporous structures shown in FIGS. 11–12 and 20.

Another interesting characteristic of the cellular structures of the present invention relates to the surface area of such structures.

The theoretical surface area of the cellular microporous structure consisting of interconnected spherical cavities of about 5 microns in diameter is approximately 2–4 sq meters/gm. It has been found that microporous polymers produced by the instant invention need not be limited to the theoretical limit of surface area. Determination of surface area by the B.E.T. method described in Brunauer, S., Emmett, P. H. and Teller, E. "The Adsorption of Gases in Multimolecular Layers" *J. Am. Chem. Soc.*, 60, 309,–16 (1938), has shown surface surface areas far in excess of the theoretical model which is not related to the void space, as shown in TABLE III, for microporous polymers made from polypropylene and N,N-bis(2-hydroxyethyl) tallowamine.

TABLE III

| % VOID | SPECIFIC SURFACE AREA |
|---|---|
| 89.7 | 96.2 m$^2$/gm |
| 72.7 | 95.5 |
| 60.1 | 98.0 |
| 50.5 | 99.8 |
| 28.9 | 88.5 |

Surface area may be reduced by careful annealing of the microporous polymer without affecting the basic structure. Microporous polypropylene prepared at 75% void space using N,N-bis(2-hydroxyethyl) tallowamine as the liquid component was extracted and dried at temperatures not exceeding room temperature and subsequently heated to affect the surface area. The initial surface area was 96.9 m$^2$/g. After eleven 40 minute heat periods at 62° C. the surface area fell to 66 m$^2$/gm. Further heating at 60° C. for an additional 66 hours decreased the surface area to 51.4 m$^2$/gm. Treatment of another sample at 90° C. for 52 hours decreased the surface area from 96.9 to 33.7 m$^2$/gm. The microporous structures was not significantly changed when examined by scanning electron microscopy.

These results are summarized in Table IV.

TABLE IV

| Treatment | Surface area (m$^2$/gm) | % Change |
|---|---|---|
| none | 96.9 | — |
| eleven, 40 min. treatments at 62° C. | 66.0 | 32% |
| Above plus 66 hours at 60° C. | 51.4 | 47% |
| 52 hours at 90° C. | 33.7 | 65% |

It should be quite apparent that one of the unique features of the cellular structures of the present invention relates to the existence of both distinct, substantially spherical, enclosed microcells which are uniformly distributed throughout the structure and distinct pores which interconnect said cells, said pores being of a smaller diameter than said cells. Furthermore, said cells and interconnecting pores have essentially no spatial orientation, and may be classified as being isotropic. Thus there is no preferred direction, as for example, for flow of a liquid through the structure. This is in marked contrast to prior art materials which do not exhibit such a cellular structure. Many prior art systems have a nondescript structure which lacks any structural configuration capable of definition. It is therefore quite surprising that a microporous structure can be made having such a degree of uniformity, which may be especially desirable for many applications needing highly uniform materials.

The cellular structure may be defined in terms of the ratio of the average diameter of the cells ("C") to the diameter of the pores ("P"). Thus, the C/P ratio as previously discussed may vary from about 2 to about 200, about 5 to about 100 being typical and about 5 to about 40 being even more typical. Such a C/P ratio distinguishes the cellular structure of the present invention from any previous prior art microporous polymeric product. As there is no known prior art synthetic thermoplastic polymeric structure having distinct cells and pores, all such prior art materials must be considered to have a cell to pore ratio of 1.

Another means of characterizing the cellular structures of the present invention is by a sharpness Factor, "S". The S factor is determined by analyzing a mercury intrusion curve for the given structure. All mercury intrusion data discussed in this application was determined by use of a Micromeritics Mercury Penetration Porosimeter, Model 910 series. The S value is defined as the ratio of the pressure at which 85 percent of the mercury penetrated to the pressure at which 15 percent of the mercury penetrated. This ratio is a direct indication of the variation in pore diameter across the central 70 percent of the pores in any given sample, as pore diameter is equal to 176.8 divided by the pressure in p.s.i.

The S value, then, is a ratio of the diameter of the pores at which 15 percent of the mercury has intruded to the diameter of the pores at which 85 percent of the mercury has intruded. The range for 1 to 15 percent and 85 to 100 percent of mercury intrusion is ignored in determining the S factor. The range from 0 to 15 percent is ignored as penetration in this range may be due to cracks introduced into the material as a result of the freeze-fracturing to which the material was subjected prior to performing the mercury intrusion study. Also, the range from 85 to 100 percent is ignored as data in such a range may be due to compression of the sample rather than to actual penetration of the mercury into the pores.

Characteristic of the narrow range of pore sizes exhibited by the composition of the present invention, the usual S value for such structures is in the range of from about 1 to about 30, about 2 to about 20 being typical and about 2 to about 10 being more typical.

The average size of the cells in the structure range from about 0.5 to about 100 microns, from about 1 to about 30 microns being typical, from about 1 to about 20 microns being more typical. As indicated the cell size may vary depending on the particular resin and compatible liquid utilized, the ratio of polymer to liquid, and the cooling rate employed to form the particular microporous polymer. The same variable will also have an effect upon the average size of the pores in the resulting structure, which usually varies from about 0.05 to about 10 microns from about 0.1 to about 5 microns being typical, and from about 0.1 to about 1.0 micron being more typical. All references to a cell and/or pore size throughout this application, relate to the average diameter of such cell or pore, in microns, unless otherwise stated.

By determining the foregoing factors, cell size, pore size, and S, for the cellular microporous polymers of the present invention, one may concisely define the cellular microporous polymers of the present invention. A particularly useful means of so defining the polymers in terms of the log of the cell to pore ratio ("log C/P") and the log of the ratio of the sharpness function S to the cell size ("log S/C"). Accordingly, the cellular microporous polymers of the present invention have a log C/P of from about 0.2 to about 2.4 and a log S/C of from about −1.4 to about 1.0, more usually, said polymers have a log C/P of from about 0.6 to about 2.2 and a log S/C of from about −0.6 to about 0.4.

Non-cellular Structure

The non-cellular structure of the present invention which results from the cooling of the homogeneous solution at such a rate that the polymer substantially solidifies prior to the formation of the plurality of liquid droplets, may be characterized primarily with respect to the narrow pore size distribution of the material in conjunction with the actual pore size and the spatial uniformity of the structure.

Particularly, the non-cellular microporous polymers may be characterized by a sharpness function, S, as previously described with respect to the cellular structures. The S values exhibited by the non-cellular structure range from about 1 to about 30, about 1 to about 10 being preferred and about 6 to about 9 being more preferred. However, when the pore size of the material ranges from about 0.2 to about 5 microns, the S value will range from about 5 to about 10 and will typically range from about 5 to about 10. Such S values for olefinic and oxidation polymers having microporosity of such a size has been unknown heretofore, except in the case of highly oriented, thin films made by a stretching technique. As previously indicated, the porous polymers of the present invention are substantially isotropic. Thus a cross-section of the polymers taken along any spatial plane will reveal essentially the same structural features.

The pore sizes of the non-cellular structures of the present invention are usually in the range from about 0.05 to about 5 microns, from about 0.1 to about 5 microns being typical, and from about 0.2 to 1.0 micron being more typical.

It is apparent that a surprising feature of the present invention is the ability to produce isotropic microporous structures from olefinic and oxidation polymers, with the structures having porosity in the range from about 0.2 to about 5 microns and a sharpness value from about 1 to about 10. It is especially surprising that such structures may be made in the form, not only of thin films, but also in the form of blocks and intricate shapes.

GENERAL

When forming a film or block by pouring onto a substrate such as metal plate, for example, the surface of the microporous polymer structure of the present invention which is in contact with the plate will comprise a surface skin that is non-cellular. The other surface, in contrast, is typically predominantly open. The thickness of the skin will vary somewhat in accordance with the particular system as well as the particular process parameters employed. However, typically, the thickness of the skin is approximately equal to the thickness of a single cell wall. Depending upon the particular conditions, the skin may range from one which is wholly impervious to the passage of liquids to one exhibiting some degree of liquid porosity.

If a solely cellular structure is desired for the ultimate application, the surface skin may be removed by any of several techniques. As illustrative examples, the skin could be removed by employing any one of several mechanical means such as abrading, puncturing the skin with needles or fracturing the skin by passing the film or other structure through differential speed rollers. Alternatively, the skin could be removed by microtoming. The skin may also be removed by chemical means, i.e.—by brief contact with a suitable solvent for the polymer.

For example, when a solution of polypropylene in N,N-bis (2-hydroxyethyl) tallowamine is continuously extruded as a thin film onto an endless stainless steel belt conveyor, application of a small amount of liquid solvent upon the belt immediately prior to the solution application zone will effectively remove the surface formed at the solution-steel interface. Useful liquids are materials such as isoparaffinic hydrocarbons, decane, decalin, xylene and mixtures such as xylene-isopropanol and decalin-isopropanol.

However, for some end use applications, the presence of the skin will not only be a detriment but will be a necessary component. For example, as is known, ultrafiltration or other membrane-type applications utilize a thin, liquid impenetrable film. Accordingly, in such applications, the microporous portion of the structure of the present invention would have particular utility as a support for the surface skin which would be functioning membrane in such applications. Wholly cellular structures can also be directly prepared by various techniques. Thus, for example, the polymer-liquid system could be extruded into air or a liquid medium such as, for example, hexane.

The microporous polymer structures of the present invention, as has been previously discussed, have cell and pore diameters with extremely narrow size distributions which are indicative of the unique structures and their relative homogeneity. The narrow size distribution of the pore diameters is apparent from mercury intrusion data, as can be seen from FIGS. 30–33. The same general distribution is obtained regardless of whether the structure is in the form of a film (FIGS. 30–32) or a block (FIG. 33). The characteristic pore size distribution of the microporous structure of the present invention is in marked contrast to the significantly broader pore size distributions of prior microporous polymer products achieved by prior processes, such as, for example, those set forth in U.S. Pat. Nos. 3,310,505 and 3,378,507, as will be discussed in greater detail in connection with the Examples.

For any of the microporous polymers made in accordance with the present invention, the particular end use application will typically determine the amount of void space and pore size requirements. For example, for prefilter applications, the pore size will typically be above 0.5 microns while, in ultrafiltration, the pore sizes should be less than about 0.1 micron.

In applications where the microporous structure serves, in effect, as a receptacle for a functionally useful liquid strength considerations dictate the amount of void space where controlled release of the contained functional liquid is involved. Similarly, in such cases, the pore size will be dictated by the rate of release desired, smaller pore sizes tending to provide slower rates of release.

Where the microporous structure is to be utilized to convert a liquid polymer additive such as a flame retardant to a solid, some minimum strength is generally desired; but, consistent with this minimum, it will typically be desired to utilize as much liquid as possible since the polymer serves merely as a receptacle or carrier.

MICROPOROUS POLYMERS CONTAINING FUNCTIONAL LIQUIDS

From the foregoing discussions it should be appreciated that in accordance with one aspect of the present invention, microporous products containing a functionally useful liquid such as polymer additive (e.g.—flame retardant) may be prepared which behave as, and may be processed as, a solid. To this end, the resulting microporous polymer may be reloaded with the desired functional liquid. This can be accomplished by conventional absorption techniques, and the amount of liquid taken up will be essentially the same as the amount of liquid used in forming the microporous polymer in the first instance. Any useful organic liquid may be employed so long as, of course, the liquid is not a solvent for the polymer, or otherwise attacks or degrades, the polymer at the working temperature. The microporous products containing the functionally useful liquid may be formed from or by using microporous polymers having either the cellular or non-cellular structure, as the matrix in which the liquid is incorporated.

Similarly, such microporous products can be prepared by a displacement technique. In accordance with this embodiment, the microporous polymer intermediate is first prepared; and the liquid is then displaced, whether with the desired functionally useful liquid or with an intermediate displacing liquid. In either case, rather than extracting the liquid used in forming the microporous polymer intermediate, the displacement is carried out by conventional pressure or vacuum displacement or infusion techniques. Any functional or intermediate displacing liquid may be used which could be used as an extracting liquid to form the microporous polymer, i.e.—is a non-solvent for the polymer yet has some solubility or miscibility with the liquid being displaced. As is apparent, minor amounts of the displaced liquid or liquids may remain following displacement. The requirement of the end use will typically dictate the extent of the displacement desired; thus, amounts of about 1 to about 10% by weight may be tolerated in some applications. If required, multiple displacements and/or using liquids that can be readily removed by evaporation allows removal of essentially all of the liquid or liquids being displaced, i.e.—less than about 0.03 or so weight percent of residual liquid can be achieved. From the economic standpoint, it will generally be desirable to utilize a displacing liquid which has a boiling point sufficiently different from the liquid being displaced to allow recovery and reuse. For this reason, it may be desirable to utilize an intermediate displacing liquid.

As may also be apparent from the foregoing examples of useful polymer-liquid systems, a further method of preparing a polymer-functionally useful liquid material involves utilizing the microporous polymer intermediate without further processing since numerous functionally useful liquids have been found to be operable as the compatible liquid with particular polymers to form the solid microporous polymer intermediate. Thus, intermediates which behave as solids can be directly made with liquids useful as lubricants, surfactants, slip agents, moth repellents, pesticides, plasticizers, medicinals, fuel additives, polishing agents, stabilizers, insect and animal repellents, fragrances, flame retardants, antioxidants, odor masking agents, antifogging agents, perfumes and the like. For example, with low density polyethylene, useful intermediates containing a lubricant or a plasticizer may be provided by employing either an aliphatic or aromatic ester having eight or more carbon atoms or a nonaromatic hydrocarbon having nine or more carbon atoms. Useful products containing a surfactant and/or wetting agent may be formed with low density polyethylene by using a polyethoxylated aliphatic amine having eight or more carbon atoms or a nonionic surfactant. With polypropylene, surfactant-containing intermediates can be provided by utilizing diethoxylated aliphatic amines having eight or more carbon atoms. Polypropylene intermediates containing slip agents may be prepared by using a phenylmethyl polysiloxane while low density polyethylene slip agent intermediates are formed by employing an aliphatic amide having twelve to twenty-two carbon atoms. Low density polyethylene fuel additive intermediates may be prepared by utilizing an aliphatic amine having eight or more carbon atoms or an aliphatic dimethyl tertiary amine having twelve or more carbon atoms. The tertiary amines may also form useful additive intermediates with methylpentane polymers. High and low density polyethylene intermediates containing a stabilizer can be formed by using an alkyl aryl phosphite.

Intermediates of low density polyethylene including an antifogging agent may be provided by utilizing the glycerol mono or diester of a long chain fatty acid having at least ten carbon atoms. Intermediates having flame retardants incorporated therein may be prepared with high and low density polyethylene, polypropylene, and a polyphenylene oxide-polystyrene blend by using a polyhalogenated aromatic hydrocarbon having at least four halogen atoms per molecule. Useful materials should, of course, be liquid at the phase separation temperature as described herein. Other systems which have been found useful will be identified in connection with the Examples presented hereinafter.

Furthermore, for polypropylene, high density polyethylene, and low density polyethylene, certain classes of ketones which have been found to be especially useful as animal repellants may be employed generally in the practice of the present invention. Such ketones may include saturated aliphatic ketones having from 7 to 19 carbon atoms, unsaturated aliphatic ketones having from 7 to 13 carbon atoms, 4-t-amyl cyclohexanone, and 4-t-butyl cyclohexanone.

The following Examples are presented to more fully explain the present invention and are merely illustrative of the present invention and are not intended as a limitation upon the scope thereof. Unless otherwise indicated, all parts and percentages are by weight.

PREPARATION PROCEDURE

The porous polymer intermediates and the microporous polymers described in the Examples hereinafter were prepared according to the following procedure:
A. Porous Polymer Intermediates:

The porous polymer intermediates are formed by admixing a polymer and a compatible liquid, heating the mixture to a temperature which is usually near or above the softening temperature of the resin such that homogeneous solution is formed, and then cooling the solution without subjecting it to mixing or other shear forces to form a macroscopically solid homogeneous mass. When solid blocks of the intermediates are to be formed, the homogeneous solution is allowed to assume a desired shape by pouring it into an appropriate receptacle, which is usually made of metal or glass, and the solution allowed to cool under ambient room conditions, unless otherwise noted. The rate of cooling under room temperature conditions will vary, depending on items such as sample thickness and composition, but will usually be in the range of from about 10° to about 20° C. per minute. The receptable is typically cylindrical in shape with a diameter of from about 0.75 to about 2.5 inches and the solution is typically poured to a depth of from about 0.25 to about 2.0 inches. When films of the intermediates are formed, the homogeneous solution is poured onto a metal plate which is heated to a temperature sufficient to allow the drawing of the solution into a thin film. The metal plate is then placed into contact with a dry ice bath to rapidly cool the film below its solidification temperature.

B. Porous Polymer:

The microporous polymer is formed by extracting the compatible liquid used to form the porous polymer intermediate, typically be repetitively washing the intermediates in a solvent such as isopropanol or methylethyl ketone, then drying the sold microporous mass.

EXAMPLES

The following examples and tables illustrate some of the various polymer/compatible liquid combinations which are useful in forming the porous polymer intermediates of this invention and various prior art or commercially available microporous products. Solid blocks of the intermediates were formed for all of the exemplified combinations and, when so indicated in a table, thin films of the intermediate were also formed, using the procedure described above. As indicated in the following tables, many of the intermediate compositions were used to form the microporous polymers of this invention, by using a suitable solvent to extract the compatible liquid from the intermediate composition, and subsequently removing said solvent, as by evaporation.

Many of the compatible liquids which are illustrated in the following examples are, as indicated in the tables, functional liquids which are useful not only as compatible liquids but also as flame retardants, slip agents, and the like. Thus, the intermediate compositions which are formed with such functional liquids are useful as solid polymer additives and the like, as well as intermediates in the formation of porous polymers. The functional liquids which appear in the following examples are indicated to be such by the presence of one or more of the following symbols under column "Type of Functional Liquid": AF (Antifogging Agent); AO (Antioxidant); AR (Animal Repellant); FA (Fuel Additive); FG (Fragrance); FR (Flame Retardant); IR (Insect Repellant); L (Lubricant); M (Medicinal); MR (Moth Repellant); OM (Odor Masking Agent); P (Plasticizer); PA (Polishing Agent); PE (Pesticide); PF (Perfume); S (Slip Agent); SF (Surfactant), and ST (Stabilizer).

EXAMPLES 1 to 27

Examples 1 through 27 in Table V illustrate the formation of homogeneous porous polymer intermediates, in the form of cylindrical blocks having a radius of about 1.25 inches and a depth of about 2 inches, from high density polyethylene ("HDPE") and the compatible liquids found to be useful, using the standard preparation procedure. The high density polyethylene was supplied by Allied Chemical under the designation Plaskon AA 55-003, having a melt index of 0.3 g/10 minutes and a density of 0.945 g/cc. Many of the exemplified intermediates were extracted to form porous polymers, as indicated in the Table.

The details of preparation and the type of functionally useful liquid noted are set forth in Table V:

TABLE V

| Ex. No. | Liquid Type and Liquid | % Liq. | °C. | Type of Functional Liquid |
|---|---|---|---|---|
| | Saturated Aliphatic Acids | | | |
| 1 | decanoic acid* | 75 | 230 | — |
| | Primary Saturated Alcohols | | | |
| 2 | decyl alcohol* | 75 | 220 | PF |
| 3 | 1-dodecanol* | 75 | 220 | — |
| | Secondary Alcohols | | | |
| 4 | 2-undecanol* | 75 | 220 | — |
| 5 | 6-undeconal* | 75 | 230 | — |
| | Aromatic Amines | | | |
| 6 | N,N diethylaniline* | 75 | 230 | — |
| | Diesters | | | |
| 7 | dibutyl sebacate* | 70 | 220 | L, P |
| 8 | dihexyl sebacate* | 70 | 220 | L, P |
| | Ethers | | | |
| 9 | diphenyl ether | 75 | 220 | PF |
| 10 | benzyl ether* | 70 | 220 | PF |
| | Halogenated | | | |
| 11 | hexabromobenzene | 70 | 250 | FR |
| 12 | hexabromobiphenyl | 75 | 200 | FR |
| 13 | hexabromocyclodecane | 70 | 250 | FR |
| 14 | hexachlorocyclopentadiene | 70 | 200 | FR |
| 15 | octabromobiphenyl | 70 | 280 | FR |
| | Terminally Double Bonded Hydrocarbons | | | |
| 16 | 1-hexadecene* | 75 | 220 | — |
| | Aromatic Hydrocarbons | | | |
| 17 | diphenylmethane* | 75 | 220 | OM |
| 18 | naphthalene* | 70 | 230 | MR |
| | Aromatic Ketones | | | |
| 19 | acetophenone | 75 | 200 | PF |
| | Aromatic Esters | | | |
| 20 | butyl benzoate* | 75 | 220 | L, P |
| | Miscellaneous | | | |
| 21 | N,N-bis(2-hydroxyethyl) tallowamine (1)* | 70 | 250 | — |
| 22 | dodecylamine* | 75 | 220 | — |
| 23 | N-hydrogenated tallow-diethanol amine | 50 | 240 | SF |
| 24 | Firemaster BP-6 (2) | 75 | 200 | — |
| 25 | Phosclere P315C* (3) | 75 | 220 | ST |
| 26 | Quinoline | 70 | 240 | M |
| 27 | dicocoamine (4) | 75 | 220 | — |

*The liquid was extracted from the solid.
(1) A permanent internal antistatic agent having the following properties was used: Boiling Point 1 mm Hg, °C., 215–220; Specific Gravity 90° F., 0.896; Viscosity, SSU, 90° F., 476.
(2) Michigan Chemical Corporation's trademark for its hexabromo-biphenyl, a flame retardant having the following properties was used: Softening Point, °C., 72; Density, 25° C., g/ml, 2.57; Viscosity, cps, 260–360 (Brookfield #3 spindle at 110° C.).

TABLE VI

| Ex. No.(1) | Liquid Type and Liquid | % Liq. | °C. | Type of Functional Liquid |
|---|---|---|---|---|
| | Aliphatic Saturated Acids | | | |
| 28 | caprylic acid* | 70 | 210 | — |

TABLE VI-continued

LDPE

| Ex. No.(1) | Liquid Type and Liquid | % Liq. | °C. | Type of Functional Liquid |
|---|---|---|---|---|
| 29 | decanoic acid* | 70 | 190 | — |
| 30 | hexanoic acid* | 70 | 190 | — |
| 31 | lauric acid* | 70 | 220 | — |
| 32 | myristic acid* | 70 | 189 | — |
| 33 | palmitic acid* | 70 | 186 | — |
| 34 | stearic acid* | 70 | 222 | — |
| 35 | undecanoic acid* | 70 | 203 | — |
| | Unsaturated Aliphatic Acids | | | |
| 36 | erucic acid(2)* | 70 | 219 | — |
| 37 | oleic acid* | 70 | 214 | PA |
| | Aromatic Acids | | | |
| 38 | phenyl stearic acid* | 70 | 214 | — |
| 39 | xylyl behenic acid* | 70 | 180 | — |
| | Miscellaneous Acids | | | |
| 40 | Acintol FA2 (Tall Oil Acids)(3)* | 70 | 204 | — |
| 41 | olefin acid L-6* | 70 | 206 | — |
| 42 | olefin acid L-9* | 70 | 186 | — |
| 43 | olefin acid L-11* | 70 | 203 | — |
| 44 | Rosin acid* | 70 | 262 | — |
| 45 | tolylstearic acid | 70 | 183 | — |
| | Primary Saturated Alcohols | | | |
| 46 | cetyl alcohol* | 70 | 176 | — |
| 47 | decyl alcohol* | 70 | 220 | PF |
| 48 | 1-dodecanol* | 75 | 200 | — |
| 49 | 1-heptadecanol* | 70 | 168 | — |
| 50 | nonyl alcohol* | 70 | 174 | PF |
| 51 | 1-octanol* | 70 | 178 | — |
| 52 | oleyl alcohol* | 70 | 206 | FA |
| 53 | tridecyl alcohol | 70 | 240 | — |
| 54 | 1-undecanol* | 70 | 184 | — |
| 55 | undecylenyl alcohol* | 70 | 199 | — |
| | Secondary Alcohols | | | |
| 56 | dinonyl carbinol* | 70 | 201 | PF |
| 57 | diundecyl carbinol | 70 | 226 | — |
| 58 | 2-octanol | 70 | 174 | — |
| 59 | 2-undecanol* | 70 | 205 | — |
| | Aromatic Alcohols | | | |
| 60 | 1-phenylethanol* | 70 | 184 | PF |
| 61 | 1-phenyl-1-pentanol | 70 | 196 | — |
| 62 | phenyl stearyl alcohol* | 70 | 206 | — |
| 63 | nonyl phenol* | 70 | 220 | SF, PE |
| | Cyclic Alcohols | | | |
| 64 | 4-t-butyl cyclohexanol* | 70 | 190 | PE |
| 65 | menthol* | 70 | 206 | PF |
| | Other —OH Containing Compounds | | | |
| 66 | Neodol-25(4)* | 70 | 180 | — |
| 67 | polyoxyethylene ether of oleyl alcohol(5) | 70 | 268 | SF |
| 68 | polypropylene glycol-425*(6) | 70 | — | SF |
| | Aldehydes | | | |
| 69 | salicylaldehyde* | 70 | 188 | PF |
| | Primary Amines | | | |
| 70 | dimethyldodecylamine* | 70 | 200 | FA |
| 71 | hexadecylamine* | 70 | 207 | FA |
| 72 | octylamine* | 70 | 172 | FA |
| 73 | tetradecylamine* | 70 | 186 | FA |
| | Secondary Amines | | | |
| 74 | bis(1-ethyl-3-methyl pentyl) amine* | 70 | 190 | — |
| | Tertiary Amines | | | |
| 75 | N,N-dimethylsoya-amine*(7) | 70 | 198 | FA |
| 76 | N,N-dimethyltallow-amine*(8) | 70 | 209 | FA |
| | Ethoxylated Amines | | | |
| 77 | N-stearyl diethanol amine | 75 | 210 | SF, AF |
| | Aromatic Amines | | | |
| 78 | aminodiphenylmethane | 70 | 236 | — |
| 79 | N-sec-butylaniline | 70 | 196 | — |
| 80 | N,N-diethylaniline* | 70 | — | — |
| 81 | N,N-dimethylaniline* | 70 | 169 | — |
| 82 | diphenylamine | 70 | 186 | AO, PE |
| 83 | dodecylaniline* | 70 | 204 | — |
| 84 | phenylstearyl amine* | 70 | 205 | — |
| 85 | N-ethyl-o-toluidine* | 70 | 182 | — |
| 86 | p-toluidine* | 70 | 184 | — |
| | Diamines | | | |
| 87 | 1,8-diamino-p-menthane | 70 | 188 | — |
| 88 | N-erucyl-1,3-propane* diamine | 70 | 220 | — |
| | Miscellaneous Amines | | | |
| 89 | branched tetramine L-PS (9)* | 70 | 242 | — |
| 90 | cyclododecylamine* | 70 | 159 | — |
| | Amides | | | |
| 91 | cocoamide*(10) | 70 | 245 | — |
| 92 | N,N-diethyltoluamide | 70 | 262 | IR |
| 93 | erucamide*(11) | 70 | 250 | L, P |
| 94 | hydrogenated tallow-amide* | 70 | 250 | L, P |
| 95 | octadecylamide(12) | 70 | 260 | L, P |
| 96 | N-trimethylol ropane stearamide | 70 | 255 | L, P |
| | Aliphatic Saturated Esters | | | |
| 97 | ethyl laurate* | 70 | 175 | — |
| 98 | ethyl palmitate* | 70 | 171 | — |
| 99 | isobutyl stearate* | 70 | 194 | L |
| 100 | isopropyl myristate* | 70 | 192 | — |
| 101 | isopropyl palmitate* | 70 | 285 | — |
| 102 | methyl caprylate | 70 | 182 | — |
| 103 | methyl stearate* | 70 | 195 | — |
| 104 | tridecyl stearate | 70 | 202 | L |
| | Aliphatic Unsaturated Esters | | | |
| 105 | butyloleate* | 70 | 196 | L |
| 106 | butylundecylenate* | 70 | 205 | — |
| 107 | stearylacrylate* | 70 | 205 | — |
| | Alkoxy Esters | | | |
| 108 | butoxyethyl oleate* | 70 | 200 | — |
| 109 | butoxyethyl stearate* | 70 | 205 | — |
| | Aromatic Esters | | | |
| 110 | benzylacetate | 70 | 198 | — |
| 111 | benzylbenzoate* | 70 | 242 | L, P |
| 112 | butylbenzoate* | 70 | 178 | L, P |
| 113 | ethylbenzoate* | 70 | 200 | L, P |
| 114 | isobutylphenylstearate* | 70 | 178 | L, P |
| 115 | methylbenzoate* | 70 | 170 | L, P |
| 116 | methylsalicylate* | 70 | 200 | L, P, PF |
| 117 | phenyllaurate* | 70 | 205 | L, P |
| 118 | phenylsalicylate | 70 | 211 | L, P, M, F |
| 119 | tridecylphenylstearate* | 70 | 215 | L, P |
| 120 | vinylphenylstearate* | 70 | 225 | L, P |
| | Diesters | | | |
| 121 | dibutylphthalate* | 70 | 290 | L, P |
| 122 | dibutyl sebacate* | 70 | 238 | L, P |
| 123 | dicapryl adipate | 70 | 204 | L, P |
| 124 | dicapryl phthalate | 70 | 204 | — |
| 125 | dicapryl sebacate | 70 | 206 | L, P |
| 126 | diethylphthalate* | 70 | 280 | IR |
| 127 | dihexylsebacate | 70 | 226 | — |
| 128 | dimethylphenylene distearate* | 70 | 208 | — |
| 129 | dioctyl maleate | 70 | 220 | — |
| 130 | di-iso-octyl phthalate | 70 | 212 | — |
| 131 | di-iso-octyl sebacate | 70 | 238 | — |
| | Esters-Polyethylene Glycol | | | |
| 132 | PEG 400 diphenylstearate | 70 | 326 | — |
| | Polyhydroxylic Esters | | | |
| 133 | castor oil | 70 | 270 | — |
| 134 | glycerol dioleate*(13) | 70 | 230 | AF |
| 135 | glycerol distearate*(14) | 70 | 201 | AF |
| 136 | glycerol monooleate*(15) | 70 | 232 | AF |
| 137 | glycerol monophenyl-stearate | 70 | 268 | — |
| 138 | glycerol monostearate* (16) | 70 | 211 | AF |

TABLE VI-continued

LDPE

| Ex. No.[1] | Liquid Type and Liquid | % Liq. | °C. | Type of Functional Liquid |
|---|---|---|---|---|
| 139 | trimethylolpropane monophenylstearate | 70 | 260 | — |
| | Ethers | | | |
| 140 | dibenzylether* | 70 | 189 | PF |
| 141 | diphenylether* | 75 | 200 | — |
| | Halogenated Ethers | | | |
| 142 | 4-bromodiphenylether* | 70 | 180 | FR |
| 143 | FR 300 BA[17] | 70 | 314 | FR |
| 144 | hexachlorocyclopentadiene* | 70 | 196 | PE, FR |
| 145 | octabromobiphenyl* | 70 | 290 | FR |
| | Terminal Double Bond Hydrocarbon | | | |
| 146 | 1-nonene* | 70 | 174 | L |
| | Internal Double Bond Hydrocarbon | | | |
| 147 | 3-eicosene* | 70 | 204 | — |
| 148 | 2-heptadecene* | 70 | 222 | — |
| 149 | 2-nonadecene* | 70 | 214 | — |
| 150 | 9-nonadecene* | 70 | 199 | — |
| 151 | 2-nonene* | 70 | 144 | L |
| 152 | 2-undecene | 70 | 196 | — |
| | Aromatic Hydrocarbons | | | |
| 153 | diphenylmethane | 75 | 200 | PF |
| 154 | trans-stilbene* | 70 | 218 | — |
| 155 | triphenylmethane | 70 | 225 | — |
| | Aliphatic Ketones | | | |
| 156 | dinonylketone* | 70 | 206 | — |
| 157 | distearylketone* | 70 | 238 | — |
| 158 | 2-heptadecanone | 70 | 205 | — |
| 159 | 8-heptadecanone* | 70 | 183 | — |
| 160 | 2-heptanone* | 70 | 152 | — |
| 161 | methylheptadecyl ketone* | 70 | 225 | — |
| 162 | methylnonyl ketone* | 70 | 170 | AR |
| 163 | methylpentadecyl ketone* | 70 | 210 | AR |
| 164 | methylundecyl ketone | 70 | 205 | — |
| 165 | 2-nonadecanone | 70 | 214 | — |
| 166 | 10-nonadecanone | 70 | 194 | — |
| 167 | 8-pentadecanone* | 70 | 178 | — |
| 168 | 11-pentadecanone* | 70 | 262 | — |
| 169 | 2-tridecanone* | 70 | 168 | — |
| 170 | 6-tridecanone* | 70 | 205 | — |
| 171 | 6-undecanone* | 70 | 188 | — |
| | Aromatic Ketones | | | |
| 172 | acetophenone* | 70 | 190 | PF |
| 173 | benzophenone | 70 | 245 | PF |
| | Miscellaneous Ketones | | | |
| 174 | 9-xanthone* | 70 | 220 | PE |
| | Phosphorous Compounds | | | |
| 175 | trixylenyl phosphate* | 70 | 304 | FR |
| | Miscellaneous | | | |
| 176 | N,N-bis(2-hydroxyethyl) tallowamine* | 70 | 210 | — |
| 177 | bath oil fragrance #5864K | 70 | 183 | FG |
| 178 | EC-53 Styrenated nonyl phenol[18]* | 70 | 191 | AO |
| 179 | Mineral oil | 50 | 200 | L |
| 180 | Muget hyacinth | 70 | 178 | FG |
| 181 | Phosclere P315C* | 70 | 200 | — |
| 182 | Phosclere P576[19]* | 70 | 210 | AO |
| 183 | Quinalidine | 70 | 173 | — |
| 184 | Quinoline* | 70 | 230 | — |
| 185 | Terpineol Prime No. 1 | 70 | 194 | M, PF |
| 186 | Firemaster BP-6 | 75 | 200 | FR |
| 187 | benzylalcohol/1-heptadecanol (50/50)* | 70 | 204 | — |
| 188 | benzylalcohol/1-heptadecanol (75/25)* | 70 | 194 | — |

*The liquid was extracted from the solid.
[1]Union Carbide Company's "Bakelite" polyethylene having the following properties was used: Density, g/cm$^3$, 0.922; Melt Index, g/10 min., 21.
[2]This is an acid with a density of 0.8602 g/cc and a melting point of 33°-34° C.
[3]Arizona Chemical Company's trademark for a mixture of fatty acids. The composition and physical properties are: Fatty Acid Composition (98.2% of total); Linoleic, Non-conjugated, %, 6; Oleic, %; 47; Saturated, %, 3; Other fatty acids, %, 8; Specific Gravity, 25/25° C., 0.898; Viscosity, SSU, 100° F., 94.
[4]Shell Chemical Company's trademark for its synthetic fatty alcohol of 12-15 carbon atoms.
[5]Croda, Inc.'s, Volpo 3 surfactant having the following properties was used: Acid Value, max., 2.0; Haze Pt., 1% aq. soln., insoluble; HLB value, calculated, 6.6; Iodine Value, Wijs, 57-62; pH of 3% aq. soln., 6-7; hydroxyl value, 135-150.
[6]Union Carbide Company's trademark for its glycol having the following properties; Apparent Specific Gravity, 20/20° C., 1.009; Avg. hydroxyl number, mg. KOH/g, 265; Acid Number, mg KOH per g sample, max., 0.2; pH at 25° C. in 10:6 isopropanol water soln., 4.5-6.5.
[7]A tertiary amine having the following properties was used: Cloud point, °F., ASTM 100; Specific Gravity, 25/4° C., 0.813; Viscosity, SSU, at 25° C., 59.3.
[8]A tertiary amine having the following properties was used: Melting Range, °F., 28 to 41: Cloud Point, °F., 60; Specific Gravity, 25/4° C., 0.803; Viscosity, SSU, 25° C., 47.
[9]N-phenylstearo 5, 9, 13 azatridecane.
[10]An aliphatic amide having the following properties was used: Appearance, Flake.; Flash Point, °C., Approx., 174; Fire Point, °C., Approx., 185.
[11]An amide having the following properties was used: Specific Gravity, .88; Melting Pt., °C., 99-109; Flash Pt., °C., 225.
[12]Octadecylamide having the following properties was used: Appearance, Flake; Flash Point, °C., Approx., 225; Fire Point, °C., Approx. 250.
[13]A glycerol ester having the following properties was used Flash Point, COC, °F., 520; Freezing Point, °C., 0; Viscosity at 25° C., cp, 90; Specific Gravity 25/20° C., 0.923-0.929.
[14]A solid with a melting point of 29.1° C.
[15]A glycerol ester having the following properties was used: Specific Gravity, 0.94-0.953; Flash Point, COC, °F., 435; Freezing Point, °C., 20; Viscosity at 25° C., cp, 204.
[16]A glycerol ester having the following properties was used: Form at 25° C., Flakes; Flash Point, COC, °F., 410; Melting Point, °C., 56.5-58.5.
[17]Dow Chemical Company's trademark for its decabromodiphenyl oxide fire retardant having the following properties was used: Bromine, %, 81-83; Melting Point, min. 285° C.; Decomposition Temp., DTA, 425° C.
[18]Akzo Chemie Nv.'s trademark for its styrenated hindered phenol.
[19]Akzo Chemie Nv.'s styrenated hindered phenol.

Photomicrographs of the porous polymers of Examples 38 and 122 are illustrated in FIGS. 28 and 29, respectively. The photomicrographs, at 2000X amplification, show the cellular structure with a significant amount of "foliage" uniformly present throughout the samples.

EXAMPLES 189 to 193

Examples 190 through 194 in Table VII illustrate the formation of homogeneous porous polymer intermediates, by pouring the solution into a glass dish to form cylindrical blocks having a radius of about 1.75 inches and a depth of about 0.25 inch, except where indicated, from "Noryl" polymer and the compatible liquids found to be useful, using the standard preparation procedure. In the indicated instances, the microporous polymer was likewise prepared.

The details of preparation and the type of functionally useful liquid noted are set forth in Table VII:

TABLE VII

| Ex. No.[1] | Liquid Type and Liquid | % Liq. | °C. | Type of Functional Liquid |
|---|---|---|---|---|
| | Aromatic Amine | | | |
| 189 | diphenylamine | 75 | 195 | PE, AO |
| | Diester | | | |
| 190 | dibutylphthalate | 75 | 210 | L |
| | Halogenated Hydrocarbon | | | |
| 191 | hexabromobiphenyl[2] | 70 | 315 | FR |
| | Miscellaneous | | | |

TABLE VII-continued

| Ex. No.(1) | Liquid Type and Liquid | % Liq. | °C. | Type of Functional Liquid |
|---|---|---|---|---|
| 192 | N,N-bis(2-hydroxyethyl) tallowamine* | 75 | 250 | — |
| 193 | N,N-bis(2-hydroxyethyl) tallowamine | 90 | 300 | — |

(1)General Electric Company's "Noryl", a blend of polyphenylene oxide condensation polymer with polystyrene, having the following properties was used: Specific Gravity, 73° F., 1.06; Tensile Strength, psi. at 73° F., 9,600; Elongation at break, % at 73° F., 60; Tensile Modulus, psi. at 73° F., 355,000; and Rockwell Hardness, R119.
(2)The "Noryl" microporous polymers formed with hexabromo biphenyl and N,N-bis(2-hydroxyethyl) tallowamine were poured to depths of 0.5 inch.

A photomicrograph of the microporous polymer of Example 192 is illustrated in FIG. 25. The photomicrograph, at 2500X amplification, shows the microcellular structure with spherical resin deposits on the walls of the cells.

EXAMPLES 194 to 236

Examples 194 through 236 in Table VIII illustrate the formation of homogeneous porous polymer intermediates, in the form of cylindrical blocks having a radius of about 1.25 inches and a depth of about 0.5 inch, from polypropylene ("PP") and the compatible liquids found to be useful, using the standard preparation procedure. In addition, in the indicated examples, blocks of about 6 inches in depth and/or thin films were made. Also, as indicated, the microporous polymer was prepared.

The details of preparation and the type of functionally useful liquid noted are set forth in Table VIII:

TABLE VIII

PP

| Ex. No. (1) | Liquid Type and Liquid | % Liq. | °C. | Type of Functional Liquid | Thin Film |
|---|---|---|---|---|---|
| | Unsaturated Acid | | | | |
| 194 | 10-undecenoic acid* | 70 | 260 | M | |
| | Alcohols | | | | |
| 195 | 2-benzylamino-1-propanol | 70 | 260 | — | |
| 196 | Ionol CP* | 70 | 160 | AO | |
| 197 | 3-phenyl-1-propanol | 75 | 230 | — | |
| 198 | salicylaldehyde | 70 | 185 | PF | |
| | Amides | | | | |
| 199 | N,N-diethyl-m-toluamide | 75 | 240 | IR | |
| | Amines | | | | |
| 200 | aminodiphenylmethane* | 70 | 230 | — | |
| 201 | benzylamine* | 70 | 160 | — | |
| 202 | N-butylaniline | 75 | 200 | — | |
| 203 | 1,12-diaminododecane* | 70 | 180 | — | |
| 204 | 1,8-diaminooctane | 70 | 180 | — | |
| 205 | dibenzylamine* | 75 | 200 | — | |
| 206 | N,N-diethanolhexylamine* | 75 | 260 | — | |
| 207 | N,N-diethanoloctylamine* | 75 | 250 | — | |
| 208 | N,N-bis-β-hydroxyethyl cyclohexylamine | 75 | 280 | — | |
| 209 | N,N-bis-(2-hydroxyethyl) hexylamine | 75 | 260 | — | |
| 210 | N,N-bis-(2-hydroxyethyl) octylamine | 75 | 260 | — | |
| | Esters | | | | |
| 211 | benzylacetate* | 75 | 200 | — | — |
| 212 | benzylbenzoate* | 75 | 235 | L, P, PF | — |
| 213 | butylbenzoate | 75 | 190 | L, P | — |
| 214 | dibutylphthalate* | 75 | 230 | L, P | yes |
| 215 | methylbenzoate | 70 | 190 | L, P, PF | — |
| 216 | methylsalicylate* | 75 | 215 | L, P, PF | — |
| 217 | phenylsalicylate* | 70 | 240 | P | — |
| | Ethers | | | | |

TABLE VIII-continued

PP

| Ex. No. (1) | Liquid Type and Liquid | % Liq. | °C. | Type of Functional Liquid | Thin Film |
|---|---|---|---|---|---|
| 218 | dibenzylether | 75 | 210 | PF | — |
| 219 | diphenylether* | 75 | 200 | PF | yes |
| | Halocarbons | | | | |
| 220 | 4-bromodiphenylether* | 70 | 200 | FR | — |
| 221 | 1,1,2,2 tetrabromoethane* | 70 | 180 | FR | — |
| 222 | 1,1,2,2 tetrabromoethane* | 90 | 180 | FR | — |
| | Ketones | | | | |
| 223 | benzylacetone | 70 | 200 | — | — |
| 224 | methylnonylketone | 75 | 180 | — | — |
| | Miscellaneous | | | | |
| 225 | N,N-bis(2-hydroxethyl) tallowamine* (2) & (3) | 75 | 200 | — | yes |
| 226 | N,N-bis(2-hydroxyethyl) cocoamine (2) | 75 | 180 | — | — |
| 227 | butylated hydroxy toluene | 70 | 160 | AO | — |
| 228 | D.C. 550 Silicone Fluid (4) | 50 | 260 | S, L | — |
| 229 | D.C. 556 Silicone Fluid* | 70 | 190 | S, L | — |
| 230 | EC-53 | 75 | 210 | — | — |
| 231 | N-hydrogenated rapeseed diethanol amine* | 75 | 210 | SF | — |
| 232 | N-hydrogenated tallow diethanol amine | 75 | 225 | SF | — |
| 233 | Firemaster BP-6 | 75 | 200 | FR | — |
| 234 | NBC oil | 75 | 190 | — | — |
| 235 | Quinaldine* | 70 | 200 | — | — |
| 236 | Quinoline* | 75 | 220 | M | — |

*The liquid was extracted from the solid.
(1) Dow Corning's trademark for its phenylmethyl polysiloxane having the following properties was used: Viscosity 115CS and serviceable from −40 to 450° F. in open systems, and to 600° F. in closed systems.
(2) A block of about 6 inches in depth was also prepared
(3) A permanent internal antistatic agent, having the following physical properties was used: Boiling Point, 1mm Hg, °C., 170; Viscosity, SSU, 90° F., 367.
(4) Phillips Petroleum Company's "Marlex" polypropylene having the following properties was used: Density, g/cm³, 0.908; Melt Flow, g/10 min. Melting Point, °F., 340; Tensile Strength at yield, psi, 2"/min., 5000; Hardness Shore D, 73.

Photomicrographs of the porous polymer of Example 225 are illustrated in FIGS. 2 through 5. The photomicrographs of FIGS. 2 and 3, at 55X and 550X amplification, respectively, show the macro structure of the microporous polymer. The photomicrographs of FIGS. 4 and 5, at 2,200X and 5,500X amplification, respectively, show the microcellular structure of the polymer as well as the interconnecting pores.

EXAMPLES 237 to 243

Examples 237 through 243 in Table IX illustrate the formation of homogeneous porous polymer intermediates, in the form of cylindrical blocks having a radius of about 1.25 inches and a depth of about 0.5 inch, from polyvinylchloride ("PVC") and the compatible liquids found to be useful, using the standard preparation procedure. Many of the exemplified intermediates were extracted to form porous polymers, as indicated in the Table.

The details of preparation and the type of functionally useful liquid notes are set forth in Table IX:

TABLE IX

PVC

| Ex. No.[1] | Liquid Type and Liquid | % Liq. | °C. | Type of Functional Liquid |
|---|---|---|---|---|
| | Aromatic Alcohols | | | |
| 237 | 4-methoxybenzyl-alcohol* | 70 | 150 | PF |
| | Other —(OH) containing Compounds | | | |
| 238 | 1-3,-dichloro-2-propanol* | 70 | 170 | — |
| 239 | menthol* | 70 | 180 | PF |
| 240 | 10-undecene-1-ol* | 70 | 204–210 | — |
| | Halogenated | | | |
| 241 | Firemaster T33P*[2] | 70 | 165 | FR |
| 242 | Firemaster T13P*[3] | 70 | 175 | FR |
| | Aromatic Hydrocarbons | | | |
| 243 | trans-stilbene* | 70 | 190 | — |

*The liquid was extracted from the solid.
[1] The polyvinylchloride used was of dispersion grade made by American Hoechst, having an inherent viscosity of 1.20, a density of 1.40 and bulk density of 20.25 pounds per cubic foot.
[2] Michigan Chemical Corporation's trademark for its tris (1,3-dichloroisopropyl) phosphate fire retardant having the following properties: Chlorine content, theoretical, %, 49.1; Phosphorous content, theoretical, %, 7.2; Boiling Point, 4mm Hg, abs. °C., 200 (decomposes at 200° C.); Refractive Index, 1.50.9; Viscosity, Brookfield, 73° F., Centipoises, 2120. Structure: [(ClCH$_2$)$_2$CHO]$_3$ P—O
[3] Michigan Chemical Corporation's trademark for its tris-halogenated propylphosphate flame retardant having the following properties: Specific Gravity, at 25° C./25° C., 1.88; Viscosity, at 25° C., centistokes, 1928; Refractive Index, 1.540; pH, 6.4; Chlorine, %, 18.9; Bromine, %, 42.5; Phosphorous, %, 5.5.

A photomicrograph of the porous polymer of Example 242 is illustrated in FIG. 27. The photomicrograph, at 2000X amplification, shows the extremely small cell size of this microporous polymer in contrast to the cell structure exemplified by FIGS. 7, 13, 18, 20, and 24, wherein the cell size is larger and more readily observable at a comparable magnification. The photomicrograph also shows the presence of a large amount of resin masking the basic cell structure.

EXAMPLES 244 to 255

Examples 244 through 255 in Table X illustrate the formation of homogeneous porous polymer intermediates, in the form of cylindrical blocks having a radius of about 1.25 inches and a depth of about 2.0 inches, from methylpentene ("MPP") polymer and the compatible liquids found to be useful, using the standard preparation procedure. Many of the exemplified intermediates were extracted to form porous polymers, as indicated in the Table.

The details of preparation and the type of functionally useful liquid noted are set forth in Table X:

TABLE X

MPP

| Ex. No.[1] | Liquid Type and Liquid | % Liq. | °C. | Type of Functional Liquid |
|---|---|---|---|---|
| | Saturated Aliphatic Acid | | | |
| 244 | decanoic acid* | 75 | 230 | — |
| | Saturated Alcohols | | | |
| 245 | 1-dodecanol* | 75 | 230 | — |
| 246 | 2-undecanol* | 75 | 230 | — |
| 247 | 6-undecanol* | 75 | 230 | — |
| | Amine | | | |
| 248 | dodecylamine | 75 | 230 | FA |
| | Esters | | | |
| 249 | butylbenzoate* | 75 | 210 | L, P, PF |
| 250 | dihexylsebacate* | 70 | 220 | L, P |
| | Ethers | | | |
| 251 | dibenzylether* | 70 | 230 | PF |

TABLE X-continued

MPP

| Ex. No.[1] | Liquid Type and Liquid | % Liq. | °C. | Type of Functional Liquid |
|---|---|---|---|---|
| | Hydrocarbons | | | |
| 252 | 1-hexadecene* | 75 | 220 | — |
| 253 | naphthalene* | 70 | 240 | MR |
| | Miscellaneous | | | |
| 254 | EC-53* | 75 | 230 | AO |
| 255 | Phosclere P315C* | 75 | 250 | — |

*The liquid was extracted from the solid.
[1] Mitsui's methylpentene polymer having the following properties was used: Density, g.cc, 0.835; Melting Point °C., 235; Tensile Strength at Break, kg/cm$^2$, 230; Elongation at Break %, 30, Rockwell Hardness, R, 85.

A photomicrograph of the porous polymer of Example 253 is illustrated in FIG. 22. The photomicrograph, at 2400X amplification, shows the extremely flattened cell walls, as comparable to the configuration observed in FIG. 14.

EXAMPLES 256 to 266

Examples 256 through 266 in Table XI illustrate the formation of homogeneous porous polymer intermediates, in the form of cylindrical blocks having a radius of about 1.25 inches and a depth of about 0.5 inch, from polystyrene ("PS") and the compatible liquids found to be useful, using the standard preparation procedure. All of the exemplified intermediates were extracted to form porous polymers.

The details of preparation and the type of functionally useful liquid noted are set forth in Table XI.

TABLE XI

| Ex. No. (1) | Liquid Type and Liquid | % Liq. | °C. | Type of Functional Liquid |
|---|---|---|---|---|
| 256 | Firemaster T-13P | 70 | 250 | FR |
| 257 | hexabromobiphenyl | 70 | 260 | FR |
| 258 | Phosclere P315C | 70 | 270 | — |
| 259 | Phosclere P576 | 70 | 285 | AO |
| 260 | tribromoneopentylalcohol | 70 | 210 | FR |
| 261 | FR 2249 (2) | 70 | 240 | FR |
| 262 | Fyrol CEF (3) | 70 | 250 | FR |
| 263 | Firemaster T33P (4) | 70 | 210 | FR |
| 264 | Fyrol FR 2 (5) | 70 | 240 | FR |
| 265 | dichlorobenzene | 80 | 160 | MR, FR |
| 266 | 1-dodecanol | 75 | — | — |

(1) Monsanto Chemical Company's "Lustrex" polystyrene having the following physical properties was used: Impact Strength, ft. lbs./in notch (Inj. molded), 0.40; Tensile Strength, psi, 7500; Elongation, %, 2.5; Elastic Modulus, psi, XID$^5$, 4.5; Deflection Temp., under load 264, psi, °F., 200; Specific Gravity, 1.05; Rockwell Hardness, M-75; Melt Flow, g/10 min., 4.5.
(2) Dow Chemical Corporation's trademark for its fire retardant having composition and properties: Tribromoneopentyl alcohol, 60%; Voranol CP. 3000 polyol, 40%; Bromine, %, 43; hydroxyl No. 130; Viscosity, cps, 25° C. (approx.) 1600; Density, gm/cc, 1.45.
(3) Stauffer Chemical Company's trademark for its tris- -chloro-ethyl phosphate fire retardant having the following properties: Boiling Point, at 0.5 mm Hg abs., °C., 145, at 760 mm hg abs., °C., decomposes; Chlorine content, wt. %, 36.7; Phosphorous content, wt. %, 10.8; Refractive Index at 20° C., 1.4745; Viscosity, cps at 73° F. (22.8° C.), 40.
(4) Michigan Chemical Corporation's trademark for its tris(1,3-dichloroisopropyl phosphate) fire retardant having the following properties; Chlorine content, theoretical, %, 49.1; Phosphorous content, theoretical, & 7.2; Boiling Point, 4 mm Hg abs., °C. 200 (decomposes at 200° C.); Refractive Index, 1.5019; Viscosity, Brookfield, 73° F., Centipoises, 2120.
Structure: [(ClCH$_2$)$_2$CHO]$_3$ P—O
(5) Stauffer Chemical Company's trademark for its tris (dichloro-propyl) phosphate flame retardant additive having the following properties: Melting Point, °F., Approx., 80; Refractive Index n$_d$ at 25° C., 1.5019; Viscosity, Brookfield at 22.8° C., cps, 2120.

A photomicrograph of the microporous polymer of Example 260 is illustrated in FIG. 26. Although the cells are small compared to the cells illustrated in FIGS.

4, 7, 13, 18, and 25, the basic microcellular structure is present.

EXAMPLE 267

This example illustrates the formation of a homogeneous porous polymer intermediate from 30% high impact polystyrene (1) and 70% hexabromobiphenyl, using the standard preparation procedure and heating the mixture to 280° C. The polymer intermediate thus formed was about 2.5 inches in diameter and about 0.5 inch in depth. The hexabromobiphenyl is useful as a flame retardant and the porous intermediate is useful as a solid flame retardant additive.

(1) Union Carbide Company's "Bakelite" polystyrene for injection molding having the following properties was used: Tensile strength, psi., (⅛" thick) 5000, ultimate elongation, (⅛" thick) 25; Tensile modulus, psi., (⅛" thick) 380,000; Rockwell hardness (¼×½×5") 90; Specific Gravity, natural 1.04.

EXAMPLE 268

This Example illustrates the formation of a homogeneous porous polymer intermediate from 25% acrylonitrile-butadiene-styrene terpolymer (2) and 75% diphenylamine, using the standard preparation procedure and heating the mixture to 220° C. The polymer intermediate thus formed was about 2.5 inches in diameter and about 2 inches in depth. The microporous polymer was formed by extracting the diphenylamine. The diphenylamine is useful as a pesticide and antioxidant and the porous polymer intermediate has the same utility.

(2) Uniroyal's Kralastic ABS polymer having the following properties was used: Specific Gravity, 1.07; impact strength (⅛" Bar Sample), Izod Notched, 73° F., ft. lbs./in. notch, 1.3-1.9; Tensile Strength, psi., 8,800; and Rockwell Hardness, R, 118.

EXAMPLES 269 and 270

The homogeneous porous polymer intermediates were formed from 25% chlorinated polyethylene thermoplastic supplied by Dow, having a melt viscosity of 15 poise, 8 percent crystallinity, and containing 36 percent chlorine and 75% N,N-bis(2-hydroxyethyl) tallowamine (Example 270) and 75% chlorinated polyethylene thermoplastic and 25% 1-dodecanol (Example 271), using the standard preparation procedure and heating to 220° C. The porous polymer intermediates were about 2.5 inches in diameter and about 2 inches in depth.

EXAMPLE 271

The homogeneous porous polymer intermediate was formed using the standard preparation procedure and heating to 210° C. from 25% chlorinated polyethylene elastomer, as used in Example 271 and 75% diphenylether. The porous polymer intermediates were about 2.5 inches in diameter and about 2 inches in depth. The diphenylether is useful as a perfume and the intermediate is also useful in perfumes.

EXAMPLES 272 to 275

Examples 272 through 275 in Table XII illustrate the formation of homogeneous porous polymer intermediates, in the form of cylindrical blocks having a radius of about 1.25 inches and a depth of about 0.5 inch from styrene-butadiene ("SBR") rubber (1) and the compatible liquids found to be useful using the standard preparation procedure. In addition to the cylindrical blocks, as indicated, thin films were also formed.

(1) Shell Chemical Company's Kraton SBR polymer having the following properties was used: Tensile Strength, psi., 3100-4600; Elongation at Break, 880-1300; and Rockwell Hardness, Shore A, 35-70.

The details of preparation and the type of functionally useful liquid noted are set forth in Table XII:

TABLE XII

| | SBR | | | | |
|---|---|---|---|---|---|
| Ex. No. | Liq. Type and Liquid | % Liq. | °C. | Type of Functional Liquid | Thin Film |
| 272 | N,N-bis(2-hydroxyethyl) tallowamine | 80 | 195 | — | yes |
| 273 | decanol* | 70 | 190 | PF | yes |
| 274 | diphenylamine | 70 | 200-210 | PE, AO | yes |
| 275 | diphenylether | 70 | 195 | PF | yes |

*The liquid was extracted from the solid.

EXAMPLES 276 to 278

Examples 277 through 279 in Table XIII illustrate the formation of homogeneous porous polymer intermediates, in the form of cylindrical blocks having a radius of 1.25 inches and a depth of about 0.5 inch from "Surlyn" (1) and the compatible liquids found to be useful, using the standard preparation procedure. In addition to the cylindrical blocks, as indicated, thin films were also formed. Two of the exemplified intermediates were extracted to form porous polymers, as indicated in the Table.

(1) E. I. du Pont de Nemour's "Surlyn" ionomer resin 1652, lot number 115478, having the following properties was used: Density, g/cc, 0.939; Melt Flow Index, deci m./min., 4.4; Tensile Strength, psi., 2850; Yield Strength, psi., 1870; Elongation, %, 580.

The details of preparation and the type of functionally useful liquid noted are set forth in Table XIII:

TABLE XIII

| | SURLYN | | | | |
|---|---|---|---|---|---|
| Ex. No. (1) | Liq. Type and Liquid | % Liq. | °C. | Type of Functional Liquid | Thin Film |
| 276 | N,N-bis(2-hydroxyethyl) tallowamine | 70 | 190 195 | — | yes |
| 277 | diphenylether* | 70 | 200 | PF | yes |
| 278 | dibutylphthalate | 70 | 195 | L | yes |

*The liquid was extracted from the solid.

Photomicrographs of the porous polymer of Example 277 are illustrated in FIGS. 23 and 24. FIG. 23, at 255X amplification, shows the macrostructure of the polymer. FIG. 24, at 2550X amplification, illustrates the microcellular structure of the polymer with slight "foliage" and relatively thick cell walls, as compared with, for example, FIG. 25.

EXAMPLE 279

The homogeneous porous polymer intermediate was formed, using the standard preparation procedure and heating to 200° C., from a high density polyethylene-chlorinated polyethylene blend, equal parts, and 75% 1-dodecanol. The porous polymer intermediate was cast in a film having a thickness of about 20 to 25 mils. The HDPE and CPE were utilized in previous Examples.

EXAMPLE 280

The homogeneous porous polymer intermediate was formed, using the standard preparation procedure and heating to 200° C., from a high density polyethylene-polyvinylchloride blend, equal parts, and 75% 1-dodecanol. The intermediate thus formed was about 2 inches in depth and about 2.5 inches in diameter. The HDPE and PVC were as utilized in previous Examples.

EXAMPLE 281

The homogeneous porous polymer intermediate was formed, using the standard preparation procedure and heating to 200° C., from a high density polyethylene/acrylonitrile-butadiene-styrene terpolymer blend, equal parts, and 75% 1-dodecanol. The intermediate thus formed was about 2 inches in depth and about 2.5 inches in diameter. The HDPE and ABS were as utilized in previous Examples.

EXAMPLES 282 to 285

Examples 282 through 285 in Table XIV illustrate the formation of homogeneous porous polymer intermediates, in the form of cylindrical blocks having a radius of 1.25 inches and a depth of about 2 inches, from low density polyethylene/chlorinated polyethylene blend, equal parts, and the compatible liquids found to be useful, using the standard preparation procedure. In Example 283, the aforementioned method was employed, but the intermediate was cast into a film having a thickness of about 20 to 25 mils. The LDPE and CPE were as utilized in previous Examples.

The details of preparation and the type of functionally useful liquid noted are set forth in Table XIV:

TABLE XIV

| Ex. No. | Liquid Type and Liquid | % Liq. | °C. | Type of Functional Liquid |
|---|---|---|---|---|
| 282 | 1-dodecanol | 75 | 200 | — |
| 283 | diphenylether | 75 | 200 | PF |
| 284 | diphenylether | 50 | 200 | PF |
| 285 | N,N-bis(2-hydroxyethyl) tallowamine | 75 | 200 | — |

EXAMPLES 286 and 287

The homogeneous porous polymer intermediates were formed from a low density polyethylene/polypropylene blend, equal parts, and 75% N,N-bis (2-hydroxyethyl) tallowamine (Example 286) and low density polyethylene/polypropylene blend, equal parts, and 50% N,N-bis (2-hydroxyethyl) tallowamine (Example 287) using the standard preparation procedure and heating to 220° C. for Example 286 and to 270° C. for Example 288. Both porous polymer intermediates were about 2.5 inches in diameter and about 2 inches in depth. The LDPE and PP were as utilized in previous Examples.

EXAMPLE 288

The homogeneous porous polymer intermediate was formed, using the standard preparation procedure and heating to 200° C., from 50% N,N-bis(2-hydroxyethyl) tallowamine and 50% polypropylene/polystyrene blend (25 parts polypropylene). The porous polymer intermediates were about 2.5 inches in diameter and about 2 inches in depth. The PP and PS were as utilized in previous Examples.

EXAMPLE 289

The homogeneous porous polymer intermediate was formed, using the standard preparation procedure and heating to 200° C., from 75% 1-dodecanol and a polypropylene/chlorinated polyethylene blend, equal parts. The porous polymer intermediate was about 2.5 inches in diameter and about 0.5 inch in depth. The PP and CEP were as utilized in previous Examples.

EXAMPLES 290 to 300

Examples 290 through 300 illustrate the polymer-compatible liquid concentration range useful for the formation of a homogeneous porous polymer intermediate from high density polyethylene and N,N-bis(2-hydroxyethyl) tallowamine. In each Example the intermediates were about 2 inches in depth and about 2.5 inches in diameter. The HDPE was as utilized in previous Examples.

The details of preparation and any physical characteristics noted are set forth in Table XV:

TABLE XV

| Ex. No. | % Liq. | °C. | Remarks |
|---|---|---|---|
| 290 | 95 | 275 | very weak; no solid integrity; not operable |
| 291 | 90 | — | very greasy; liquid leaching out; upper liquid limit was exceeded |
| 292 | 80 | 250 | greasy |
| 293 | 75 | 220 | greasy |
| 294 | 70 | 250 | hard solid |
| 295 | 65 | 220 | — |
| 296 | 60 | 250 | hard solid |
| 297 | 55 | 220 | — |
| 298 | 50 | 240-260 | hard solid |
| 299 | 40 | 260 | hard solid |
| 300 | 30 | 200 | hard solid |

A photomicrograph of the porous polymer of Example 300 is illustrated in FIG. 19, at 2000X amplification. The cells are not clearly visible at this amplification. FIG. 19 can be compared to FIG. 17, at 2475X amplification, wherein the cell sizes are also very small at a similar polymer concentration of 70%.

EXAMPLES 301 to 311

These Examples illustrate the polymer-compatible liquid concentration range useful for the formation of a homogeneous porous polymer intermediate from low density polyethylene and N,N-bis(2-hydroxyethyl) tallowamine. In each example the intermediate was about 0.5 inch in depth and about 2.5 inches in diameter. The LDPE was as utilized in previous Examples.

The details of preparation and any physical characteristics noted are set forth in Table XVI:

TABLE XVI

| Ex. No. | % Liq. | °C. | Remarks |
|---|---|---|---|
| 301 | 95 | 275 | very weak, no solid integrity; not operable |
| 302 | 90 | 240 | very greasy; liquid leaching out; upper liquid limit was exceeded |
| 303 | 80 | 260 | hard solid |
| 304 | 75 | 210 | hard solid |
| 305 | 70 | 210 | hard solid |
| 306 | 66 | 200 | hard solid |
| 307 | 60 | 280 | hard solid |
| 308 | 50 | 280-290 | hard solid |
| 309 | 40 | 285 | hard solid |
| 310 | 30 | 285 | hard solid |
| 311 | 20 | 280-300 | hard solid |

Photomicrographs of the porous polymers of Examples 303, 307 and 310 are illustrated in FIGS. 14-15 (at 250X and 2500X amplification, respectively), 16 (at 2500X amplification), and 17 (at 2475X amplification), respectively. The Figures show the decreasing cell size, from very large (FIG. 15, 20% polymer) to very small (FIG. 17, 70% polymer), with increasing polymer content. The relatively flattened cell walls of the 20% polymer, Example 303, are similar to the methyl pentene polymer (FIG. 22) and are observable in FIG. 14. FIG. 15 is an enlargement showing part of a cell wall illustrated in FIG. 14. The microcellular structure of the porous polymer is observable in FIG. 16.

EXAMPLES 312 to 316

Examples 312 to 316 illustrate the polymer-compatible liquid concentration range useful for the formation of a homogeneous porous polymer intermediate from low density polyethylene and diphenylether. In each Example the intermediate was about 0.5 inch in depth and about 2.5 inches in diameter. The LDPE was as utilized in previous Examples.

The details of preparation and any physical characteristics noted are set forth in Table XVII:

TABLE XVII

| Ex. No. | % Liq. | °C. | Remarks |
|---|---|---|---|
| 312 | 90 | 185 | very greasy; no solid integrity; not operable |
| 313 | 80 | 185 | very greasy; near upper liquid limit but still operable |
| 314 | 75 | 200 | wet; strong |
| 315 | 70 | 190–200 | slightly greasy |
| 316 | 60 | 200 | hard solid |

EXAMPLES 317 to 322

Examples 317 to 321 illustrate the polymer-compatible liquid concentration range useful for the formation of a homogeneous porous polymer intermediate from low density polyethylene and 1-hexadecene. In each Example the intermediate was about 2 inches in depth and about 2.5 inches in diameter. The LDPE was as utilized in previous Examples.

The details of preparation and any physical characteristics noted are set forth in Table XVIII:

TABLE XVIII

| Ex. No. | % Liq. | °C. | Remarks |
|---|---|---|---|
| 317 | 90 | 180 | good strength |
| 318 | 90 | 180 | little strength, operable |
| 319 | 75 | 200 | little strength, operable |
| 320 | 70 | 177 | — |
| 321 | 50 | 180 | good strength |

EXAMPLES 322 to 334

These Examples illustrate the polymer-liquid concentration range useful for the formation of a homogeneous porous polymer intermediate from polypropylene and N,N-bis(2-hydroxyethyl) tallowamine. In each Example the intermediate was about 0.5 inch in depth and 2.5 inches in diameter. In addition, as indicated, films were made. The PP was as utilized in previous Examples.

The details of preparation and any physical characteristics noted are set forth in Table XIX:

TABLE XIX

| Ex. No. | % Liq. | °C. | Remarks | Thin Film |
|---|---|---|---|---|
| 322 | 90 | 200 | quite wet | yes |
| 323 | 85 | 200 | — | — |
| 324 | 80 | 200 | strong | yes |
| 325 | 75 | 180 | dry and hard | yes |
| 326 | 70 | 200 | — | yes |
| 327 | 65 | 210 | — | — |
| 328 | 60 | 210 | — | yes |
| 329 | 50 | 200 | — | yes |
| 330 | 40 | 210 | — | yes |
| 331 | 36.8 | 175 | white-crystalline | — |
| 332 | 25 | 180 | — | — |
| 333 | 20 | 180 | — | yes |
| 334 | 15 | 180 | — | — |

Photomicrographs of Examples 322, 326, 328, 330 and 333 are illustrated in FIGS. 6 through 10, respectively (at 1325X, 1550X, 1620X, 1450X, and 1250X amplification, respectively). The extreme foliage of the 10% polymer microporous polymer is shown by FIG. 6, yet the microcellular structure is still maintained. These Figures illustrate the decreasing cell size as the amount of polymer is increased. However, the microcellular structure is present in each example despite the small cell size.

EXAMPLES 335 to 337

The Examples illustrate the polymer-compatible liquid concentration range useful for the formation of a homogeneous porous polymer intermediate from polypropylene and diphenylether. In each Example the intermediate was about 0.5 inch in depth and about 2.5 inches in diameter. In addition, as indicated, thin films were also made. The PP was as utilized in previous Examples.

The details of preparation and any physical characteristics noted are set forth in Table XX:

TABLE XX

| Ex. No. | % Liq. | °C. | Thin Film |
|---|---|---|---|
| 335 | 90 | 200 | yes |
| 336 | 80 | 200 | yes |
| 337 | 70 | 200 | yes |

Photomicrographs of the porous polymer of Examples 335, 336 and 337 are illustrated in FIGS. 11 (2000X amplification), 12 (2059X amplification) and 13 (1950X amplification). The Figures illustrate that as the polymer concentration is increased, the pore size decreases, FIG. 11 illustrates the smooth cell walls, while FIGS. 12 and 13 illustrate the cells and connecting pores. In each of the Figures, the microcellular structure is present.

EXAMPLES 338 to 346

These Examples illustrate the polymer-compatible liquid concentration range useful for the formation of a homogeneous porous polymer intermediate from styrene-butadiene rubber and N,N-bis(2-hydroxyethyl) tallowamine. In each Example the intermediate was about 0.5 inch in depth and 2.5 inches in diameter. In addition, as indicated, thin films were made. The SBR was as utilized in previous Examples.

The details of preparation and any physical characteristics noted are set forth in Table XXI:

TABLE XXI

| Ex. No. | % Liq. | °C. | Remarks | Thin Film |
|---|---|---|---|---|
| 338 | 90 | 200 | weak, beyond the upper liquid limit | yes |
| 339 | 80 | 195 | rubbery | yes |
| 340 | 75 | 195 | rubbery | yes |
| 341 | 70 | 195 | rubbery | yes |
| 342 | 60 | 200 | rubbery | yes |
| 343 | 50 | not reported | rubbery | yes |
| 344 | 40 | not reported | rubbery | yes |
| 345 | 30 | not reported | rubbery | yes |

TABLE XXI-continued

| Ex. No. | % Liq. | °C. | Remarks | Thin Film |
|---|---|---|---|---|
| 346 | 20 | not reported | rubbery | yes |

Photomicrographs for the styrene-butadiene rubber microporous polymer of Examples 339 and 340 are illustrated in FIGS. 20 (2550X amplification) and 21 (2575X amplification). The Figures illustrate the microcellular structure of the microporous polymers. FIG. 21 also shows the presence of spherical polymer deposits on the cell walls.

EXAMPLES 347 to 352

Examples 347 through 352 illustrate the polymer-compatible liquid concentration range useful for the formation of a homogeneous porous polymer intermediate from styrene-butadiene rubber and decanol. In each Example the intermediate was about 0.5 inch in depth and 2.5 inches in diameter. In addition, as indicated, thin films were made. The SBR was as utilized in previous Examples.

The details of preparation and any physical characteristics noted are set forth in Table XXII:

TABLE XXIII

| Ex. No. | % Liq. | °C. | Remarks |
|---|---|---|---|
| 353 | 80 | not reported | — |
| 354 | 70 | 200–210 | — |
| 355 | 60 | 215 | — |
| 356 | 50 | 200–210 | — |

EXAMPLES 357 to 361

Examples 357 through 361 illustrate the polymer-compatible liquid concentration range useful for the formation of a homogeneous porous polymer intermediate from a "Surlyn" resin as utilized in previous Examples and N,N-bis(hydroxyethyl) tallowamine. In each Example the intermediate was about 0.5 inch in depth and 2.5 inches in diameter. In addition, as indicated, thin films were made.

The details of preparation and any physical characteristics noted are set forth in Table XXIV:

TABLE XXIV

| Ex. No. | % Liq. | °C. | Thin Films |
|---|---|---|---|
| 357 | 70 | 190–195 | yes |
| 358 | 60 | 190 | yes |
| 359 | 50 | not reported | yes |
| 360 | 40 | not reported | yes |
| 361 | 30 | not reported | yes |

EXAMPLES 362 to 370

These Examples illustrate the polymer-compatible liquid concentration range useful for the formation of a homogeneous porous polymer intermediate from a "Surlyn" resin as utilized in previous Examples and diphenylether. In each Example the intermediate was about 0.5 inch in depth and about 2.5 inches in diameter. In addition, as indicated, thin films were made.

The details of preparation and any physical characteristics noted are set forth in Table XXV:

TABLE XXV

| Ex. No. | % Liq. | °C. | Thin Films |
|---|---|---|---|
| 362 | 90 | 207 | yes |
| 363 | 80 | 190 | yes |

TABLE XXV-continued

| Ex. No. | % Liq. | °C. | Thin Films |
|---|---|---|---|
| 364 | 70 | 200 | yes |
| 365 | 60 | 185 | yes |
| 366 | 50 | not reported | yes |
| 367 | 40 | not reported | — |
| 368 | 30 | not reported | — |
| 369 | 20 | not reported | — |
| 370 | 10 | not reported | — |

EXAMPLES 371 to 379

Examples 371 through 379 illustrate the polymer-compatible liquid concentration range useful for the formation of a homogeneous porous polymer intermediate from a "Surlyn" resin as utilized in previous Examples and dibutylphthalate. In each Example the intermediate was about 0.5 inch in depth and about 2.5 inches in diameter.

The details of preparation and any physical characteristics noted are set forth in Table XXVI:

TABLE XXVI

| Ex. No. | % Liq. | °C. | Remarks |
|---|---|---|---|
| 371 | 90 | 220 | — |
| 372 | 80 | 208 | — |
| 373 | 70 | 195 | — |
| 374 | 60 | 200 | — |
| 375 | 50 | 200 | — |
| 376 | 40 | not reported | — |
| 377 | 30 | not reported | — |
| 378 | 20 | not reported | — |
| 379 | 10 | not reported | — |

PRIOR ART EXAMPLES 380–384

EXAMPLES 380 to 384

Examples 380 to 384 are reproductions of various prior art compositions which are shown to have a physical structure different from that of the present invention.

EXAMPLE 380

A porous polymer was prepared in accordance with the process of Example 1 of U.S. Pat. No. 3,378,507, as modified to obtain a product with some physical integrity and to utilize a soap as the water-soluble anionic surfactant, in place of sodium bis(2-ethylhexyl) sulfosuccinate.

In a Brabender-Plasti-Corder internally heated blender, 33½ parts by weight of Exxon Chemical Corporation type LD 606 polyethylene and 66⅔ part of Ivory soap flakes were mixed at a machine temperature of about 350° F., until a homogeneous blend was formed. The material was then compression molded with a rubber type mold having a 2.5 inch by 5.0 inch cavity of a depth of 20 mils., at a temperature of about 350° F. and a pressure of 36,000 pounds per square inch. The resulting sample was continuously washed for about three days in a slow flowing stream of tap water and then sequentially washed by immersion in eight distilled water baths, each for a period of about one hour. The resulting sample still retained some soap and had poor handling properties.

FIGS. 47 and 48 are photomicrographs of the product of Example 380, at 195X and 2,000X amplification, respectively. It is apparent that the product is relatively non-uniform polymeric structure having neither distinct cellular cavities nor interconnecting pores.

EXAMPLE 381

A porous polymer was prepared in accordance with the process of Example 2, sample D, of U.S. Pat. No. 3,378,507, as modified to obtain a sample having some handling strength.

In a Brabender-Plasti-Corder internally heated blender, 75 parts of Ivory soap flakes and 25 parts of Exxon Chemical Corporation type LD 606 polyethylene were mixed at a machine temperature of about 350° F. and a sample temperature of about 330° F. until a homogeneous blend was formed. The material was then injection molded in a one-ounce Watson-Stillman injection molding machine having a mold cavity diameter of two inches and a depth of 20 mils. The resulting sample was continuously washed for about three days in a slowly flowing stream of tap water and then sequentially washed by immersion in eight distilled water baths, each for a period of about one hour. The resulting sample still retained some soap.

FIGS. 45 and 46 are photomicrographs of the product of Example 381, at 240X and 2400X amplification, respectively. The product of this example does not have the typical cellular structure of the present invention, as is apparent from the photomicrographs.

EXAMPLE 382

In accordance with the process of Example 3, sample A, of U.S. Pat. No. 3,378,507, a porous polymer was prepared.

In a Brabender-Plasti-Corder internally heated blender, 25 parts of Novamont Corporation type F300 and 8N19 polypropylene and 75 parts of Ivory soap flakes were mixed at a machine temperature of about 330° F. until a homogeneous blend was formed. The material was then compression molded with a rubber type mold. The resulting sample was found to have very little strength. A portion of the resulting sample was continuously washed for about three days in a slowly flowing stream of tap water and then sequentially washed by immersion in eight distilled water baths, each for a period of about one hour. The washed product was found to have extremely poor handling characteristics.

FIGS. 51 and 52 are photomicrographs of the product of Example 382 at 206X and 2000X amplification, respectively. The photomicrographs show that the product does not have the cellular structure of the present invention.

EXAMPLE 383

The process of Example 3, sample A, of U.S. Pat. No. 3,378,507 was modified to obtain a product having improved handling strength.

On an open two roll rubber mill, manufactured by the Bolling Company, 25 parts of Novamont Corporation type F300 8N19 polypropylene and 75 parts of Ivory soap flakes were mixed for about ten minutes at a temperature of about 350° F. until a homogeneous blend was formed. The material was then injection molded with a one-ounce Watson-Stillman injection molding machine having a mold cavity diameter of two inches and a depth of 20 mils. The resulting sample was continuously washed for about three days in a slowly flowing stream of tap water and then sequentially washed by immersion in eight distilled water baths, each for a period of about one hour. The resulting sample still retained some soap. The resulting product was found to be stronger than the product of Example 382.

FIGS. 49 and 50 are photomicrographs of the product of Example 383 at 195X and 2000X amplification, respectively. The irregular shapes shown by the photomicrographs are readily distinguishable from the structure of the present invention.

EXAMPLE 384

A porous polymer was prepared in accordance with Example II of U.S. Pat. No. 3,310,505, as modified to obtain a more homogeneous mixing of the materials.

In a Brabender-Plasti-Corder internally heated blender, 40 parts of Exxon Chemical Corporation type LD 606 polyethylene and 60 parts of Rohm and Haas Corporation polymethylmethacrylate were mixed, for about 10 minutes, at a machine temperature of about 350° F. until a homogeneous blend was formed. The material was then sheeted on a cold mill and subsequently compression molded using a heated four-inch circular die with a depth of 20 mils. and 30 tons of pressure for about ten minutes. The resulting composition was extracted for 48 hours with acetone in a large Soxlet extractor.

FIGS. 53 and 54 are photomicrographs of the product of Example 384 at 205X and 2000X amplification, respectively. The non-uniform structure shown by the photomicrographs is easily distinguished from the uniform structure of the present invention.

PHYSICAL CHARACTERIZATION OF EXAMPLES 225 AND 358

Figure 30:
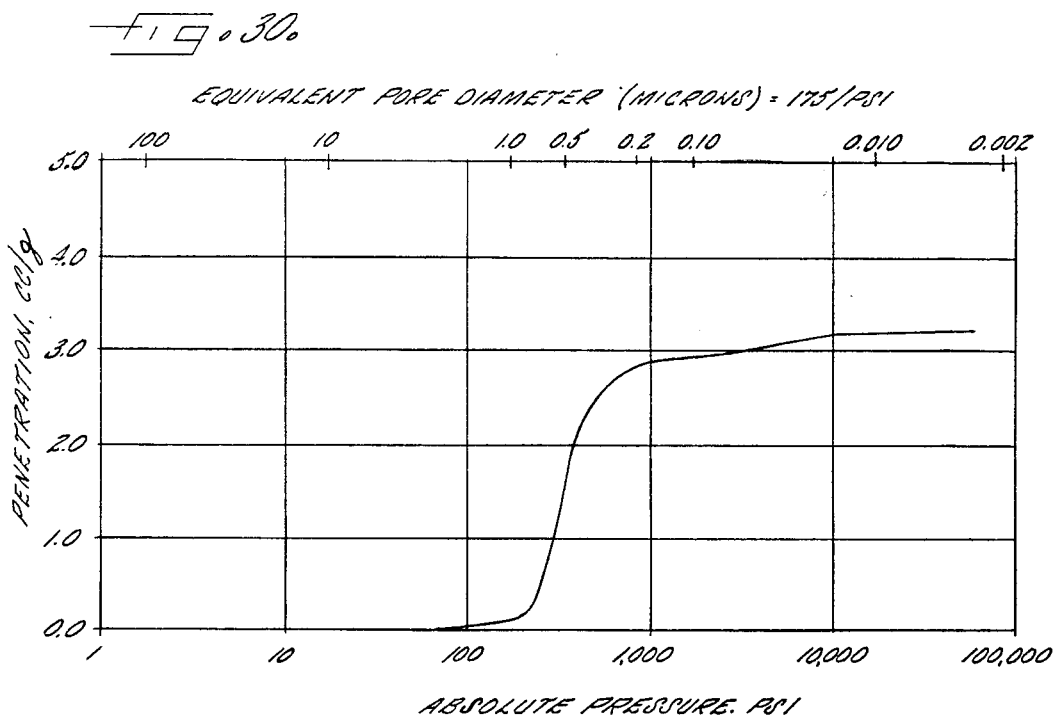
Figure 31:
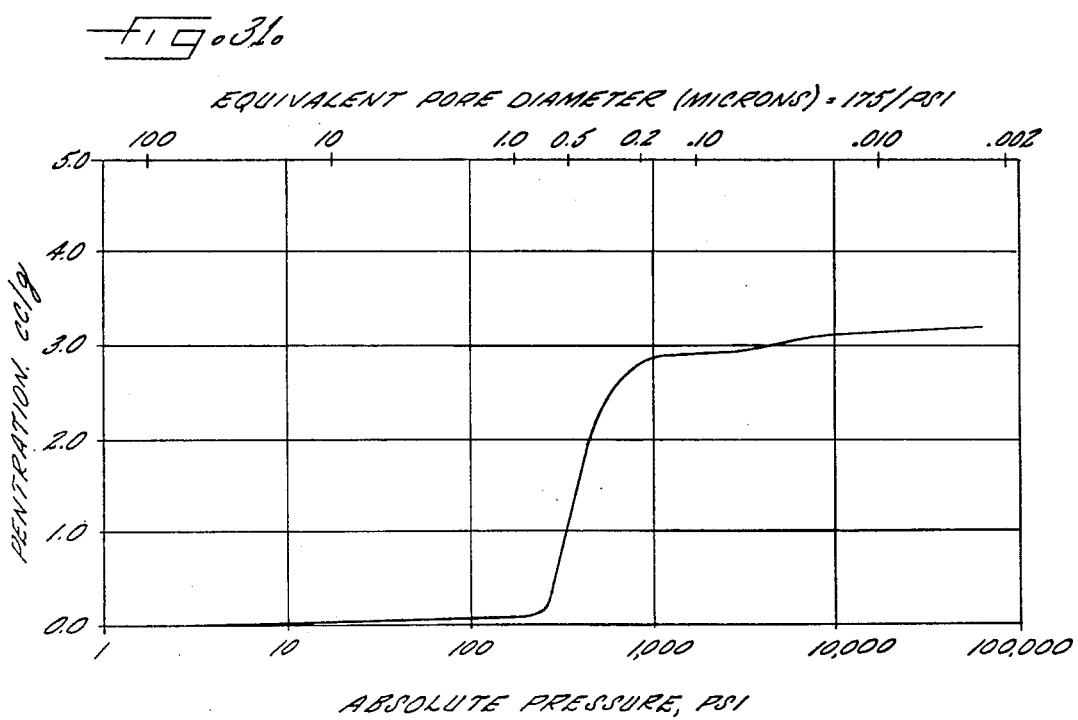
Figure 32:
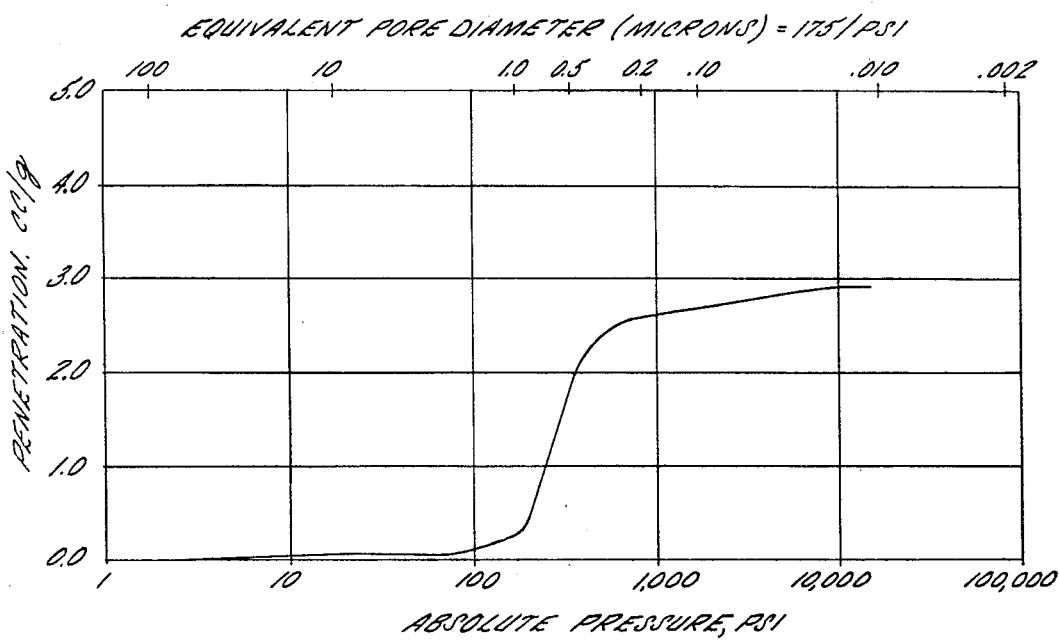

To obtain a quantitative understanding of the homogeneous structure of the present invention, certain samples of the microporous material and certain prior art samples were analyzed on an Aminco mercury intrusion porosimeter. FIGS. 30 and 31 are mercury intrusion curves of the one-half inch block of Example 225 which was made with 25 percent polypropylene and 75 percent N,N-bis(2-hydroxyethyl) tallowamine, and FIG. 32 is a mercury intrusion curve of the 6 inch block of Example 225. All mercury intrusion curves are shown on a semi-log graph with the equivalent pore sizes shown on the log scale abscissa. FIGS. 30 through 32 show the typical narrow distribution of pore sizes in the composition of the instant invention. It was determined that the one-half inch sample of Example 225 has a void space of about 76 percent and an average pore size of about 0.5 micron and the 6 inch block has a void space of about 72 percent and an average pore size of about 0.6 micron.

FIG. 33 is a mercury intrusion curve of the product of Example 358 which was made with 40 percent polypropylene and 60 percent N,N-bis(2-hydroxyethyl) tallowamine. FIG. 33 shows that the sample has the typical narrow pore size distribution. It was determined that the sample had a void space of about 60 percent and an average pore size of about 0.15 micron.

It is readily apparent that the compositions of this invention have such pore size distributions that at least 80 percent of the pores present in the composition fall within no more than one decade on the abscissa of the mercury intrusion curve. The pore size distribution of the composition may thus be characterized as "narrow".

PHYSICAL CHARACTERIZATION OF PRIOR ART COMMERCIAL COMPOSITIONS

EXAMPLE 385

Figure 34:
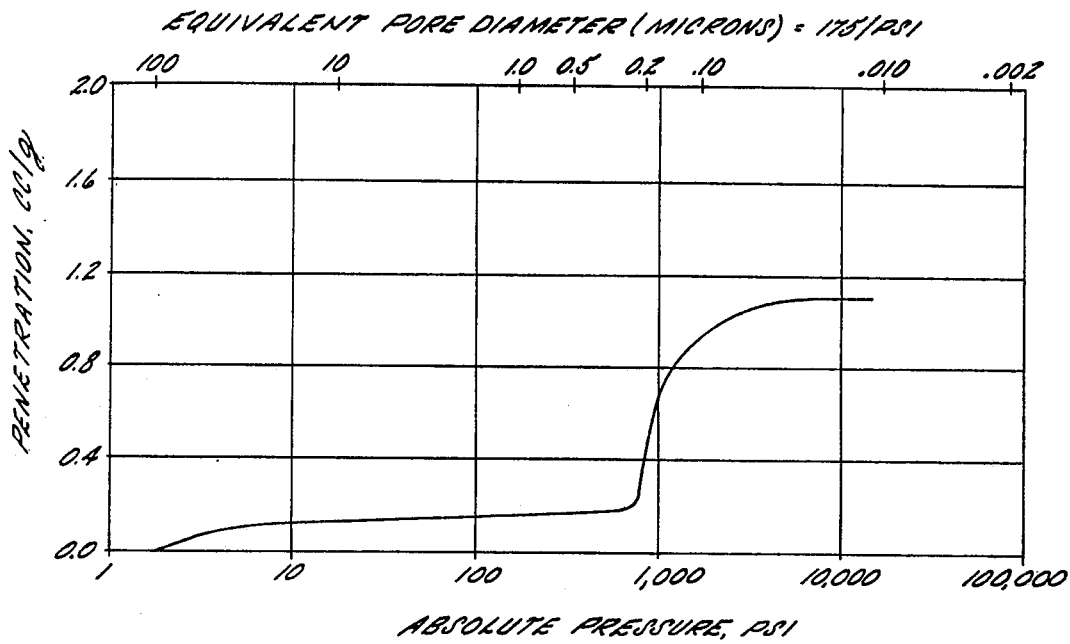

The composition of this example is commercially available Celgard 3501 microporous polypropylene, manufactured by Celanese. FIG. 34 is a mercury intrusion curve of the sample showing a large population of pores in the range of 70 to 0.3 microns. The sample was determined to have a void space of about 35 percent and an average pore size of about 0.15 micron.

EXAMPLE 386

Figure 35:
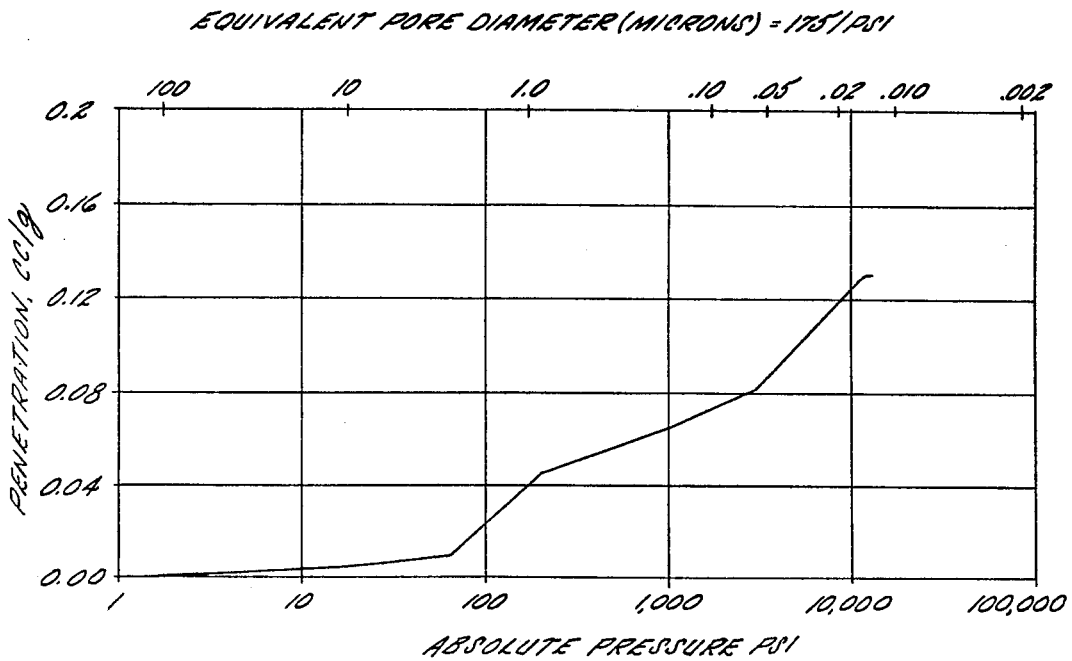

The composition of this example is commercially available A-20 microporous polyvinylchloride, manufactured by Amerace. FIG. 35 is a mercury intrusion curve of the sample and shows a very broad pore size distribution. The sample was determined to have a void space of about 75 percent and an average pore size of about 0.16 microns.

EXAMPLE 387

Figure 36:
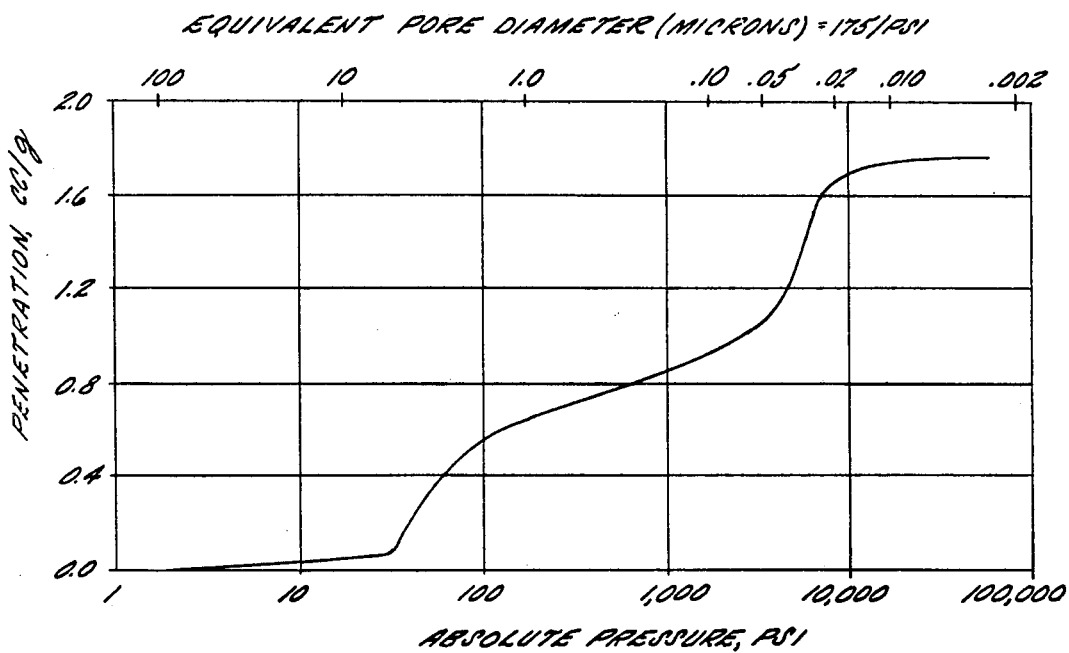

The composition of this example is commercially available A-30 microporous polyvinylchloride and manufactured by Amerace. FIG. 36 is a mercury intrusion curve of the sample and shows a very wide pore size distribution. The sample was determined to have a void space of about 80 percent and an average pore size of about 0.2 micron.

EXAMPLE 388

The composition of this example is commercially available Porex microporous polypropylene. FIG. 37 is a mercury intrusion curve of the sample showing a very broad distribution of extremely small cells as well as a distribution of very large cells. The sample was determined to have a void space of about 12 percent and an average pore size of about one micron.

EXAMPLE 389

The composition of this example is commercially available Millipore BDWP 29300 microporous polyvinylchloride. FIG. 38 is a mercury intrusion curve of the sample showing a relatively narrow distribution in the range of 0.5 to 2 microns as well as a number of cells smaller than about 0.5 micron. The sample was determined to have a void space of about 72 percent and an average pore size of about 1.5 microns.

EXAMPLES 392 to 399

These examples illustrate the polymer/compatible liquid concentration range useful for the formation of homogeneous porous polymer intermediates from polymethylmethacylate and 1,4-butane diol using the standard preparation procedure. In each example the intermediate formed was about 0.5 inches in depth and about 2.5 inches in diameter. The polymethylmethacrylate was supplied by Rohm and Haas under the designation Plexiglass Acrylic Plastic Molding Powder, lot number 386491. The details of preparation are set forth in Table XXVII:

TABLE XXVII

| EXAMPLE NO. | % LIQUID | TEMP., °C. |
|---|---|---|
| 392 | 90 | 215 |
| 393 | 85 | 225 |
| 394 | 80 | 225 |
| 395 | 70 | 210 |

TABLE XXVII-continued

| EXAMPLE NO. | % LIQUID | TEMP., °C. |
|---|---|---|
| 396 | 60 | 229 |
| 397 | 50 | 230 |
| 398 | 40 | 229 |
| 399 | 30 | 225 |

The 1,4-butanediol was removed from the product of Example 395 and the resultant structure was determined to be the cellular structure of the present invention, as may be seen from FIG. 61 which shows the microporous product at 5000X amplification. The same polymer/liquid system as that of Example 394 was also cooled at rates up to 4000° C. per minute and still produced the cellular structure of the present invention.

EXAMPLE 400

The porous polymer intermediate was prepared using the standard preparation procedure and heating 30 percent polymethylmethacrylate, as utilized in the previous examples, and 70 percent lauric acid to 175° C. and cooling to form the porous polymer intermediate. The lauric acid was removed from the resultant intermediate to form the microporous cellular structure of the present invention.

EXAMPLE 401

The porous polymer intermediate was prepared using the standard preparation procedure and heating 30 percent Nylon 11, supplied by Aldrich Chemical Company, and 70 percent ethylene carbonate to a temperature of 218° C. and then cooling the resultant solution to form the porous polymer intermediate. The ethylene carbonate was removed from the intermediate and the resultant microporous polymer was determined to have the cellular structure of the present invention.

EXAMPLE 402

The porous polymer intermediate was prepared using the standard preparation procedure and heating 30 percent Nylon 11, as utilized in the previous Example, and 70 percent 1,2-propylene carbonate was removed from the intermediate and the resultant microporous polymer was determined to have the cellular structure of the present invention.

EXAMPLES 403–422

Examples 403–422 demonstrate the formation of the porous polymer intermediates from polymer/liquid systems containing various amounts of Nylon 11, as utilized in previous Examples, and tetramethylene sulfone, supplied by Shell under the designation Sulfone W, and containing approximately 2.5 percent water. The various concentrations were cooled at various rates and from various solution temperatures, as indicated in Table XXVIII; which also demonstrates that increased cooling rates and increased concentration of the polymer cause the resulting cell sizes to decrease, in general.

TABLE XXVIII

| Ex. No. | % Liq. | T °C. | Cooling Rate °C./Min. | Cell Size (Microns) |
|---|---|---|---|---|
| 403 | 90 | 195 | 20 | 10 |
| 404 | 80 | 198 | 5 | 15 |
| 405 | 80 | 198 | 20 | 14 |
| 406 | 80 | 198 | 40 | 9 |
| 407 | 80 | 198 | 80 | 5.5 |

TABLE XXVIII-continued

| Ex. No. | % Liq. | T °C. | Cooling Rate °C./Min. | Cell Size (Microns) |
|---|---|---|---|---|
| 408 | 70 | 200 | 5 | 11 |
| 409 | 70 | 200 | 20 | 5 |
| 410 | 70 | 200 | 40 | 6.5 |
| 411 | 70 | 200 | 80 | 6.5 |
| 412 | 60 | 205 | 5 | 5 |
| 413 | 60 | 205 | 20 | 4.5 |
| 414 | 60 | 205 | 40 | 4 |
| 415 | 60 | 205 | 80 | 3.5 |
| 416 | 50 | 210 | 20 | 3 |
| 417 | 50 | 210 | 40 | 1.5 |
| 418 | 50 | 210 | 80 | 2 |
| 419 | 60 | 212 | 20 | — |
| 420 | 70 | 215 | 20 | — |
| 421 | 80 | 217 | 20 | — |
| 422 | 90 | 220 | 20 | — |

The foregoing Table XXVIII also demonstrates that at concentrations from 40 percent to 10 percent liquid, there is no resulting visible porosity, for the system cooled at 20° C. per minute. Such results are entirely anticipated as may be seen by referring to FIG. 62 which shows the melt curve for the Nylon 11/tetramethylene Sulfone concentration range, as well as the crystallization curves at the various rates of cooling. It is apparent from FIG. 62 that at 20° C./minute cooling rate, the system containing 40% liquid does not fall within the substantially flat portion of the crystallization curve and thus would not be expected to form the desired microporous structure. FIG. 63 is a photomicrograph at 2000X amplification of Example 409 showing the typical cellular structure of Examples 403-418.

EXAMPLE 423

The porous polymer intermediate was prepared by using the standard preparation procedure and heating 30 percent polycarbonate supplied by General Electric under the designation Lexan and 70 percent menthol to a temperature of 206° C. and cooling to form the porous polymer intermediate. The menthol was extracted and a cellular microporous structure resulted as shown in FIG. 64, which is a photomicrograph of the product of this Example at 2000X amplification.

EXAMPLE 424

This Example demonstrates the formation of the microporous cellular structure of the present invention from poly-2,6-dimethyl-1,4-phenylene oxide, supplied by Scientific Polymer Products, commonly referred to as polyphenylene oxide. The homogeneous microporous polymer intermediate was made from 30 percent of said polyphenylene oxide and 70 percent N,N-bis(2-hydroxyethyl) tallowamine which was heated to a solution temperature of 275° C. and the intermediate was formed using the standard preparation procedure. The liquid was removed from the intermediate and the cellular structure of the present invention resulted, as may be seen from FIG. 65 which is a photomicrograph of the product of this Example at 2000X amplification.

EXAMPLE 425

This Example demonstrates the formation of the non-cellular product of this invention by cooling a homogeneous solution of 40 percent polypropylene, as utilized in the previous Examples, and 60 percent dibutyl phthalate. The solution was extruded onto a chilled belt at a thickness of about 10 mils and the cooling rate was in excess of 2,400° C. A quantity of dispersol was applied to the surface of the belt at a point prior to the solution being extruded thereon. The liquid was removed from the resultant film and a non-cellular microporous product resulted, as may be seen from FIG. 65 which is a photomicrograph of the product of this Example at 2000X amplification.

EXAMPLE 426

This Example demonstrates the formation of the non-cellular product of this invention by cooling a homogeneous solution of 25 percent polypropylene, as utilized in previous examples, and 75 percent N,N-bis(2-hydroxyethyl) tallowamine in the same manner as that of Example 425. The liquid was removed from the resultant film and a non-cellular microporous product resulted, as may be seen from FIG. 67 which is a photomicrograph of the product of this Example at 2000X amplification.

The products of Examples 425 and 426 were analyzed by mercury intrusion porosimetry and their respective intrusion curves are shown in FIGS. 68 and 69. It is apparent that both products have generally narrow pore size distributions, but the product of Example 426 demonstrates a much narrower distribution than the product of Example 425. Thus, the product of Example 425 has a calculated S value of 24.4 whereas the product of Example 426 has a calculated S value of only 8.8. The average pore size of Example 425 is, however, very small, 0.096 microns, whereas the average pore size of the product of Example 426 is 0.589.

To quantitatively demonstrate the uniqueness of the cellular compositions of the present invention, a number of such microporous products were prepared in accordance with the standard preparation procedure and the details relating thereto are summarized in Examples 427-457 in Table XXIX. The products of said Examples were analyzed by mercury intrusion porosity to determine their respective average pore diameter and the S values and by scanning electron microscopy to determine their average cell size, S. The result of such analysis are shown in Table XXX.

TABLE XXIX

| Ex. No. | Polymer | Liquid | % Void | Solution Temp. °C. |
|---|---|---|---|---|
| 427 | polypropylene | N,N-bis(2-hydroxyl-ethyl) tallowamine | 75 | 180 |
| 428 | polypropylene | N,N-bis(2-hydroxyl-ethyl) tallowamine | 60 | 210 |
| 429 | polypropylene | diphenylether | 90 | 200 |
| 430 | polypropylene | diphenylether | 80 | 200 |
| 431 | polypropylene | diphenylether | 70 | 200 |
| 432 | polypropylene | 1,8-diaminooctane | 70 | 180 |
| 433 | polypropylene | phenylsalicylate | 70 | 240 |
| 434 | polypropylene | 4-bromodiphenyl-ether | 70 | 200 |
| 435 | polypropylene | tetrabromoethane | 90 | 180 |
| 436 | polypropylene | N-octyldiethanol-amine | 75 | — |
| 437 | polypropylene | N-hexyldiethanol-amine | 75 | 260 |
| 438 | polypropylene | salicylaldehyde | 70 | 185 |
| 439 | low density polyethylene | hexanoic acid | 70 | 190 |
| 440 | low density polyethylene | 1-octanol | 70 | 178 |
| 441 | low density polyethylene | dibutyl sebacate | 70 | 238 |
| 442 | low density polyethylene | Phosclere EC-53 | 70 | 191 |
| 443 | low density polyethylene | dicapryl adipate | 70 | 204 |
| 444 | low density polyethylene | diisooctyl phthalate | 70 | 204 |

TABLE XXIX-continued

| Ex. No. | Polymer | Liquid | % Void | Solution Temp. °C. |
|---|---|---|---|---|
| 445 | low density polyethylene | dibutyl phthalate | 70 | 290 |
| 446 | high density polyethylene | N,N-bis(2-hydroxyethyl) tallowamine | 80 | 250 |
| 447 | polystyrene | 1-dodecanol | 75 | 220 |
| 448 | polystyrene | 1,3-bis(4-piperdine) propane | 70 | 186 |
| 449 | polystyrene | diphenylamine | 70 | 235 |
| 450 | polystyrene | N-hexyldiethanolamine | 75 | 260 |
| 451 | polystyrene | Phosclere P315C | 70 | 270 |
| 452 | polymethylmethacrylate | 1,4-butanediol | 70 | — |
| 453 | polymethylmethacrylate | 1,4-butanediol | 85 | — |
| 454 | Surlyn | diphenylether | 70 | 185–207 |
| 455 | Surlyn | dibutyl phthalate | 70 | 195 |
| 456 | Noryl | N,N-bis(2-hydroxyethyl) tallowamine | 75 | 250 |
| 457 | Nylon 11 | ethylene carbonate | 70 | — |

TABLE XXX

| Ex. No. | C | P | C/P | S | log C/P | log S/C |
|---|---|---|---|---|---|---|
| 427 | 5.0 | 0.520 | 9.6 | 2.86 | 0.982 | −0.243 |
| 428 | 3.18 | 0.112 | 28.4 | 5.0 | 1.45 | 0.197 |
| 429 | 22.5 | 11.6 | 1.94 | 4.52 | 0.288 | −0.697 |
| 430 | 6.49 | 0.285 | 22.8 | 27.1 | 1.36 | 0.621 |
| 431 | 6.72 | 0.136 | 49.4 | 7.01 | 1.69 | 0.0183 |
| 432 | 13.0 | 0.498 | 26.1 | 2.36 | 1.42 | −0.741 |
| 433 | 13.8 | 0.272 | 50.7 | 4.29 | 1.71 | −0.507 |
| 434 | 3.35 | 0.137 | 24.5 | 5.25 | 1.39 | 0.195 |
| 435 | 15.4 | 0.804 | 19.2 | 5.13 | 1.28 | −0.477 |
| 436 | 16.6 | 0.850 | 19.5 | 2.52 | 1.29 | −0.819 |
| 437 | 20.0 | 0.631 | 31.7 | 2.51 | 1.50 | −0.901 |
| 438 | 7.9 | 0.105 | 75.2 | 3.22 | 1.88 | −0.390 |
| 439 | 7.5 | 1.16 | 6.47 | 8.62 | 0.811 | 0.0604 |
| 440 | 6.8 | 1.00 | 6.8 | 3.53 | 0.833 | 0.285 |
| 441 | 5.85 | 0.636 | 9.20 | 6.07 | 0.964 | 0.0160 |
| 442 | 3.40 | 0.512 | 6.64 | 5.30 | 0.822 | 0.193 |
| 443 | 5.0 | 0.871 | 5.74 | 8.21 | 0.759 | 0.215 |
| 444 | 4.75 | 0.631 | 7.53 | 3.54 | 0.877 | −0.128 |
| 445 | 7.8 | 1.18 | 6.61 | 3.82 | 0.820 | −0.310 |
| 446 | 34.5 | 0.696 | 49.6 | 4.34 | 1.70 | −0.900 |
| 447 | 28.2 | 1.88 | 15.0 | 3.40 | 1.18 | −0.919 |
| 448 | 1.08 | 0.0737 | 14.7 | 2.87 | 1.17 | 0.424 |
| 449 | 6.65 | 0.631 | 10.5 | 63.5 | 1.02 | 0.980 |
| 450 | 7.4 | 0.164 | 45.1 | 3.74 | 1.65 | −0.296 |
| 451 | 1.4 | 0.151 | 9.27 | 2.26 | 0.967 | 0.208 |
| 452 | 9.2 | 0.201 | 45.8 | 3.68 | 1.66 | −0.398 |
| 453 | 114 | 10.3 | 11.1 | 5.19 | 1.05 | −1.34 |
| 454 | 6.8 | 0.631 | 10.8 | 2.13 | 1.03 | −0.504 |
| 455 | 5.6 | 0.769 | 7.28 | 2.09 | 0.862 | −0.428 |
| 456 | 19.0 | 0.179 | 106 | 2.74 | 2.03 | −0.841 |
| 457 | 5.8 | 0.372 | 15.6 | 7.56 | 1.19 | 0.112 |

TABLE XXXI

| Ex. No. | Prior Art Description | Polymer Type |
|---|---|---|
| 458 | Celgard 3501 | polypropylene |
| 459 | Amerace A-30 | polyvinylchloride |
| 460 | Porex | polypropylene |
| 461 | Milipore EG | cellulosic |
| 462 | Metricel GA-8 | cellulosic |
| 463 | Sartorius SM 12807 | polyvinylchloride |
| 464 | Millipore HAWP | cellulosic |
| 465 | Millipore G5WP 04700 | cellulosic |
| 466 | Millipore VMWP 04700 | cellulosic |
| 467 | Amicon 5UM05 | cellulosic |
| 468 | Celgard 2400 | polypropylene |
| 469 | Millipore SMWP 04700 | polyvinylchloride |
| 470 | Celgard 2400 | polypropylene |
| 471 | Product of Example 381 | polyethylene |
| 472 | Product of Example 380 | polyethylene |
| 473 | Product of Example 383 | polypropylene |

TABLE XXXI-continued

| Ex. No. | Prior Art Description | Polymer Type |
|---|---|---|
| 474 | Product of Example 384 | polyethylene |

TABLE XXXII

| Ex. No. | C | S | log S/C |
|---|---|---|---|
| 458 | 0.04* | 2.32 | 1.76 |
| 459 | 0.3 | 138 | 2.66 |
| 460 | 186 | 2.41 | −1.89 |
| 461 | 0.2* | 26.3 | 1.85 |
| 462 | 0.2* | 9.14 | 1.66 |
| 463 | 0.2* | 31.5 | 2.2 |
| 464 | 0.8* | 2.94 | 0.565 |
| 465 | 0.22* | 1.64 | 0.872 |
| 466 | 0.05* | 5.37 | 2.03 |
| 467 | 2.10** | 61.8 | 1.79 |
| 468 | 0.02* | 5.08 | 2.40 |
| 469 | 5* | 1.55 | −0.509 |
| 470 | 0.04* | 5.64 | 2.15 |
| 471 | 1.1** | 11.5 | 1.019 |
| 472 | 0.8** | 17.5 | 1.34 |
| 473 | 0.56 | 16.8 | 1.477 |
| 474 | 70 | 1.34 | −1.718 |

*From company product information
**From mercury intrusion

The data contained in Tables XXIX through XXXII is summarized in FIG. 70 which is a plot of the log S/C vs. log C/P. From FIG. 70 it is apparent that the cellular structure of the present invention may be defined at having a log C/P of from about 0.2 to about 2.4 and a log S/C of from about −1.4 to about 1.0, and more usually said polymer will have a log C/P of from about 0.6 to about 2.2 and a log S/C of from about −0.6 to about 0.4.

Thus, as has been seen, the present invention provides a facile method for preparing microporous polymers any synthetic thermoplastic polymer in widely varying thicknesses and shapes. The microporous polymers may possess a unique microcellular configuration and are in any event characterized by pore diameters with relatively narrow size distribution. These structures are formed by first selecting a liquid that is compatible with a polymer, i.e.—forms a homogeneous solution with the polymer and can be removed from the polymer after cooling and then selecting the amount of the liquid and carrying out the cooling of the solution in a fashion which insures that the desired microporous polymer configuration will result.

As can be also seen, the present invention also provides microporous polymer products which contain relatively large amounts of functionally useful liquids such as a polymer additive and behave as a solid. These products may be advantageously utilized in a variety of applications such as, for example, in masterbatching.

What is claimed is:

1. A method of preparing a relatively homogeneous, isotropic, three-dimensional microporous polymer structure comprising heating a mixture of a synthetic thermoplastic polymer selected from the group consisting of olefinic polymers, condensation polymers, oxidation polymers, and blends thereof, and a compatible liquid to a temperature and for a time sufficient to form a homogeneous solution, allowing said solution to assume a desired shape, cooling said solution in said desired shape at a rate and to a temperature sufficient to initiate thermodynamic, non-equilibrium liquid-liquid phase separation, continuing cooling to form a solid, and removing at least a substantial portion of the liquid from the resulting solid to form the microporous polymer structure.

2. The method of claim 1 wherein essentially all of the liquid is removed.

3. The method of claim 1 wherein said mixture comprises from about 10 to about 90% by weight of the liquid.

4. The method of claim 1 wherein the homogeneous solution is cast into a film as it is cooled.

5. The method of claim 1 wherein the homogeneous solution is cast into the form of a block as it is cooled.

6. The method of claim 5 wherein the block has a thickness up to about 2½ inches.

7. The method of claim 1 wherein the homogeneous liquid, as it is cooled, is cast onto a substrate which forms an essentially non-cellular skin on the surface of the microporous polymer in contact with said substrate.

8. The method of claim 7 wherein the skin formed is relatively impervious to liquids.

9. The method of claim 1 wherein the polymer is a non-acrylic polyolefin.

10. The method of claim 1 wherein the polymer is selected from the group consisting of low density polyethylene, high density polyethylene, polypropylene, polystyrene, polyvinylchloride, acrylonitrile-butadiene-styrene terpolymers, styrene-acrylonitrile copolymers, styrene butadiene copolymers, poly (4-methyl-pentene-1), polybutylene, polyvinylidene chloride, polyvinyl butryal, chlorinated polyethylene, ethylenevinyl acetate copolymers, polyvinyl acetate and polyvinyl alcohol.

11. The method of claim 1 wherein the polymer is an acrylic pololefin.

12. The method of claim 1 wherein the polymer is selected from the group consisting of polymethyl-methacrylate, polymethyl-acrylate, ethylene-acrylic acid copolymers, and ethylene-acrylic acid metal salt copolymers.

13. The method of claim 1 wherein the polymer is an oxidation polymer.

14. The method of claim 1 wherein the polymer is polyphenylene oxide.

15. The method of claim 1 wherein the polymer is selected from the group consisting of polyethylene terephthalate, polybutylene terephthalate, Nylon 6, Nylon 11, Nylon 13, Nylon 66, polycarbonates and polysulfone.

16. A method of preparing a relatively homogeneous, isotropic, three-dimensional microporous polymer structure comprising heating a mixture of a polymer selected from the group consisting of olefinic polymers, condensation polymers, oxidation polymers, and blends thereof, and a compatible liquid to a temperature and for a time sufficient to form a homogeneous solution, forming at substantially the same time a plurality of liquid droplets of substantially the same size in a continuous liquid polymer phase by cooling the solution, continuing said cooling to solidify the polymer, and removing at least a substantial portion of the liquid from the resulting solid to form the cellular polymer structure.

17. The method of claim 16 wherein essentially all of the liquid is removed.

18. The method of claim 16 wherein said mixture comprises from about 10 to about 90% by weight of the liquid.

19. The method of claim 16 wherein the homogeneous solution is cast into a film as it is cooled.

20. The method of claim 16 wherein the homogeneous solution is cast into the form of a block as it is cooled.

21. The method of claim 20 wherein the block has a thickness up to about 2½ inches.

22. The method of claim 20 wherein the homogeneous liquid, as it is cooled, is cast onto a substrate which forms an essentially non-cellular skin on the surface of the microporous polymer in contact with said substrate.

23. The method of claim 22 wherein the skin formed is relatively impervious to liquids.

24. The method of claim 16 wherein the polymer is a non-acrylic polyolefin.

25. The method of claim 16 wherein the polymer is selected from the group consisting of low density polyethylene, high density polyethylene, polypropylene, polystyrene, polyvinylchloride, acrylonitrile-butadiene-styrene terpolymers, styrene-acrylonitrile copolymers, styrene butadiene copolymers, poly (4-methyl-pentene-1), polybutylene, polyvinylidene chloride, polyvinyl butyral, chlorinated polyethylene, ethylenevinyl acetate copolymers, polyvinyl acetate and polyvinyl alcohol.

26. The method of claim 16 wherein the polymer is an acrylic polyolefin.

27. The method of claim 16 wherein the polymer is selected from the group consisting of polymethyl-methacrylate, polymethyl-acrylate, ethylene-acrylic acid copolymers, and ethylene-acrylic acid metal salt copolymers.

28. The method of claim 16 wherein the polymer is an oxidation polymer.

29. The method of claim 16 wherein the polymer is polyphenylene oxide.

30. The method of claim 16 wherein the polymer is selected from the group consisting of polyethylene terephthalate, polybutylene terephthalate, Nylon 6, Nylon 11, Nylon 13, Nylon 66, polycarbonates and polysulfone.

31. A method of preparing a relatively homogeneous isotropic, three-dimensional microporous cellular polymer structure comprising heating a mixture of a polymer selected from the group consisting of olefinic polymers, condensation polymers, oxidation polymers, and blends thereof, and a compatible liquid to a temperature and for a time sufficient to form a homogeneous solution, forming at substantially the same time a plurality of liquid droplets of substantially the same size in a continuous liquid polymer phase by cooling the solution, continuing cooling to solidify the polymer, at least partially displacing the compatible liquid with a member selected from the group consisting of an intermediate displacing liquid and a functionally useful liquid selected from the group consisting of lubricants, surfactants, slip agents, moth repellents, pesticides, plasticizers, medicinals, fuel additives, polishing agents, stabilizers, insect repellents, fragrances, flame retardants, antioxidants, odor masking agents, antifogging agents and perfumes, with the proviso that when an intermediate displacing liquid is used the intermediate displacing liquid is thereafter at least partially displaced with a functionally useful liquid.

32. The method of claim 31 wherein said compatible liquid is essentially completely displaced.

33. The method of claim 32 wherein said compatible liquid is displaced by an intermediate displacing liquid.

34. The method of claim 33 wherein said intermediate displacing liquid is substantially completely displaced by said functionally useful liquid.

35. The method of claim 31 wherein the polymer is an olefinic polymer.

36. The method of claim 31 wherein the polymer is a condensation polymer.

37. The method of claim 31 wherein the polymer is an oxidation polymer.

* * * * *